(12) United States Patent
Pêgo et al.

(10) Patent No.: US 10,858,484 B2
(45) Date of Patent: Dec. 8, 2020

(54) BIODEGRADABLE DENDRITIC STRUCTURE, METHODS AND USES THEREOF

(71) Applicant: INEB—INSTITUTO NACIONAL DE ENGENHARIA BIOMEDICA, Oporto (PT)

(72) Inventors: Ana Paula Pêgo, Oporto (PT); Victoria Leiro, Oporto (PT); Eduardo Fernandez Megia, Santiago de Compostela (PT); Ricardo Riguera Vega, Santiago de Compostela (PT)

(73) Assignee: INEB—INSTITUTO NACIONAL DE ENGENHARIA BIOMEDICA, Oporto (PT)

( * ) Notice: Subject to any disclaimer, the term of this patent is extended or adjusted under 35 U.S.C. 154(b) by 3 days.

(21) Appl. No.: 16/303,971

(22) PCT Filed: May 23, 2017

(86) PCT No.: PCT/IB2017/053047
§ 371 (c)(1),
(2) Date: Nov. 21, 2018

(87) PCT Pub. No.: WO2017/203437
PCT Pub. Date: Nov. 30, 2017

(65) Prior Publication Data
US 2020/0190265 A1 Jun. 18, 2020

(30) Foreign Application Priority Data

May 23, 2016 (PT) .......................................... 109408

(51) Int. Cl.
| | | |
|---|---|---|
| C08G 83/00 | (2006.01) | |
| A61K 47/60 | (2017.01) | |
| A61K 47/34 | (2017.01) | |
| A61K 49/12 | (2006.01) | |

(52) U.S. Cl.
CPC ............ *C08G 83/003* (2013.01); *A61K 47/34* (2013.01); *A61K 47/60* (2017.08); *A61K 49/124* (2013.01)

(58) Field of Classification Search
USPC ........................................................ 528/219
See application file for complete search history.

(56) References Cited

U.S. PATENT DOCUMENTS

| | | |
|---|---|---|
| 2004/0131582 A1 | 7/2004 | Grinstaff et al. |
| 2004/0151689 A1 | 8/2004 | Tomalia et al. |
| 2007/0100002 A1 | 1/2007 | Leinweber et al. |
| 2015/0291522 A1 | 10/2015 | Tyler et al. |

FOREIGN PATENT DOCUMENTS

| | | |
|---|---|---|
| CN | 101337076 A | 1/2009 |
| CN | 103055328 A | 4/2013 |
| CN | 103881108 A | 6/2014 |
| WO | 0138423 A1 | 5/2001 |
| WO | 02067908 A1 | 9/2002 |
| WO | 2005003260 A1 | 1/2005 |
| WO | 2011053618 A2 | 5/2011 |
| WO | 2012049338 A1 | 4/2012 |
| WO | 2014084743 A1 | 6/2014 |

OTHER PUBLICATIONS

Klajnert, B. et al., "Dendrimers reduce toxicity of Aβ 1-28 peptide during aggregation and accelerate fibril formation" Nanomedicine: Nanotechnology, Biology and Medicine Nov. 2012, vol. 8, n°8, pp. 1372-1378 Introdução, página 1373.
Victoria Leiro et al, "Dendrimers as Powerful Building Blocks in Central Nervous System Disease: Headed for Successful Nanomedicine", www.advancedsciencenews.com, www.afm-journal.de, 2017, Wiley-VCH Verlag GmbH & Co. KGaA, Weinheim, pp. 1-20.
Victoria Leiro et al, "Delivering siRNA with Dendrimers: In Vivo Applications", Current Gene Therapy, 2017, vol. 17, No. 1, Bentham Science Publishers, pp. 1-16.
María De La Fuente et al, "Exploring the efficiency of gallic acid-based dendrimers and their block copolymers with PEG as gene carriers", Nanomedicine, GB, (Nov. 1, 2012), vol. 7, No. 11, doi:10.2217/nnm.12.51, ISSN 1743-5889, pp. 1667-1681, XP055406682 [AD] 1-26 abstract.
Victoria Leiro et al, "The Present and the Future of Degradable Dendrimers and Derivatives in Theranostics", Bioconjugate Chemistry, (Jul. 15, 2015), vol. 26, No. 7, doi:10.1021/bc5006224, ISSN 1043-1802, pp. 1182-1197, XP055406380 [AD] 1-26 p. 1183, col. 2.
Victoria Leiro et al, "Biodegradable PEG-dendritic block copolymers: synthesis and biofunctionality assessment as vectors of siRNA", Journal of Materials Chemistry B, GB, (Jan. 1, 2017), vol. 5, No. 25, doi:10.1039/C7TB00279C, ISSN 2050-750X, pp. 4901-4917, XP055406674 [XDP] 1-26 the whole document.
Svenson, S.; Tomalia, D., "Dendrimers in biomedical applications—reflections on the field.", Adv Drug Deliver Rev, (20050000), vol. 57, doi:doi:10.1016/j.addr.2005.09.018, pp. 2106-2129, XP025283969.
Rolland, O.; Turrin, C. O.; Caminade, A. M.; Majoral, J. P., "Dendrimers and nanomedicine: multivalency in action", New J. Chem, (20090000), vol. 33, pp. 1809-1824.
Medina, S. H.; El-Sayed, M. E., "Dendrimers as carriers for delivery of chemotherapeutic agents.", Chem. Rev., (20090000), vol. 109, pp. 3141-3157.

(Continued)

*Primary Examiner* — Terressa Boykin
(74) *Attorney, Agent, or Firm* — Leason Ellis LLP

(57) ABSTRACT

The present disclosure relates to biodegradable and biocompatible dendritic repeating unit/scaffold (bRU), to a method of synthesis of biodegradable and biocompatible dendritic repeating unit/scaffold (bRU) and to the biomedical applications of biodegradable and biocompatible dendritic repeating unit/scaffold (bRU). This bRU is useful as scaffold to synthesize fully biodegradable dendrimers and/or "mix" or "hybrid" biodegradable dendrimers, presenting a biodegradable shell and a hydrolytically stable/non-degradable core of already existing dendritic systems, in particular it relates to a Biodegradable dendritic structure of formula (I).

22 Claims, 62 Drawing Sheets

Specification includes a Sequence Listing.

(56) References Cited

OTHER PUBLICATIONS

Tekade, R. K.; Kumar, P. V.; Jain, N. K., "Dendrimers in oncology: an expanding horizon.", Chem. Rev., (20090000), vol. 109, pp. 49-87.

Mintzer, M. A.; Grinstaff, M. W., "Biomedical applications of dendrimers: a tutorial.", Chem. Soc. Rev., (20110000), vol. 40, pp. 173-190.

Barth, R. F.; Adams, D. M.; Soloway, A. H.; Alam, F.; Darby, M. W., "Boronated starburst dendrimer-monoclonal antibody immunoconjugates: evaluation as a potential delivery system for neutron capture therapy.", Bioconjugate Chemistry, (19940000), vol. 5, doi:doi:10.1021/bc00025a008, pp. 58-66, XP000430385.

Malik, N.; Evagorou, E.; Duncan, R., "Dendrimer-platinate: a novel approach to cancer chemotherapy.", Anticancer Drugs, (19990000), vol. 10, doi:doi:10.1097/00001813-199909000-00010, pp. 767-776, XP000991393.

Malik, N.; Wiwattanapatapee, R.; Klopsch, R.; Lorenz, K.; Frey, H.; Weener, J. W.; Meijer, E. W.; Paulus, W.; Duncan, R., "Dendrimers: relationship between structure and biocompatibility in vitro, and preliminary studies on the biodistribution of I-labelled polyamidoamine dendrimers in vivo", Journal of Controlled Release, (20000000), vol. 65, doi:doi:10.1016/S0168-3659(99)00246-1, pp. 133-148, XP004190318.

Jain, K.; Kesharwani, P.; Gupta, U.; Jain, N. K., "Dendrimer toxicity: let's meet the challenge", International Journal of Pharmaceutics, (20100000), vol. 394, pp. 122-142, XP027083834.

Yashima, E.; Matsushima, T.; Okamoto, Y., "Chirality assignment of amines and amino alcohols based on circular dichroism induced by helix formation of a stereoregular poly((4-carboxyphenyl)acetylene) through acid-base complexation", J Am Chem Soc, (19970000), vol. 119, doi:doi:10.1021/ja964470y, pp. 6345-6359, XP001118318.

Labieniec, M.; Ulicna, O.; Vancova, O.; Glowacki, R.; Sebekova, K.; Bald, E; Gabryelak, T.; Watala, C., "PAMAM G4 dendrimers lower high glucose but do not improve reduced survival in diabetic rats", International Journal of Pharmaceutics, (20080000), vol. 364, doi:doi:10.1016/j.ijpharm.2008.08.001, pp. 142-149, XP025562429.

Li, C.; Liu, H.; Sun, Y.; Wang, H.; Guo, F.; Rao, S.; Deng, J.; Zhang, Y.; Miao, Y.; Guo, C., "PAMAM nanoparticles promote acute lung injury by inducing autophagic cell death through the Akt-TSC2-mTOR signaling pathway.", Journal of Molecular Cell Biology, (20090000), vol. 1, pp. 37-45.

Jones, C. F.; Campbell, R. A.; Brooks, A. E.; Assemi, S.; Tadjiki, S.; Thiagarajan, G.; Mulcock, C.; Neyrich, A. S.; Brooks, B. D., "Cationic PAMAM dendrimers aggressively initiate blood clot formation.", ACS Nano, (20120000), vol. 6, pp. 9900-9910.

Ye, M.; Qian, Y.; Shen, Y.; Hu, H.; Sui, M.; Tang, J., "Facile synthesis and in vivo evaluation of biodegradable dendritic MRI contrast agents", J Mater Chem, (20120000), vol. 22, pp. 14369-14377.

Guillaudeu, S. J.; Fox, M. E.; Haidar, Y. M.; DY, E. E.; Szoka, F. C.; Frechet, J. M. J., "PEGylated dendrimers with core functionality for biological applications.", Bioconjugate chemistry, (20080000), vol. 19, pp. 461-469.

Van Der Poll, D. G.; Kieler-Ferguson, H. M.; Floyd, W. C.; Guillaudeu, S. J.; Jerger, K.; Szoka, F. C.; Frechet, J. M., "Design, synthesis, and biological evaluation of a robust, biodegradable dendrimer.", Bioconjugate Chemistry, (20100000), vol. 21, doi:doi:10.1021/bc900553n, pp. 764-773, XP055358795.

Castanotto, D.; Rossi, J. J., "The promises and pitfalls of RNA-interference-based therapeutics", Nature, (20090000), vol. 457, doi:doi:10.1038/nature07758, pp. 426-433, XP055090044.

Dufes, C.; Uchegbu, I.; Schatzlein, A., "Dendrimers in gene delivery", Adv Drug Deliver Rev, (20050000), vol. 57, doi:doi:10.1016/j.addr.2005.09.017, pp. 2177-2202, XP025283973.

Mintzer, M. A.; Simanek, E. E., "Nonviral vectors for gene delivery", Chemical Reviews, (20090000), vol. 109, doi:doi:10.1021/cr800409e, pp. 259-302, XP055006821.

Biswas, S.; Torchilin, V. P., "Dendrimers for siRNA delivery.", Pharmaceuticals, (20130000), vol. 6, pp. 161-183.

Santos, J. L.; Oliveira, H.; Pandita, D.; Rodrigues, J.; Pego, A. P.; Granja, P. L.; Tomas, H., "Functionalization of poly(amidoamine) dendrimers with hydrophobic chains for improved gene delivery in mesenchymal stem cells", Journal of Controlled Release, (20100000), vol. 144, pp. 55-64, XP027036556.

Thakur, S.; Kesharwani, P.; Tekade, R. K.; Jain, N. K., "Impact of pegylation on biopharmaceutical properties of dendrimers", Polymer, (20150000), vol. 59, doi:doi:10.1016/j.polymer.2014.12.051, pp. 67-92, XP029197818.

Sousa-Herves, A.; Riguera, R.; Fernandez-Megia, E., "PEG-dendritic block copolymers for biomedical applications.", New J. Chem., (20120000), vol. 36, pp. 205-210.

Reyes-Reveles, J.; Sedaghat-Herati, R.; Gilley, D. R; Schaeffer, A. M.; Ghosh, K. C.; Greene, T. D.; Gann, H. E.; Dowler, W. A; KR, "mPEG-PAMAM-G4 Nucleic Acid Nanocomplexes: Enhanced Stability, RNase Protection, and Activity of Splice Switching Oligomer and Poly I:C RNA.", Biomacromolecules, (20130000), vol. 14, pp. 4108-4115.

Barnard, A.; Posocco, P.; Pricl, S.; Calderon, M.; Haag, R.; Hwang, M. E.; Shum, V. W.; Pack, D. W.; Smith, D. K., "Degradable self-assembling dendrons for gene delivery: experimental and theoretical insights into the barriers to cellular uptake", JAm Chem Soc, (20110000), vol. 133, pp. 20288-20300.

Welsh, D. J.; Jones, S. P.; Smith, D. K., "On-off" multivalent recognition: degradable dendrons for temporary high-affinity DNA binding, Angewandte Chemie, International Edition, (20090000), vol. 48, pp. 4047-4051.

Barnard, A.; Calderon, M.; Tschiche, A.; Haag, R.; Smith, D. K., "Effects of a PEG additive on the biomolecular interactions of self-assembled dendron nanostructures.", Organic & biomolecular chemistry, (20120000), vol. 10, pp. 8403-8409.

Barnard, A.; Posocco, P.; Fermeglia, M.; Tschiche, A.; Calderon, M.; Pricl, S.; Smith, D. K., "Double-degradable responsive self-assembled multivalent arrays—temporary nanoscale recognition between dendrons and DNA", Organic & biomolecular chemistry, (20140000), vol. 12, pp. 446-455.

Movellan, J.; Gonzalez-Pastor, R.; Martin-Duque, P.; Sierra, T.; De La Fuente, J. M.; Serrano, J. L., "New Ionic bis-MPA and PAMAM Dendrimers: A Study of Their Biocompatibility and DNA-Complexation", Macromol. Biosci., (20150000), vol. 15, pp. 657-667.

Amaral, S. P.; Fernandez-Villamarin, M.; Correa, J.; Riguera, R.; Fernandez-Megia, E., "Efficient Multigram Synthesis of the Repeating Unit of Gallic Acid-Triethylene Glycol Dendrimers", Org Lett, (20110000), vol. 13, pp. 4522-4525.

Hurrell, S.; Milroy, G. E.; Cameron, R. E., "The degradation of polyglycolide in water and deuterium oxide. Part 1: The effect of reaction rate.", Polymer, (20030000), vol. 44, doi:doi:10.1016/S0032-3861(02)00883-2, pp. 1421-1424, XP004409082.

Fernandez-Megia, E.; Correa, J.; Riguera, R., "Clickable" PEG-dendritic block copolymers., Biomacromolecules, (20060000), vol. 7, doi:doi:10.1021/bm060580d, pp. 3104-3111, XP055122904.

Gary, D. J.; Puri, N.; Won, Y. Y., "Polymer-based siRNA delivery: Perspectives on the fundamental and phenomenological distinctions from polymer-based DNA delivery", Journal of Controlled Release, (20070000), vol. 121, doi:doi:10.1016/j.jconrel.2007.05.021, pp. 64-73, XP022179907.

Mintzer, M. A.; Merkel, O. M.; Kissel, T.; Simanek, E. E., "Polycationic triazine-based dendrimers: effect of peripheral groups on transfection efficiency", New J Chem, (20090000), vol. 33, pp. 1918-1925.

Merkel, O. M.; Mintzer, M. A.; Sitterberg, J.; Bakowsky, U.; Simanek, E. E.; Kissel, T., "Triazine dendrimers as nonviral gene delivery systems: effects of molecular structure on biological activity", Bioconjug Chem, (20090000), vol. 20, doi:doi:10.1021/bc900243r, pp. 1799-1806, XP055382296.

Merkel, O. M.; Mintzer, M. A.; Librizzi, D.; Samsonova, O.; Dicke, T.; Sproat, B.; Garn, H.; Barth, P. J.; Simanek, E. E.; Kissel,, "Triazine dendrimers as nonviral vectors for in vitro and in vivo RNAi: the effects of peripheral groups and core structure on biological activity.", Mol Pharm, (20100000), vol. 7, pp. 969-983.

Fernandez-Villamarin, M.; Sousa-Herves, A.; Porto, S.; Guldris, N.; Martinez-Costas, J.; Riguera, R.; Fernandez-Megia, E., "A Dendrimer-Hydrophobic Interaction Synergy Improves the Stability of Polyion

(56) References Cited

OTHER PUBLICATIONS

Complex Micelles", Polymer Chemistry Accepted Manuscript, The Royal Society of Chemistry, pp. 1-12.

Akin, A.; Giuseppe, B., "Exploiting endocytosis for nanomedicines.", Cold Spring Harbor perspectives in biology, (20130000), p. 1-24.

Merkel, O. M.; Zheng, M.; Mintzer, M. A.; Pavan, G. M.; Librizzi, D.; Maly, M.; Hoffken, H.; Danani, A.; Simanek, E. E.; Kissel, T, "Molecular modeling and in vivo imaging can identify successful flexible triazine dendrimer-based siRNA delivery systems", Journal of controlled release : official journal of the Controlled Release Society, (20110000), vol. 153, pp. 23-33.

Langereis, S.; Lussanet, Q. G. D.; Van Genderen, M. H. P.; Backes, W. H.; Meijer, E. W., "Multivalent contrast agents based on gadolinium-diethylenetriaminepentaacetic acid-terminated poly(propylene imine) dendrimers for magnetic resonance imaging.", Macromolecules, (20040000), vol. 37, doi:doi:10.1021/ma035983+, pp. 3084-3091, XP055386259.

Merkel, O. M.; Beyerle, A.; Beckmann, B. M.; Zheng, M.; Hartmann, R. K.; Stoger, T.; Kissel, T. H., "Polymer-related off-target effects in non-viral siRNA delivery.", Biomaterials, (20110000), vol. 32, pp. 2388-2398.

Beyerle, A.; Irmler, M.; Beckers, J.; Kissel, T.; Stoeger, T., "Toxicity pathway focused gene expression profiling of PEI-based polymers for pulmonary applications", Mol Pharm, (20100000), vol. 7, pp. 727-737.

Mahesh, L. P.; Min, Z.; Oleh, T.; Olga, B. G.; Huixin, H.; Tamara, M., "Internally cationic polyamidoamine PAMAM-OH dendrimers for siRNA delivery: effect of the degree of quaternization and cancer targeting.", Biomacromolecules, (20090000), vol. 10, pp. 258-266.

Erbacher, P.; Roche, A. C.; Monsigny, M.; Midoux, P., "Putative role of chloroquine in gene transfer into a human hepatoma cell line by DNA lactosylated polylysine complexes.", Exp Cell Res, (19960000), vol. 225, doi:doi:10.1006/excr.1996.0169, pp. 186-194, XP002188020.

Ciftci, K.; Levy, R. J., "Enhanced plasmid DNA transfection with lysosomotropic agents in cultured fibroblasts.", Int J Pharm, (20010000), vol. 218, pp. 81-92.

Moreira, C.; Oliveira, H.; Pires, L. R.; Simoes, S.; Barbosa, M. A.; Pego, A. P., "Improving chitosan-mediated gene transfer by the introduction of intracellular buffering moieties into the chitosan backbone.", Acta biomaterialia, (20090000), vol. 5, doi:doi:10.1016/j.actbio.2009.04.021, pp. 2995-3006, XP026625153.

Fernandez-Trillo, F.; Pacheco-Torres, J.; Correa, J.; Ballesteros, P.; Lopez-Larrubia, P.; Cerdan, S.; Riguera, R.; Fernandez-Megi, "Dendritic MRI contrast agents: an efficient prelabeling approach based on CuAAC.", Biomacromolecules, (20110000), vol. 12, doi:doi:10.1021/bm2004466, pp. 2902-2907, XP055407052.

PEG-GATGE
(G2)

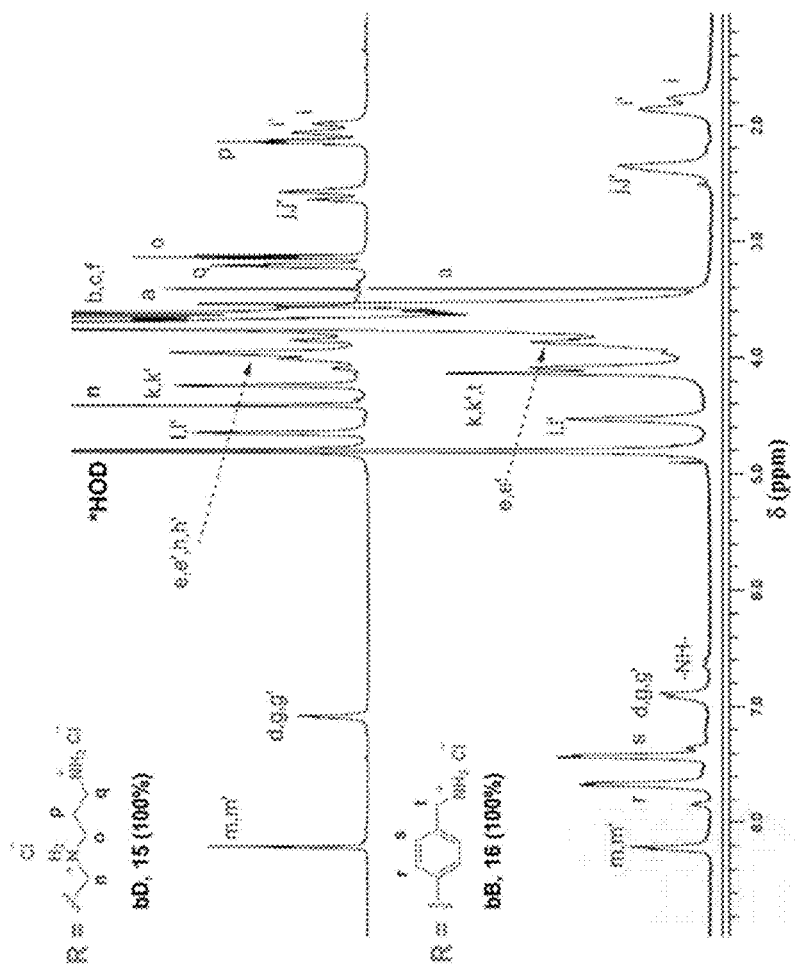
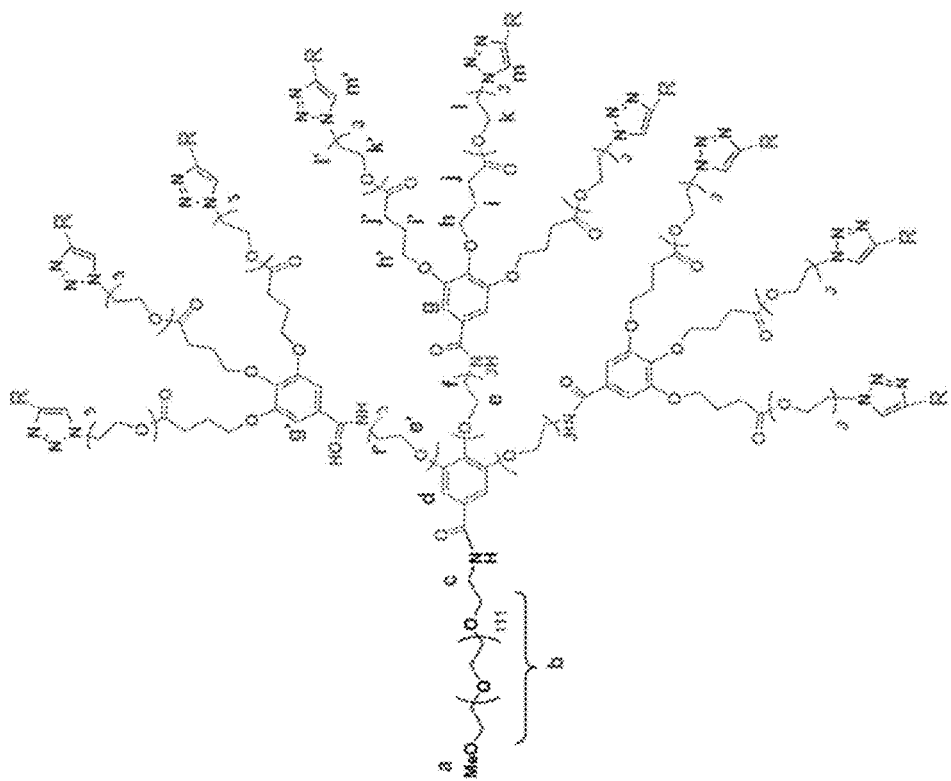
FIG. 3B

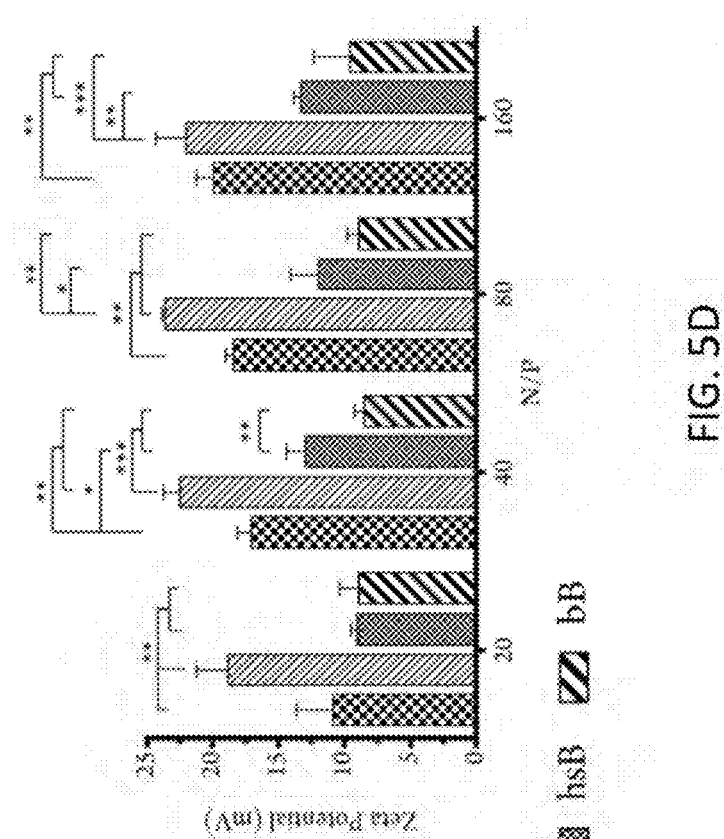
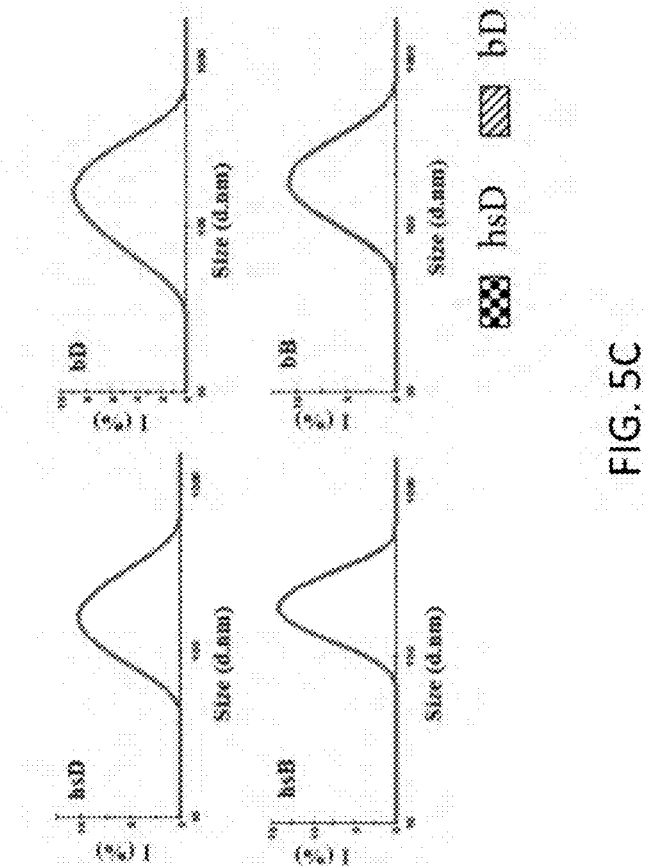
FIG. 5C
FIG. 5D

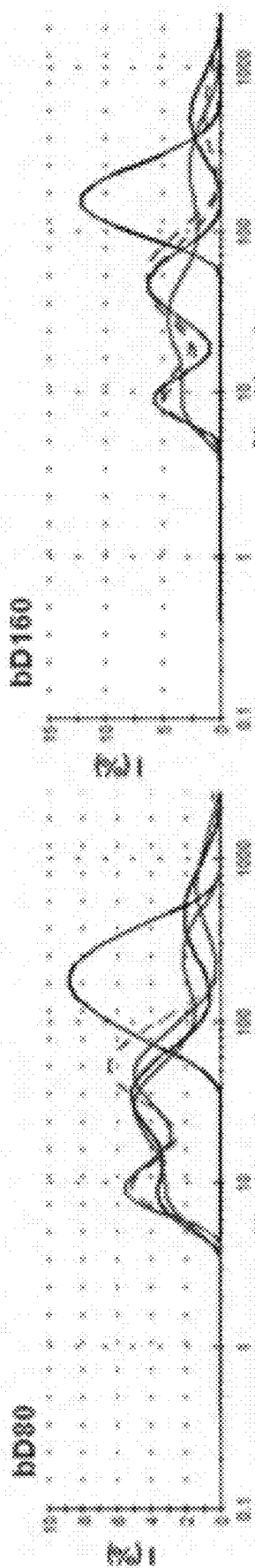
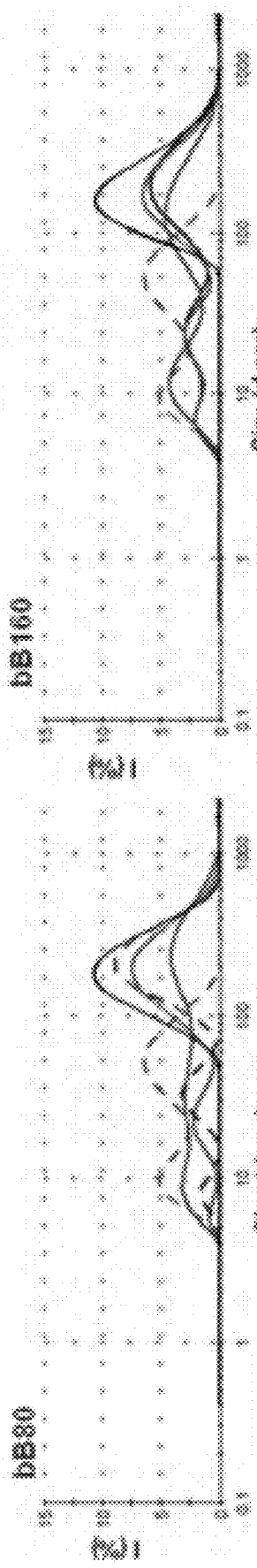
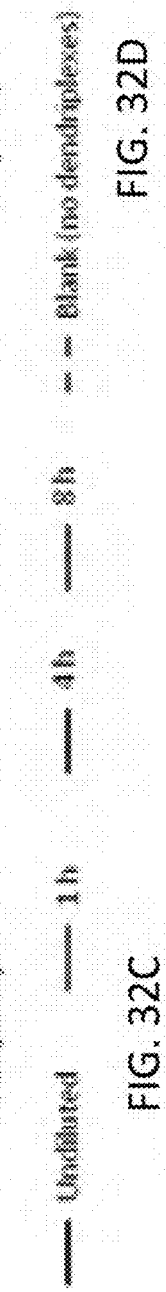
FIG. 32A  FIG. 32B  FIG. 32C  FIG. 32D

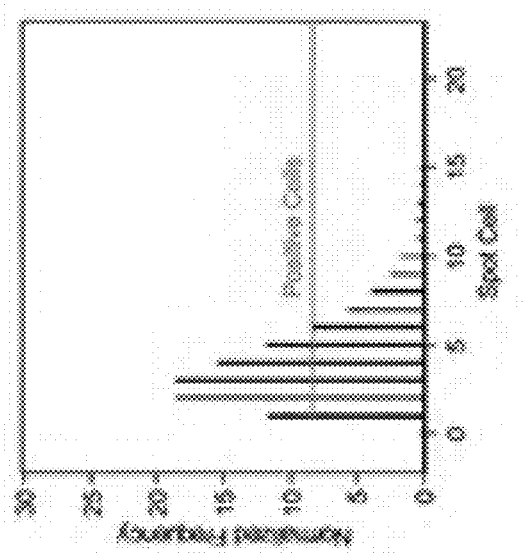
FIG. 36A
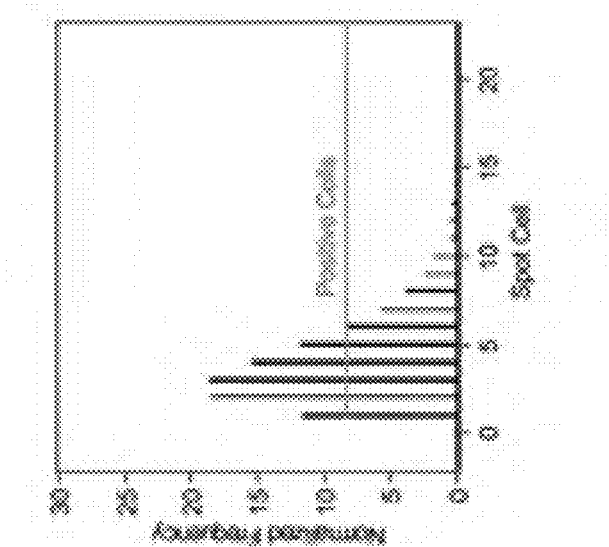
FIG. 36B
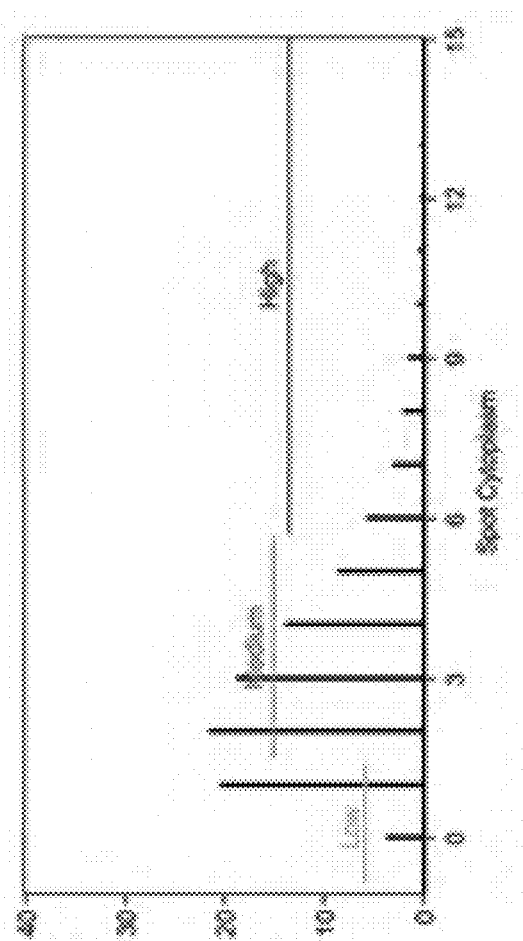
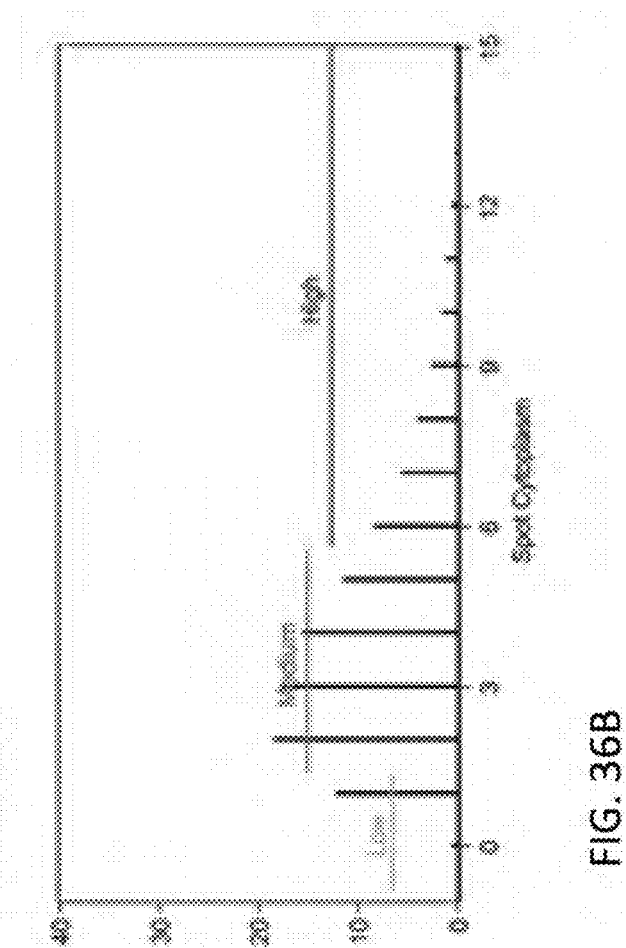

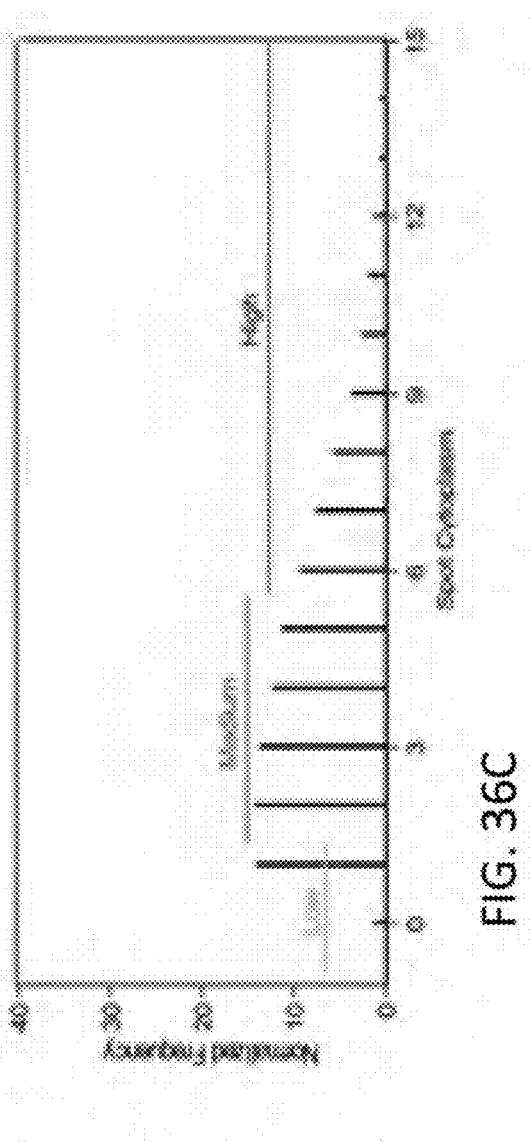
FIG. 36C
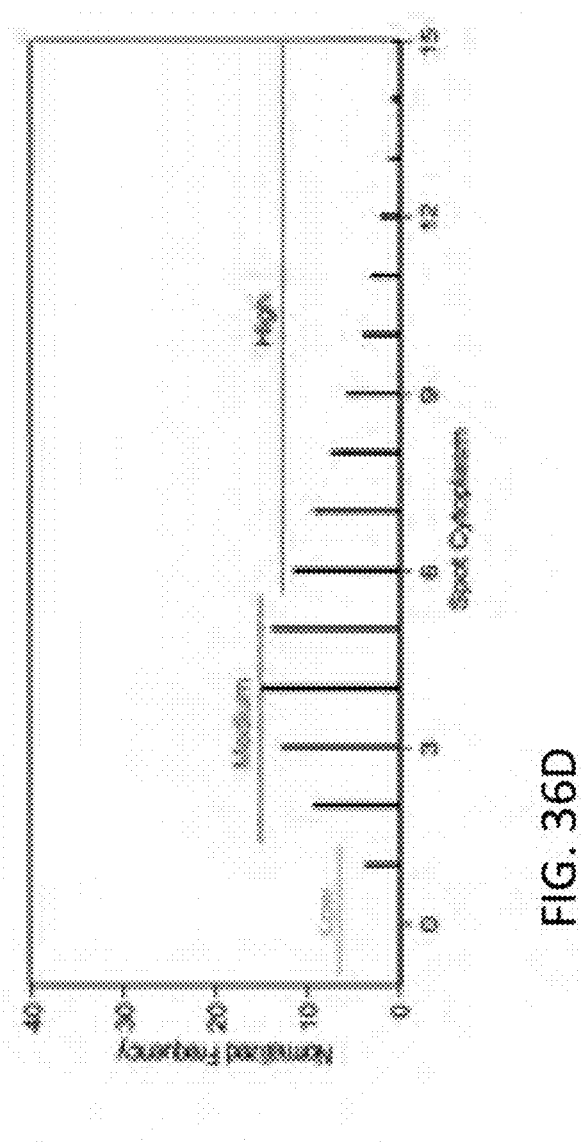
FIG. 36D
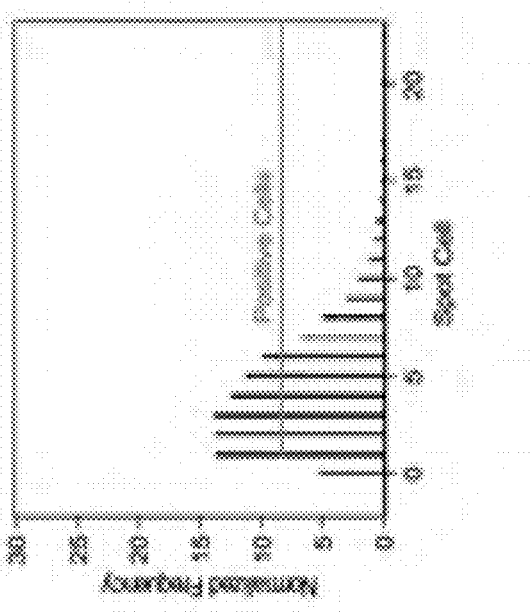
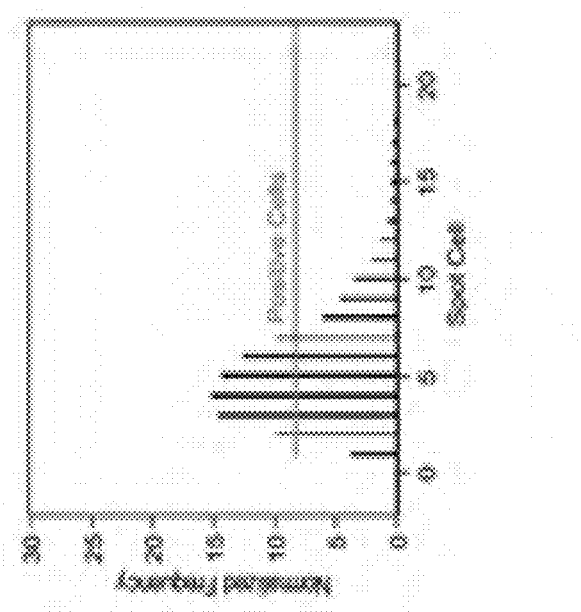

SEQUENCE LISTING

```
<160> NUMBER OF SEQ ID NOS: 1

<210> SEQ ID NO 1
<211> LENGTH: 25
<212> TYPE: RNA
<213> ORGANISM: Artificial Sequence
<220> FEATURE:
```

<223> OTHER INFORMATION: synthetic construct

<400> SEQUENCE: 1
gcugacccug aaguucaucu gcacc                      25

BIODEGRADABLE DENDRITIC STRUCTURE, METHODS AND USES THEREOF

CROSS-REFERENCE TO RELATED PATENT APPLICATIONS

This application is a U.S. National Stage Application under 35 U.S.C. § 371 of International Patent Application No. PCT/IB2017/053047, filed May 23, 2017, which claims priority to Portugal Application No. 109408, filed May 23, 2016, both of which are hereby incorporated by reference in their respective entireties as if set forth herein.

TECHNICAL FIELD

The present disclosure relates to biodegradable and biocompatible dendritic repeating unit/scaffold (bRU), to a method of synthesis of biodegradable and biocompatible dendritic repeating unit/scaffold (bRU) and to the biomedical applications of biodegradable and biocompatible dendritic repeating unit/scaffold (bRU). This bRU is useful as scaffold to synthesize fully biodegradable dendrimers and/or "mix" or "hybrid" biodegradable dendrimers, presenting a biodegradable shell and a hydrolytically stable/non-degradable core of already existing dendritic systems.

The disclosure described herein also relates to the synthesis of a hybrid and fully biodegradable, biocompatible and non-toxic families of PEG-dendritic block copolymers based on bRU, as well as their functionalization with different amine moieties. This example of amine-functionalization allowed to complex siRNA and, therefore, to explore their functionality assessment as vectors of this nucleic acid.

The development of biodegradable dendritic structures is envisaged as a way to prevent or avoid cytotoxicity derived from the accumulation of non-degradable synthetic materials into the cells and/or tissues. Moreover, biodegradable dendritic structures are also put forward in the context of the design of "smart" controlled delivery systems in which one aims at triggering and/or sustaining the release of a therapeutic agent via the control of the degradation profile of its vector.

BACKGROUND

Dendritic nanostructures are considered promising vehicles for different bioactive molecules due to unique structural features: globular, well defined and highly branched structure, low polydispersity and tunable size.[1] The presence of chemical handles on the dendritic periphery further allows their functionalization with ligands and/or drugs in a specific and controlled manner to mimic the multivalency present in many biological systems. Additionally, dendrimers can also cargo different bioactives (as nucleic acids(NA), different types of chemical drugs, proteins, growth factors) by forming nanosized and compact structures stabilized by non-covalent interactions.

Despite the progress in the design and use of dendritic structures with improved features for biomedical applications, most currently used dendritic families are non-degradable under physiological conditions, which might result in cytotoxicity induced by accumulation of non-degradable synthetic materials inside cells or in tissues.[2] To overcome these hurdles, a number of teams are focusing on the design of biodegradable dendritic structures.[3] Indeed, biodegradable materials that under physiological conditions degrade with time into smaller fragments (which can be excreted or eliminated through metabolic pathways) are expected to overcome the risk of complications associated with the long-term presence in tissues of non-degradable synthetic materials.[4] Also, some authors have proposed the use of degradable dendritic structures as macromolecular contrasting agents that can overcome long-term Gd(III) tissue accumulation.[5] Additionally, the development of biodegradable dendrimers is also put forward in the context of the design of "smart" controlled delivery systems in which one aims at triggering and/or sustaining the therapeutic agent release via the control of its vector degradation profile. However, the preparation of biodegradable nanocarriers is challenging because of undesired backbone degradation during synthesis, purification, and subsequent functionalization and processing steps.[6] This explains the still reduced number of publications on biodegradable dendrimers reported for specific functions in biomedicine,[3] as well as the reduced patent applications (CN103055328, WO2005003260).[5a,7] Recently, Jianbin, T et al. have disclosed a degradable dendritic macromolecule magnetic resonance contrast agent and a preparation method thereof (CN103055328).[5a] Also, Leinweber, D. et al. have shown the use of alkoxylated dendrimers as biodegradable demulsifiers for breaking oil/water emulsions (WO2005003260).[7] However, this is not a biomedical application. Therefore, biodegradable dendritic structures are still awaited.

GENERAL DESCRIPTION

Here, it is disclosed a new biodegradable dendritic structure, namely a biocompatible and azide-terminated GATGE dendritic repeating unit, based on a gallic acid (GA) core and triethylene glycol (TG) butanoate arms, incorporating biodegradable ester bonds (E) at the dendritic branches.

Recently, C. Tyler and V. Zubkova reported compounds that are useful for the preparation of non-biodegradable dendrimers, the use of these compounds for preparing dendrimers and processes for preparing the compounds (WO2014084743, US2015291522).[8] The present disclosure presents biodegradability as a substantial novelty and advantage comparing to these compounds. Therefore, the GATGE unit is useful as building unit/scaffold in order to synthesize "mix" or "hybrid" biodegradable dendrimers and/or fully biodegradable dendrimers (fbGATGE dendrimers). The "hybrid" dendrimers will comprise a biodegradable shell with a non-biodegradable and resistant core of already existing dendritic systems (such as poly(amido amine) (PAMAM), poly(propylene imine) (PPI), poly(L-lysine) (PLL), GATG (Gallic Acid Triethylene Glycol) dendrimers, among other). While the fully biodegradable GATGE dendritic systems, will consist of completely biodegradable components/layers, in particular from core to shell.

Both, hybrid and fully, biodegradable GATGE dendritic structures presented here present peripheral azides, which are easily functionalizable by means of the Cu(I)-catalyzed Huisgen cycloaddition (CuAAC, click chemistry) with a great variety of ligands, therefore these new biodegradable GATGE-based dendritic nanomaterials are easily tunable to act as versatile vectors for different biomedical applications.

The present disclosure relates to a GATGE repeating unit, will be described in detail bellow.

Another aspect of the present disclosure describes a new family of PEG-GATGE dendritic block copolymers. They were synthesized from GATGE building units and their biofunctionality assessed as non-viral vectors of nucleic acids in gene therapy applications. Among these strategies to modulate gene expression, the down-regulation of protein production via RNA interference (RNAi) mediated by small interfering RNA (siRNA) has proven good therapeutic potential in clinical settings.[9] However, despite its early success, the widespread use of RNAi therapeutics requires the development of clinically suitable, safe and effective delivery carriers with the ability to compact and protect naked siRNA.

Most of the siRNA non-viral carriers tested so far have been mainly based on cationic systems previously developed for the delivery of plasmid DNA (pDNA), such as cell penetrating peptides, lipids, natural and synthetic polymers, and more recently, dendrimers. Cationic PAMAM, PPI and PLL dendrimers, among others, have been reported as promising carriers of pDNA and siRNA.[10] A common approach for masking the characteristic positive charge of the resulting dendriplexes (dendrimer-NA complexes), and improving their biocompatibility and circulation time in the blood stream has been the tethering of poly(ethylene glycol) (PEG) chains.[11] PEG-dendritic block copolymers are obtained when PEGylation is performed at the focal point of dendrimers.[12] Several research groups, have reported on the use of PEG-dendritic block copolymers for the delivery of pDNA. The same strategy with siRNA has not been described until very recently with a fourth generation (G4) PEG-PAMAM.[13]

However, in the area of NA delivery, as occurs in the biomedical field in general, the dendritic families used are non-biodegradable. The only biodegradable cases are restricted to rare examples with amine-terminated bis-HMPA [2,2-bis(hydroxymethyl)propanoic acid] dendrons for the encapsulation of DNA.[14,15]. The challenge associated to combine in the same structure unprotected primary/secondary amine groups—needed to get the cationic charge to complex NAs—with hydrolyzable (and so, electrophilic) bonds adds extra strain to the already difficult task of engineering biodegradable dendritic vectors.

In an embodiment, to demonstrate the use and application of the GATGE repeating unit now disclosed, it were developed a hybrid and a fully biodegradable, biocompatible, non-toxic and PEGylated dendritic system, named PEG-GATGE and PEG-fbGATGE (FIGS. 1A-1B). PEG-GATGE was synthesized until generation 2 (G2), while three generations (G1, G2 and G3) were synthesized for the fully biodegradable PEG-fbGATGE. Moreover, as a further example, the suitability of these GATGE-based nanomaterials as efficient vectors of siRNA is provided, including a low cytotoxicity profile, and the abilities to protect siRNA from endonuclease degradation and transfect mammalian cells. Surprisingly, the ester linkages in GATGE ensure a more effective siRNA release from the dendriplexes (dendrimer-siRNA complexes) and hence, increased transfection efficiency/silencing compared to the homologous hydrolytically stable PEG-GATG copolymers. Moreover, PEG-GATGE and PEG-fbGATGE represent the first examples of biodegradable ester-based PEG-dendritic block copolymers developed for gene therapy applications.

GATGE is a biodegradable and biocompatible azide-terminated dendritic repeating unit, based on a gallic acid (GA) core and triethylene glycol (TG) butanoate arms. The novelty relies on their biodegradability trait due to the presence of ester bonds (E) localized at the dendritic branches. This biodegradable repeating unit is useful as building unit/scaffold in order to synthesize "hybrid" biodegradable dendrimers (FIG. 1A), and/or to synthesize fully biodegradable dendrimers (fbGATGE dendrimers) (FIG. 1B). "Hybrid" dendrimers will consist of a resistant core of other dendritic systems (such as PAMAM, PPI, GATG, among other) (GATG case described in detail below) and a biodegradable shell. While in the fully biodegradable GATGE dendritic systems, all their building units are GATGE units susceptible to hydrolysis, therefore, they will present a fully biodegradable trait. Both types of GATGE dendritic systems may present peripheral azide groups that allow their efficient and easy decoration by means of CuAAC with a great variety of ligands. This possibility of functionalization makes these dendrimers into suitable nanocarriers for different biomedical applications.

In an embodiment, biodegradable, biocompatible and non-toxic PEG-GATGE dendritic block copolymers of generation 2 were synthesized, consisting of a hydrolytically stable GATG core and a biodegradable GATGE shell.

In an embodiment, fully biodegradable, biocompatible and non-toxic PEG-fbGATGE dendritic block copolymers of generation 1, 2 and 3 were synthesized, which are completely based on biodegradable GATGE units.

In both cases, a chain of PEG of 5 kDa (PEG of 10 KDa in examples 24 and 25) was attached at the focal point of the dendritic block, with the aim of obtaining dendritic vectors with lower toxicity, enhanced solubility and longer circulation times. In other embodiment, the attachment of a PEG chain may imply the introduction of a new possible point of functionalization that will allow the tethering of the target moieties to the copolymers while assuring their exposure at the surface of the corresponding dendritic nano particle.

In an embodiment, the previously mentioned challenge that supposes to combine in the same structure unprotected primary/secondary amine groups with hydrolyzable (and so, electrophilic) ester bonds was surpassed by the methodology described herein, since: i) the growth of the dendritic parts/blocks was successfully achieved via amide linkages, which required unprotected amine as terminal functional groups of each generation to obtain the next one by selective attack to the (electrophilic) focal point (carboxylic acid) of the GATGE building units and not to their ester linkages, and ii) the surface functionalization of these biodegradable dendritic nanomaterials by CuAAC with unprotected alkynated amines was successfully achieved (quantitative yields). The presence and/or introduction of unprotected amine groups suppose a great advantage, since no protection/deprotection steps are needed.

In an embodiment, the amine-functionalization allowed exploring the function of PEG-GATGE as vectors of NAs as an example of their biofunctionality. The preliminary studies with the hydrolytically stable PEG-GATG copolymers counterparts for siRNA delivery resulted in very limited internalization efficiency with only a 23% of positive cells (data not shown), probably related to a deficient stability of the dendriplexes. In the present disclosure, it is demonstrated that after CuAAC functionalization with alkynated 1,3-propylenediamine (13) and benzylamine (14) ligands (FIG. 3A), cationic PEG-GATGE copolymers enable the efficient complexation of siRNA and its delivery into cells. The use of the diamine (13) aims to boost the dendrimer-siRNA binding strength by increasing the positive multivalency. The use of benzylamine (14) seeks to increase further the hydrophobicity of the system. The extra hydrophobic character of the GATGE building unit due to the butanoate spacer confers to these hydrolyzable dendritic systems a great ability to complex, protect and mediate the cellular internalization of siRNA. Moreover, the localization of the degradation points at the dendritic periphery, close to the complexed siRNA, was found crucial for the nucleic acid release from the nanoparticles compared to their hydrolytically stable PEG-GATG copolymer counterparts.

In an embodiment to better results, regarding this biodegradability aspect, the GATGE-based dendritic nanomaterials present an improved degradation profile. These new dendritic structures are stable enough to allow the bioactive transport, to degrade in a certain percentage favouring its release, while breaking into smaller fragments after accomplishing their biological function. This results in their clearance, avoiding long-term accumulation, especially important for in vivo applications. Biodegradable dendritic architectures incorporating GATGE building units, have a great potential in the biomedical field, since as shown with alkynated amines, the presence of peripheral azides on their surface will allow an efficient and easy decoration by means of CuAAC with alternative functional groups and ligands:

a) positive or negative charged groups. To link amines or carboxylic acid moieties (e.g. pentinoic or benzoic acid) allows complexing proteins as growth factors (e.g. BDNF), and explore bGATGE as carriers for regenerative goals.

b) hydrophobic groups, as cholesterol or aliphatic chains, will allow encapsulating lipophilic/insoluble drugs and using these dendrimers as drug delivery vectors.

c) contrast agents (e.g. Gd(III)-DTPA, Gd(III)-DOTA, Gd(III)-DO3A) for exploring their use as biodegradable dendritic MRI contrast agents for diagnosis purposes.

Therefore, the combination in one scaffold of hydrophilia (triethylene glycol), hydrophobia (gallic acid and butanoate spacer), biodegradability trait (ester bonds) and possibility of functionalization (peripheral azides) confers a great versatility/functionality to GATGE building unit. Thus, GATGE dendritic structures are versatile and suitable nanocarriers not only for nucleic acid delivery, but also for broader applications in drug delivery, diagnosis, vaccines, tissue engineering, among others, finally leading to new strategies for nanomedicine.

The present disclosure relates to a new biodegradable, biocompatible and azide-terminated GATGE dendritic repeating unit, based on a gallic acid (GA) core and triethylene glycol (TG) butanoate arms, incorporating biodegradable ester bonds (E) at the dendritic branches. The present disclosure also relates to the corresponding biodegradable, biocompatible and azide-terminated PEG-GATGE dendritic block copolymer.

This disclosure also relates to the process of synthesis and characterization of biodegradable and biocompatible dendritic repeating unit/scaffold (bRU). As well as the process of synthesis and characterization of the partially and fully biodegradable, and biocompatible PEG-dendritic block copolymers based on bRU.

Furthermore, the present disclosure also provides examples of biomedical application of the biodegradable and biocompatible dendritic structures. bRU is useful as scaffold to synthesize "mix" or "hybrid" biodegradable dendrimers, presenting a biodegradable shell and a hydrolytically stable/non-degradable core of already existing dendritic systems, and also to synthesize fully biodegradable dendrimers, which component or layers (core, intermediate layers and shell) are completely biodegradable.

The GATGE-based dendritic structures present biodegradability as great advantage comparing to other compounds which are non-biodegradable. The GATGE unit is useful as a building unit/scaffold in order to obtain "mix" or "hybrid" biodegradable dendrimers. These "hybrid" dendrimers will consist of a biodegradable shell with a non-biodegradable and resistant core of already existing dendritic systems (such as poly(amido amine) (PAMAM), poly (propylene imine) (PPI), poly(L-lysine) (PLL), GATG (Gallic Acid Triethylene Glycol) dendrimers, among other); and/or to synthesize fully biodegradable dendrimers (fb-GATGE dendrimers), which will consist of completely biodegradable components/layers (from core to shell). Both hybrid and fully biodegradable GATGE-based dendritic systems present peripheral azides, which are easily functionalizable by means of the Cu(I)-catalyzed Huisgen cycloaddition (CuAAC, click chemistry) with a great variety of ligands, therefore these new biodegradable GATGE-based dendritic nanomaterials are easily tunable to act as versatile vectors for different biomedical applications.

The present disclosure relates to a biodegradable dendritic structure comprising G dendritic generations and a polyalkylene polyol linked to a focal point of the dendritic structure, wherein at least one generation comprises:

an organic acid; a polyether group and an ester group,
wherein the $1^{st}$ dendritic generation comprises the organic acid linked to the polyalkylene polyol and to polyether group and
at least a further dendritic generation comprising a further organic acid linked to the polyether group of a previous generation and to a spacer chain wherein said spacer chain comprises at least one ester group.

In an embodiment, the $1^{st}$ dendritic generation comprises the organic acid may be linked to the polyalkylene polyol and to 3 polyether groups and the further dendritic generation may comprise 3 spacers chains, wherein each spacer is linked to the organic acid.

In an embodiment, the $1^{st}$ dendritic generation may further comprise a spacer chain wherein said spacer chain comprises at least one ester group.

In an embodiment, the spacer chain may be selected from an ethanoate, propanoate, butanoate, pentanoate, hexanoate, heptanoate or mixtures thereof, in particular one generation of dendritic structure may comprise a butanoate, in particular 2-(2-ethoxyethoxy)ethyl butyrate.

In an embodiment, the G dendritic generation may be a $2^{nd}$-$4^{th}$ dendritic generation, preferably a $2^{nd}$-$3^{rd}$ dendritic generation.

In an embodiment, the ester of the spacer chain may be further linked, in its end, to a functional group selected from a list consisting of: an amine, an azide, an hydroxyl groups, thiol groups, a carboxyl, an alkene, or an alkyne group.

In an embodiment, the ester of the spacer chain may be further linked to the organic acid of the $2^{nd}$, $3^{rd}$ or further generation, wherein said link comprises a functional group selected of a list consisting of: amine, a hydroxyl, or a thiol group.

In an embodiment, the amine group may be a propylenediamine group, a benzylamine group, or other alkylene polyamines, a aromatic amine, a guanidinium group, a tertiary amine, an imidazole, a histidine, or mixtures thereof.

In an embodiment, the organic acid may be 3,5-dihydroxybenzoic acid, 3,4-dihydroxybenzoic acid, 2,4,6-trihydroxybenzoic, gallic acid and derivatives thereof, in particular is gallic acid.

In an embodiment, the polyether group may be selected from the following list: ethylene glycol, diethylene glycol, triethylene glycol, tetraethylene gylcol, pentaethylene glycol, or mixtures thereof, preferably triethylene glycol.

In an embodiment, the polyalkylene polyol may be selected from the following list: polyethylene glycol, polypropylene glycol, mixtures thereof, preferably polyethylene glycol.

In an embodiment, the polyalkylene polyol may contain in its other end an amine group, a hydroxyl group, a thiol group, a carboxylic acid, an azide, an alkyne, an alkene.

In an embodiment, the polyethylene glycol may comprise a molecular weight between 2000-15000 g/mol, in particular 2000-10000 g/mol.

In an embodiment, the biodegradable dendritic structure may further comprise a ligand.

In an embodiment, the biodegradable dendritic structure further may comprise a targeting ligand, wherein said ligand is a hydrophobic group—aliphatic chain, aromatic group—a fluorescent tag, a chemical drug or a contrast agent, or a biomolecule, in particular a peptide, a protein, a monosaccharide, a polysaccharide, an antibody, an aptamer, a glycosaminoglycan, an agent that facilitates receptor recognition, an internalization agent, an nucleus localization agent, or mixtures thereof.

In an embodiment, the biomolecule may be a nucleic acid, a drug, a protein, a growth factor, in particular SiRNA.

In an embodiment, the targeting ligand may be an biomolecule, in particular a peptide, a protein, a polysaccharide, an antibody, a glycosaminoglycan, an agent that facilitates receptor recognition, an internalization agent, escape of the biomolecule from cell endosome, and biomolecule release, an stabilization agent or mixtures thereof.

In an embodiment, the targeting ligand and/or the ligand may be bound to the dendritic structure branch or to the polyalkylene polyol.

Therefore, the biodegradable dendritic structure now disclosed is a biodegradable dendritic structure of formula I:

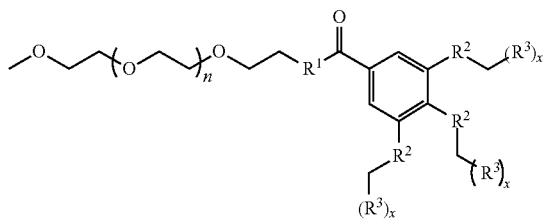

wherein
n is between 40-350;
x is between 0-4;
$R^1$ is selected from NH, O, or S;
$R^2$ is selected from

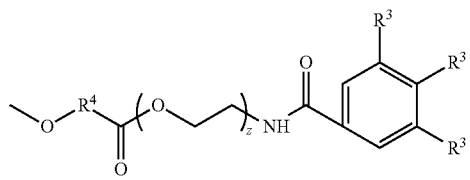

or

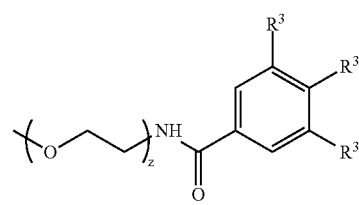

z is between 1-9;
$R^3$ is $R^2$ with the proviso that at a dendritic structure end $R^3$ is

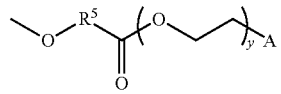

wherein A is selected from an amine group, an amide group, an azide group, a hydroxyl group, a thiol group, a carboxyl group, an isocyanate, an alkene, or an alkyne group;
y is between 1-9;
$R^4$ or $R^5$ is a $C_1$-$C_6$ alkyl chain;
A, $R^1$, $R^2$, $R^3$, $R^4$, $R^5$, n, x, y and z are independently selected from each other.

In an embodiment, n may be 45-250, preferably 70-150, more preferably 90-120.

In an embodiment, x may be between 1-4, preferably 1-3, more preferably 1-2.

In an embodiment, y may be between 2-7, preferably 2-5, more preferably 3-4.

In an embodiment, z may be between 2-7, preferably 2-5, more preferably 3-4.

In an embodiment, $R^4$ or $R^5$ is $C_2$-$C_5$ alkyl chain, $C_3$-$C_4$ alkyl chain.

In an embodiment A may be an amine group wherein the amine group is an 1,3-propylenediamine group, 1,2-ethylenediamine groups or other alkylene polyamines, a benzylamine group, or other aromatic amine groups, a guanidinium group, a tertiary amine, an imidazole, a histidine or mixtures thereof.

In an embodiment, the biodegradable dendritic structure now disclose may further comprise an amine group, a hydroxyl group, a thiol group, a carboxylic acid, an isocyanate, an azide, an alkyne, a cyclooctin, an alkene, an acrylate, wherein said group replaces the $OCH_3$ group.

In an embodiment, the biodegradable dendritic structure may comprise a molecular weight between 2500-75000 g/mol, in particular 2500-25000 g/mol or 2500-27000 g/mol.

In an embodiment, the biodegradable dendritic structure may further comprising a ligand, wherein said ligand is a hydrophobic group, an aliphatic chain, an aromatic group, a fluorescent tag, a chemical drug, a contrast agent, an escaping cell endosomal biomolecule, an nucleus localization agent, and biomolecule release, an stabilization agent, or a biomolecule.

In an embodiment, the ligand is selected 1,3-propylene diamine, benzylamine, benzoic acid, cholesterol, 2,2',2"-(10-(2-(methylamino)-2-oxoethyl)-1,4,7,10-tetraazacyclododecane-1,4,7-triyl)-triacetate gadolinium (III) complex, or mixtures thereof.

In an embodiment, the biodegradable dendritic structure may comprise a biomolecule as a ligand wherein the biomolecule is a protein, a growth factor, a nucleic acid in particular siRNA.

In an embodiment, the biodegradable dendritic structure may further comprise a targeting ligand, wherein said targeting ligand is a biomolecule, in particular a peptide, a protein, a polysaccharide, a antibody, an aptamer, a glycosaminoglycan, an agent that facilitates receptor recognition, an internalization agent, or mixtures thereof.

In an embodiment, the targeting ligand and/or the ligand are/is bound to the biodegradable dendritic structure.

In an embodiment, the biodegradable dendritic structure may be the compound n.5, n.9, n.10, n. 11, n. 12, n. 15, n. 16, n. 17, n.18, n. 21, n. 22, n. 23, n. 24, n. 24, or n. 25.

In an embodiment, the biodegradable dendritic structure according to any of the previous claims for use in medicine.

This disclosure also relates to the biodegradable dendritic structure for use in medicine, in particular for use in the treatment or prevention of cancer.

In an embodiment, the biodegradable dendritic structure may be for use in nucleic acid delivery, in drug delivery, or regenerative medicine or gene therapy.

In an embodiment, the biodegradable dendritic structure may be for use as an imaging agent, namely for, radiotherapy or phototherapy.

This disclosure also relates to a pharmaceutical composition comprising a biodegradable dendritic structure as herein defined and a pharmaceutical acceptable carrier, adjuvant, excipient or mixtures thereof.

In an embodiment, the pharmaceutical composition may be administered via topical, oral, parenteral or injectable. Furthermore, this disclosure also concerns a vaccine comprising the biodegradable dendritic structure herein disclosed.

The disclosure also relates to the use of the biodegradable dendritic structure now disclosed as a carrier for administering a drug and/or a diagnostic agent or the use as an imaging agent, namely for magnetic resonance imaging or computed tomography.

BRIEF DESCRIPTION OF THE DRAWINGS

The following figures provide preferred embodiments for illustrating the description and should not be seen as limiting the scope of invention.

FIGS. 3A-3C—Structures of alkynated propylenediamine (13) and benzylamine (14) ligands (FIG. 3A). Structures and $^1$H NMR spectra (400 MHz, $D_2O$) of amine-terminated bD (15) and bB (16) (FIG. 3B). Structures of hydrolytically stable hsD (19) and hsB (20) (FIG. 3C).

FIGS. 5A-5E—Size distribution of siRNAmi dendriplexes measured by DLS at different N/P ratios (n=3, ±SD). Significant differences between N/P's: bD 40 vs. bD 160 ($p<0.05$) (FIG. 5A). Polydispersity index (PdI) of siRNAmi dendriplexes measured by DLS at different N/P ratios (n=3, ±SD). No significant differences between N/P's (FIG. 5B). Representative size siRNAmi dendriplexes (N/P 80) measurements using DLS: hsD (Z-Average: 141 nm: 0.38); bD (Z-Average: 134 nm: 0.38); hsB (Z-Average: 168 nm: 0.24); bAr (Z-Average: 163 nm: 0.26) (FIG. 5C). Potential zeta values for all developed dendriplexes at different N/P ratios. Significant differences between N/P's: bD 20 vs. bD 80 ($p<0.05$), hsD 20 vs. hsD 40/80/160 ($p<0.01$), hsB 20 vs. hsB 160 ($p<0.01$) (FIG. 5D). TEM images for siRNAmi dendriplexes at N/P 80 and 160: hsD, hsB, bD, and bB (FIG. 5E). Significant differences: *$p<0.05$, $p<0.01$ and *$p<0.001$.

FIG. 8A: Flow cytometry characterization at different N/Ps. Highlighted area corresponds to populations of cells with high relative FL. FIG. 8B: Extended Depth of Field images acquired by imaging flow cytometry for Cy5-siRNAmi bB dendriplexes at N/P160 (red). Gray background: bright field images; Black background: channel 5 images (Cy-5). Scale bar: 10 μm. Representative images for every category are shown: Low spot count, Medium Spot Count, and High spot count. FIG. 8C: Confocal microscopy images for bD and bB at N/P 160. Nuclei stained with Hoechst 33342 (in blue). Cells expressing eGFPLuc (in green). Cy5-siRNAmi dendriplexes (in red).

FIGS. 32A-32D—Stability of the Dendriplexes in different media. Stability of biodegradable dendriplexes in 1×PBS with 20% fetal bovine serum (FBS). FIG. 32A: bD (N/P 80); FIG. 32B: bD (N/P 160);

FIG. 32C: bB (N/P 80); FIG. 32D: bB (N/P 160). Dendriplexes were formed at N/P 80 and 160, diluted 2-fold in PBS+20% FBS, and incubated for 1 h (red), 4 h (blue) and 8 h (brown), at 37° C. Average size was then determined by DLS. Profile of PBS with FBS and no dendriplexes (Blank curve, in green) was taken in order to distinguish protein-related aggregates.

FIG. 33A—top left: bD (N/P 80); FIG. 33A—top right: bD (N/P 160); FIG. 33A—bottom left: bB (N/P 80); FIG. 33A—bottom right: bB (N/P 160); FIG. 33B—top left: bD (N/P 80); FIG. 33B—top right: bD (N/P 160); FIG. 33B—bottom left: bB (N/P 80); FIG. 33B—bottom right: bB (N/P 160). Dendriplexes were formed at N/P 80 and 160, diluted 2-fold in 10 mM NaOAc+137 mM NaCl pH 5.0 and 1×PBS pH 7.4, and incubated for 1 h (blue), 4 h (green) and 8 h (brown), at 37° C. Average size was then determined by DLS. Red curves represent the undiluted dendriplexes.

FIGS. 36A-36D—Dendriplex-loaded vesicles (DLV) per cell. hsD (FIG. 36A), hsB (FIG. 36B), bD (FIG. 36C), bB (FIG. 36D). Left column: Spot count for the cell mask. Right column: Spot count for the cytoplasm mask. Positive cells: region for Cy-5 positive cells (membrane and cytoplasm); Low: region for low spot count cell (cytoplasm); Medium: region for medium spot count cells (cytoplasm); High: region for high spot count cells (cytoplasm).

DETAILED DESCRIPTION

In an embodiment, the design, synthesis and characterization of biodegradable GATGE repeating unit was performed as follows. The synthesis of the GATGE unit 5 comprising a gallic acid core and triethylene glycol-aliphatic ester arms is shown in FIG. 2A.

Figure 2A:
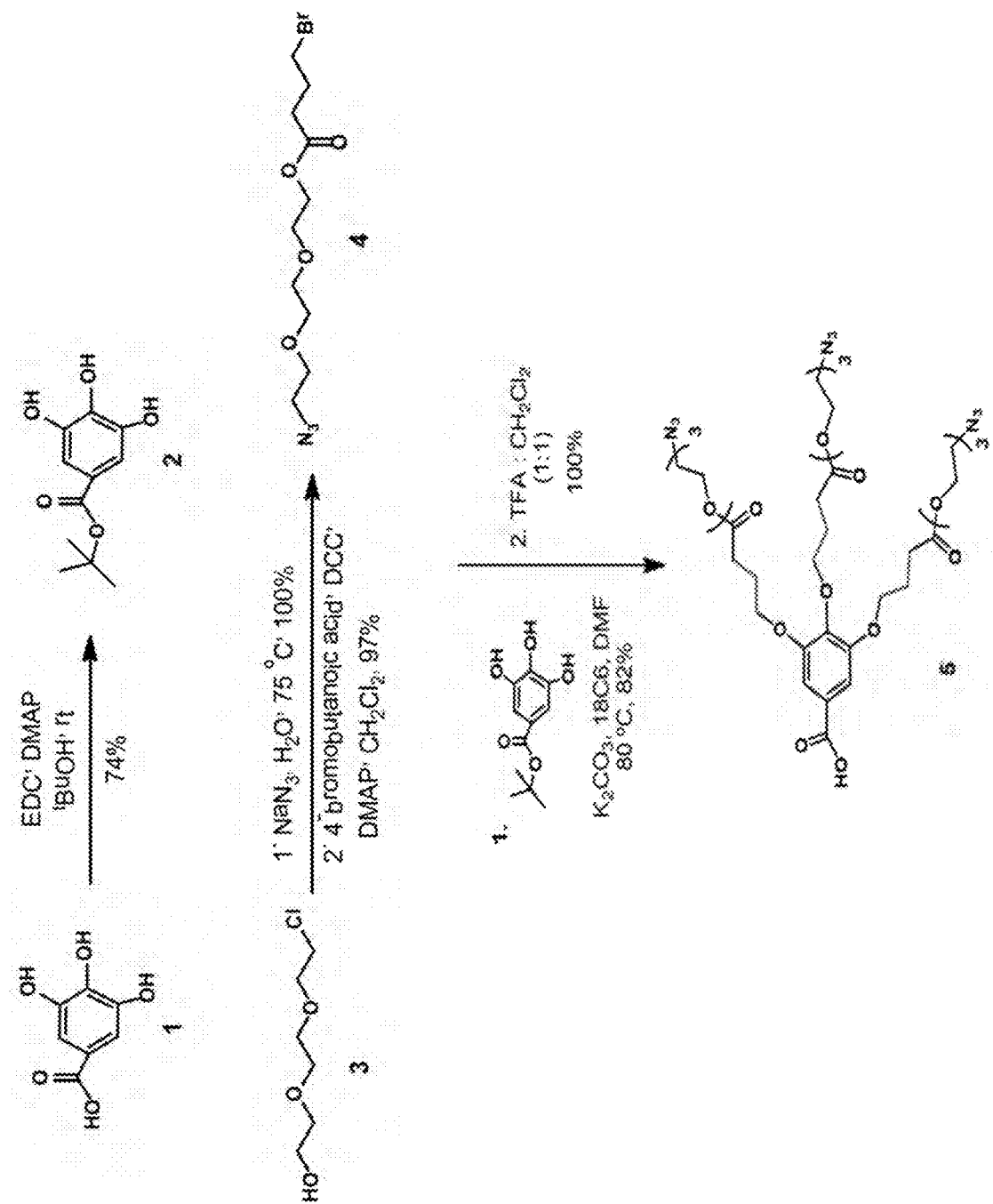
FIGS. 2A-2B—Synthesis of biodegradable GATGE repeating unit 5 (FIG. 2A). Kinetics of the ester hydrolysis in unit 6 by $^1$H NMR at different pD (FIG. 2B).
Figure 2B:
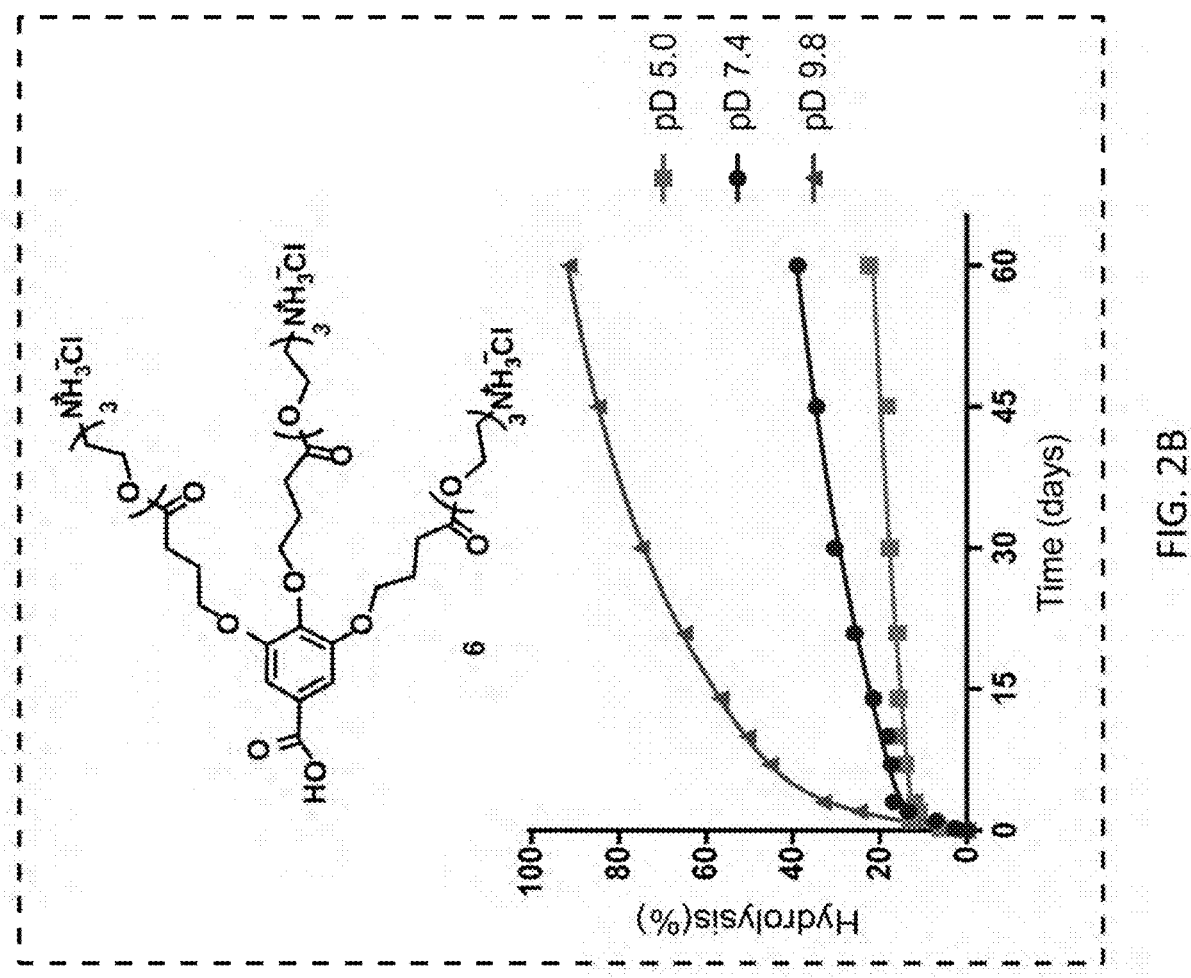

In an embodiment, the synthetic route now disclosed allows structural modifications and degradability tuning by changing the length/nature of the spacer that comprise an ester group (depicted by * in FIG. 2A). Building unit 5 was efficiently synthesized from commercially available chlorotriethylene glycol (3), 4-bromobutanoic acid and gallic acid (1). Initial treatment of 4-bromobutanoic acid with azidetriethylene glycol (obtained from 3 and NaN₃)[16] with DCC and DMAP led to ester 4, in particular with a 97% combined yield. Subsequent coupling of 4 with tert-butyl gallate (2) ($K_2CO_3$, 18C6) followed by hydrolysis afforded the desired building unit 5, in particular with an 82% overall yield (FIGS. 2A-2B).

Examples

In an embodiment where PEG-GATGE copolymers were envisaged as NA vectors, preliminary degradability tests were performed on a readily accessible GATGE unit 6 ($H_2$, Pd/C), which incorporates terminal primary amino groups as cationic surrogates to mimic the cationic character envisaged for the NA complexation. As seen in FIG. 2b, degradation studies were carried out in simulating physiological and endosomal pH conditions (7.4 and 5.0, respectively; 37° C.) afforded hydrolysis of the ester bonds in a time-dependent fashion. Higher degradation rate was obtained at pD 7.4 than 5.0 (FIG. 2B, experiments conducted in deuterated water). This observation can be explained because in deuterated water the hydrolysis reaction is catalyzed at basic pH (pD 9.8, FIG. 2B). However, it is worthwhile mentioning that intracellularly one could expect higher hydrolysis rates at lower pH (as in the case of endosomal pH), since acid catalyzed degradation in water can occur up to thrice faster than in deuterated water ($D_2O$).[17]

In an embodiment, the design, synthesis and characterization of biodegradable PEG-GATGE block copolymers was made as follows.

Figure 1A:
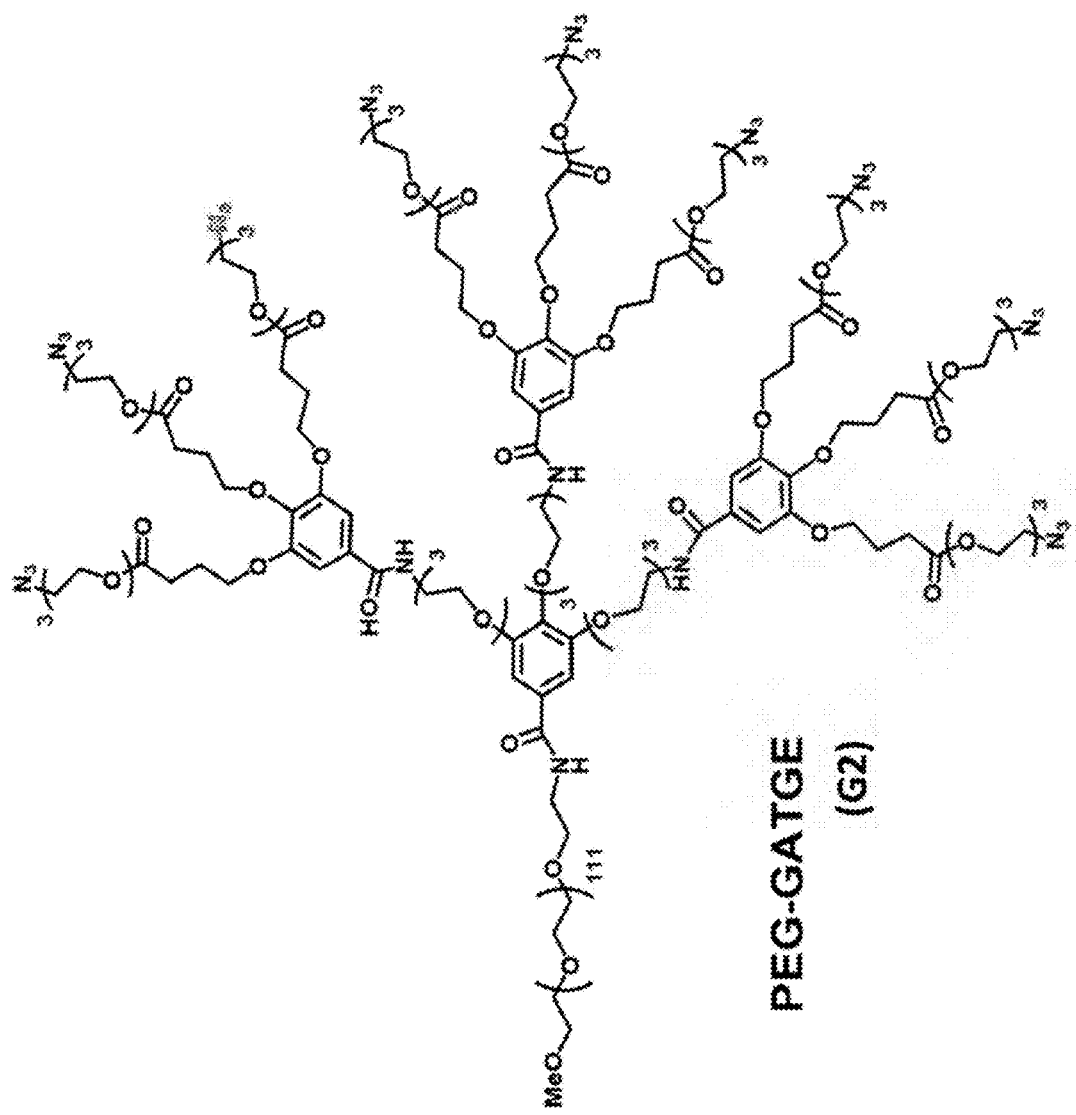
FIGS. 1A-1B—Structure of G2 biodegradable PEG-GATGE block copolymer (PEG-b[G2]-$N_3$) (FIG. 1A). Structure of G3 fully biodegradable PEG-fbGATGE block copolymer (PEG-fb[G3]-$N_3$) (FIG. 1B).

In an embodiment, with a reliable synthesis of 5 in hand and considering the accelerated access and enhanced biocompatibility of lower G, the attention focused on the synthesis and evaluation of the siRNA delivery properties of G2 PEG-GATGE copolymers (PEG-b[G2]) as proof-of-concept of the disclosure (GATGE building unit 5). A hybrid dendritic copolymer was designed combining a classical GATG unit at the core (FIG. 1A) surrounded by a shell of biodegradable GATGE units (FIG. 1A).

In an embodiment, defining the localization of the degradation sites at the dendritic periphery, in close contact to the bioactive (siRNA in this example), will enhance the bioactive intracellular release and biological efficiency compared to the hydrolytically stable PEG-GATG counterparts. Thus, the preparation of PEG-GATGE copolymers was addressed following a divergent strategy starting from a monomethyl ether PEG amino (PEG-$NH_2$.HCl, Mn=5079 g/mol, Mw=5113 g/mol, PdI=1.007) and the GATG unit (7) (Scheme 1).[16] In this way, the block copolymer PEG-[G1]-$N_3$ (8) was readily obtained (EDC, HOBt), in particular with a 93% yield after purification by precipitation (Scheme 1).[18]

In an embodiment, the catalytic hydrogenation of the terminal azides in 8, followed by treatment of the resulting triamine with 5 (EDC, HOBt) led to the desired PEG-b[G2]-$N_3$ (9), in particular with a 86% yield (Scheme 1).

Figure 16:
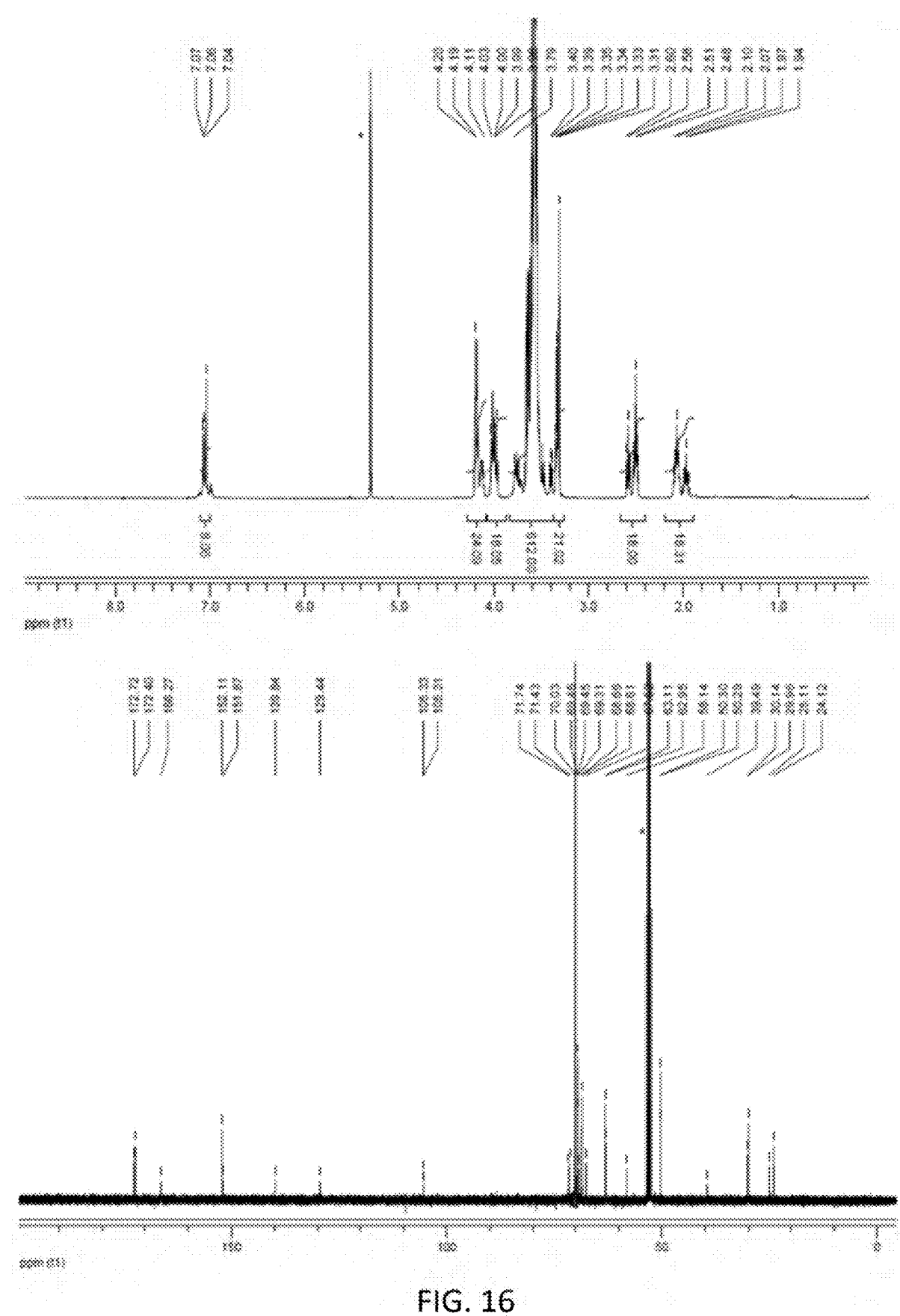
FIG. 16—$^1$H and $^{13}$C NMR spectra of PEG-b[G2]-$N_3$ (9).
Figure 28:
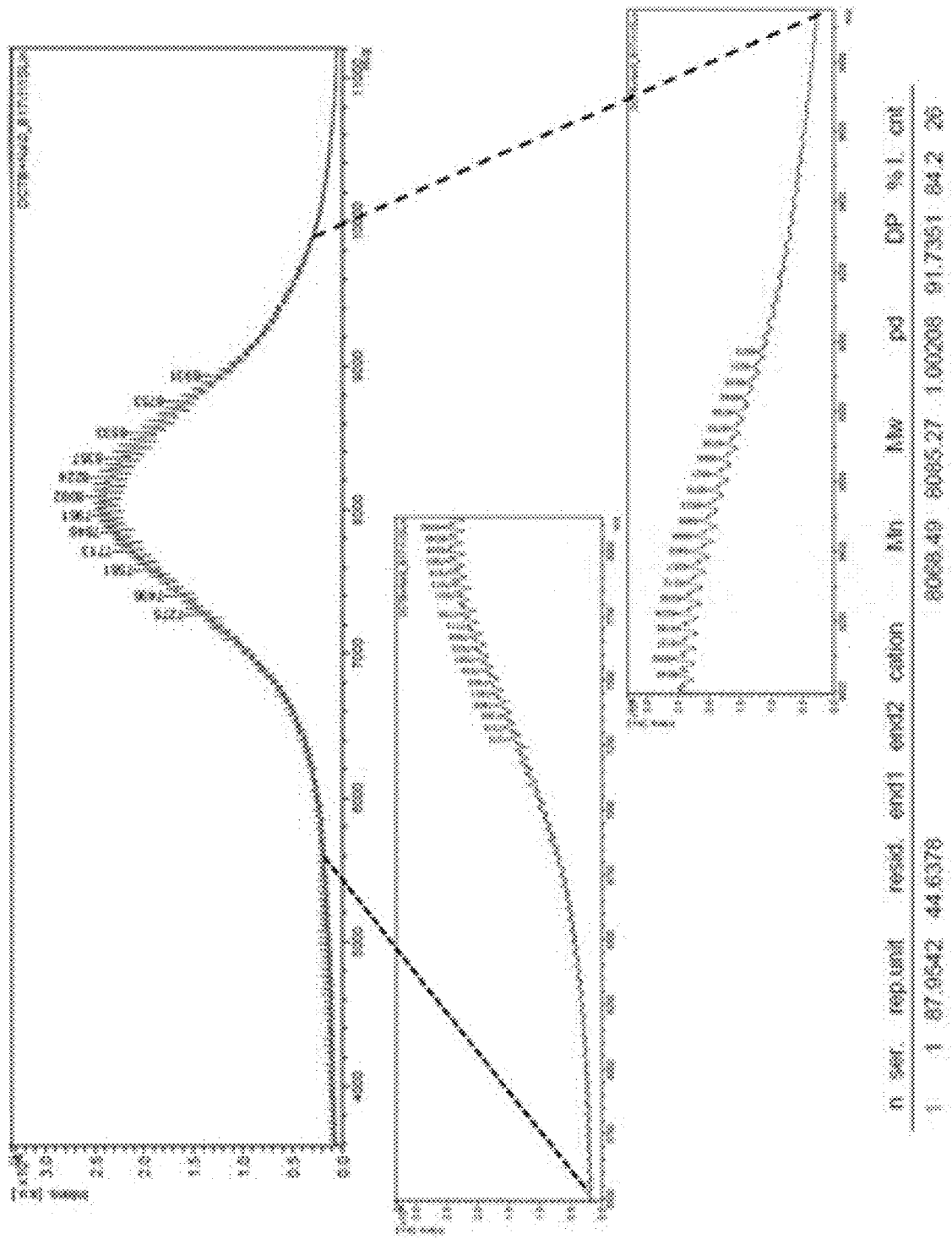
FIG. 28—MALDI-TOF spectrum of PEG-b[G2]-N₃ (9).
Figure 29:
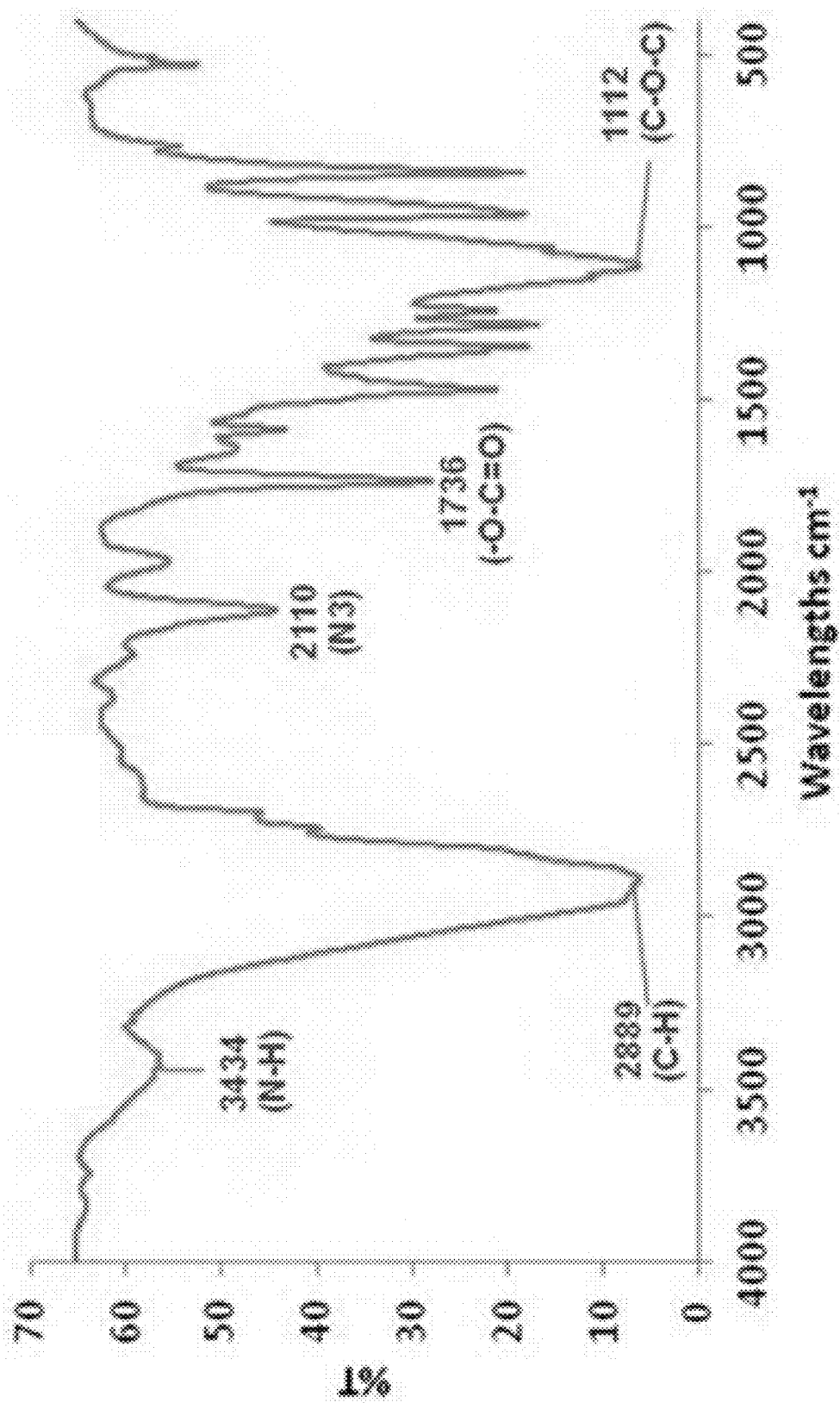
FIG. 29—FTIR transmittance spectrum of PEG-b[G2]-N₃ (9) (KBr).

In an embodiment, the block copolymer 9 was characterized by $^1H$ and $^{13}C$ NMR (1D and 2D), MALDI-TOF MS and FTIR (see FIGS. 16, 28, 29).

Figure 15:
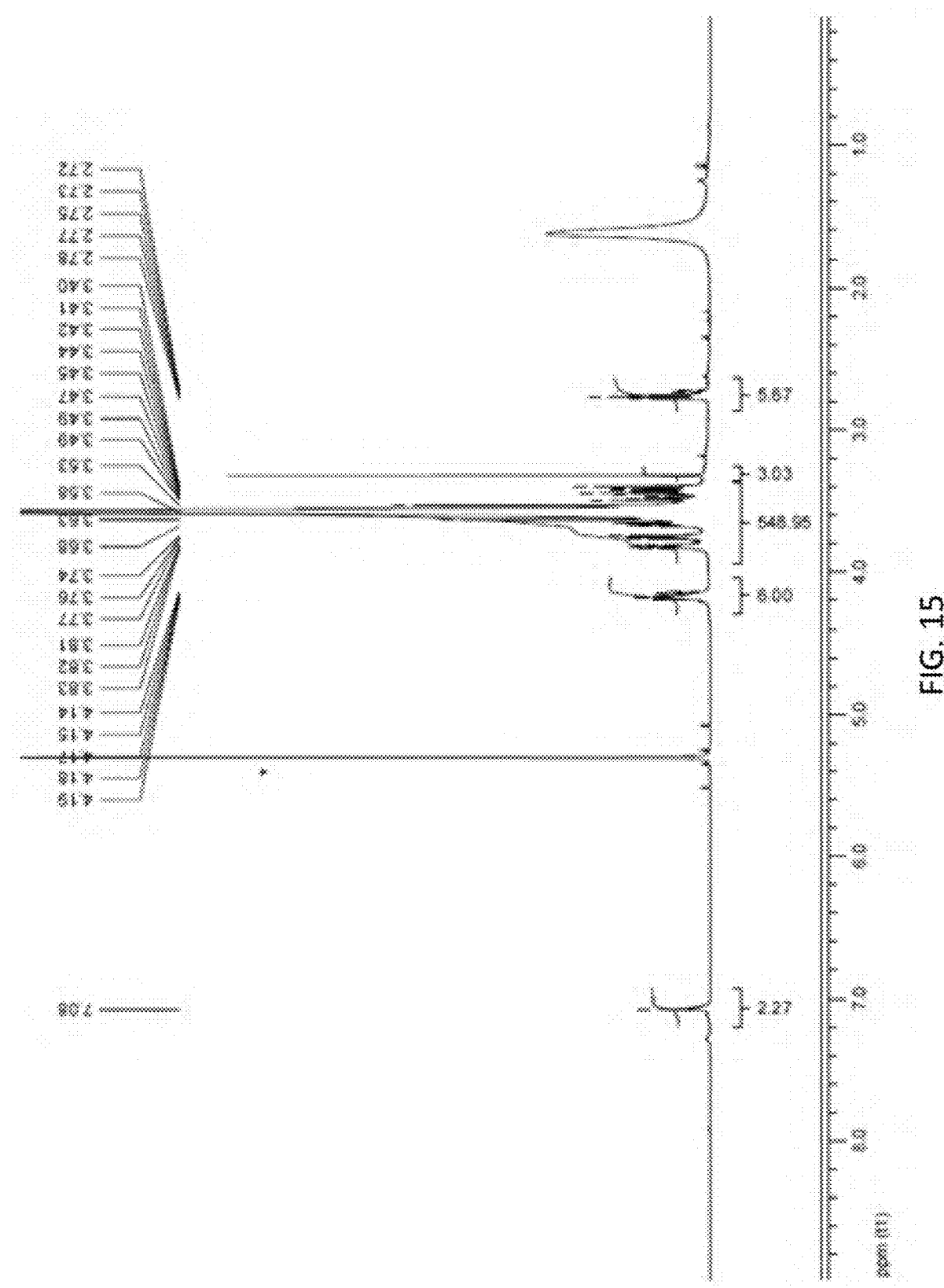
FIG. 15—$^1$H NMR spectrum of PEG-[G1]-$NH_2$

In an embodiment, the dendritic growth was monitored by $^1$H-NMR spectroscopy ($CD_2Cl_2$) by following the butanoate spacer signals (protons h, i, j) and those adjacent to the azide groups (I and I': 3.31-3.35 ppm) (Scheme 1), and by the disappearance of the signals corresponding to the methylene protons adjacent to the amine groups (2.72-2.78 ppm) (FIG. 15).

In an embodiment, the MALDI-TOF spectrum of 9 shows a Gaussian distribution of peaks related to the block copolymer adducts with sodium, spaced by 44 Da that correspond to the expected PEG oligomers (FIG. 28). Experimental molecular weight (Mp), molecular weight (Mw) and number molecular weight (Mn) were in agreement with calculated values. FTIR spectroscopy revealed the presence in 9 of characteristic peaks at 1736 and 2110 $cm^{-1}$ corresponding to ester and azide groups (FIG. 29).

In an embodiment, the design, synthesis and characterization of fully biodegradable PEG-GATGE block copolymers was made as follows.

In an embodiment, the fully biodegradability of the PEG-GATGE dendritic block copolymers is disclosed. A fully biodegradable dendritic copolymer was designed and synthesized until G3 (PEG-fb[G3], FIG. 1B). PEG-fb[G3] is completely based on biodegradable building units 5, because of this it is fully biodegradable.

Figure 1B:
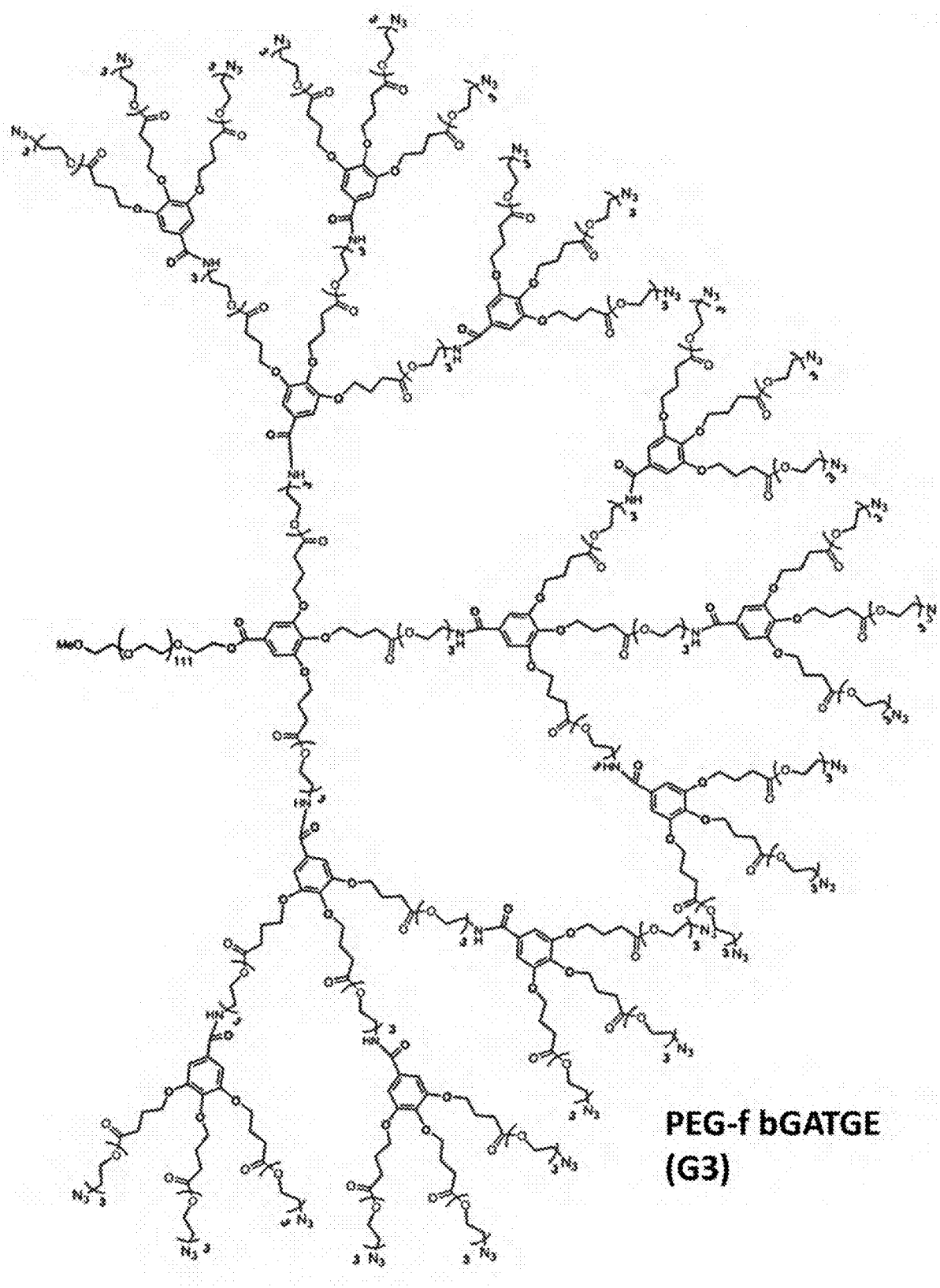

In an embodiment, defining the localization of the 40 degradation sites throughout the whole dendritic structure (including the new degradable linkage between the PEG and the dendritic part—see bond despicted in red in FIG. 1B), will lead to the breakdown in very small fragments which will be easier excreted from the organism, and also it is expected even a better bioactive intracellular release and biological efficiency compared to the bybrid biodegradable PEG-GATGE counterparts. Thus, the preparation of fully biodegradable PEG-GATGE copolymers was addressed following a divergent strategy starting from a poly(ethylene glycol) methyl ether (PEG(5000)-OH, Mw=5000 g/mol) and GATGE unit (5) (Scheme 2).[16] In this way, the block copolymer PEG-fb[G1]-$N_3$ (10) was readily obtained (EDC, DMAP), in particular with a 91% yield after purification by precipitation (Scheme 2).

In an embodiment, the catalytic hydrogenation under acid medium of the terminal azides in 10, followed by treatment of the resulting protonated triamine with 5 (EDC, HOBt, $Et_3N$) led to the desired PEG-fb[G2]-$N_3$ (11), in particular with a 81% yield (Scheme 2).

In an embodiment, in a similar way to the obtaining of PEG-fb[G2]-$N_3$ (11), the subsequent catalytic hydrogenation under acid medium of the terminal azides in 11, followed by sequential treatment of the resulting protonated triamine with 5 (EDC, HOBt, $Et_3N$) led to the desired PEG-fb[G3]-$N_3$ (12), in particular with a 75% yield (Scheme 2).

Figure 17:
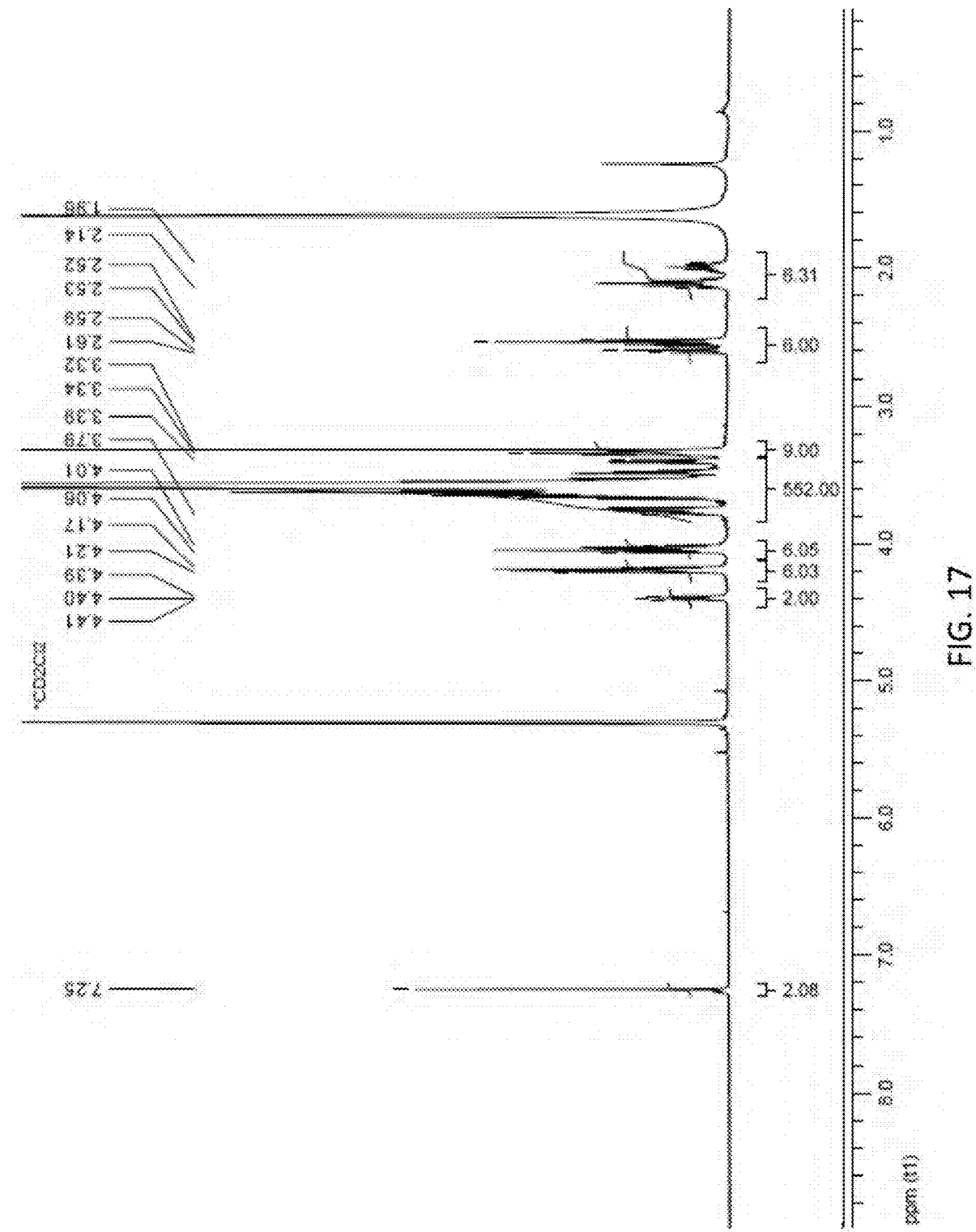
FIG. 17—$^1$H spectrum of PEG-fb[G1]-$N_3$ (10).
Figure 18:
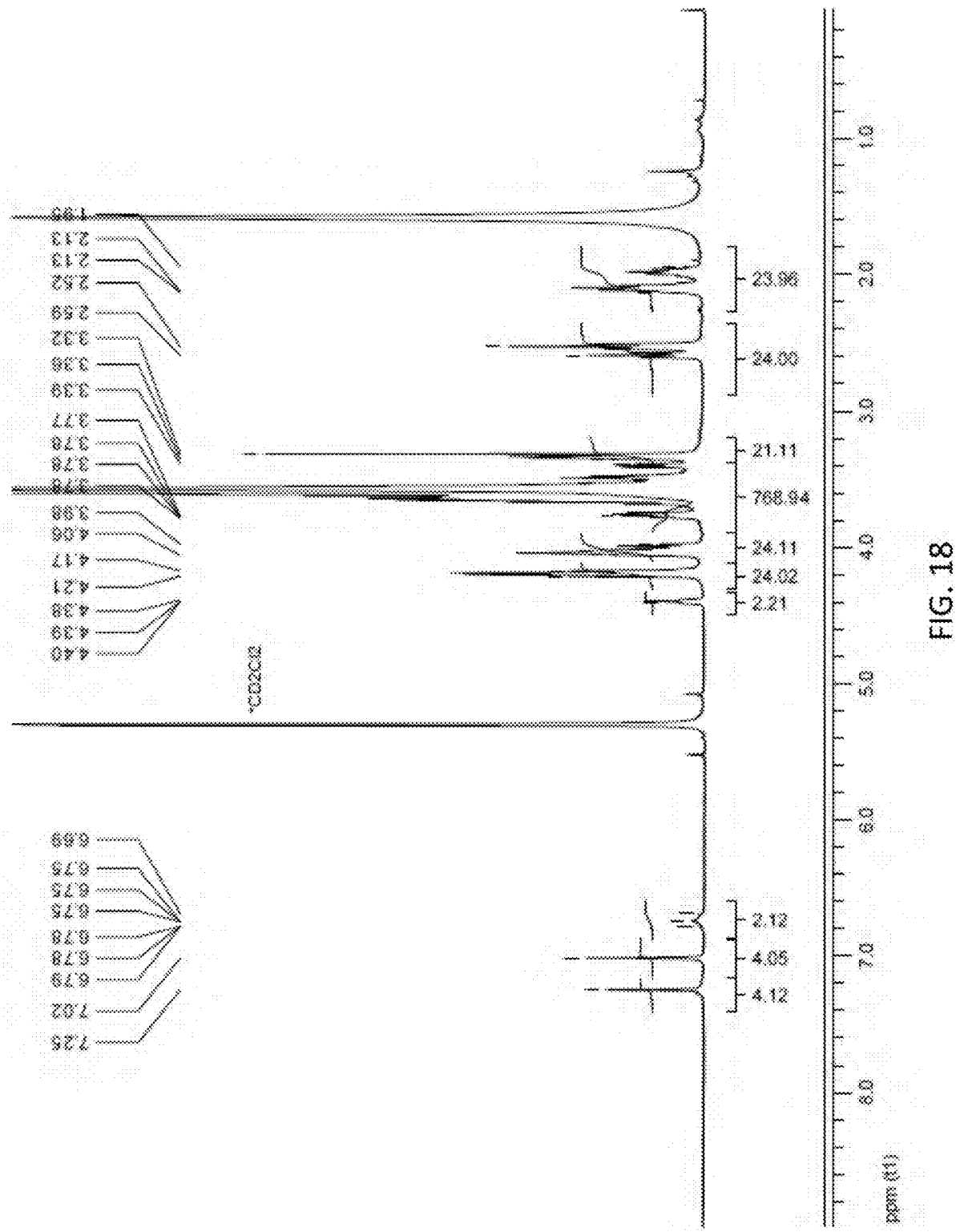
FIG. 18—$^1$H spectrum of PEG-fb[G2]-$N_3$ (11).
Figure 19:
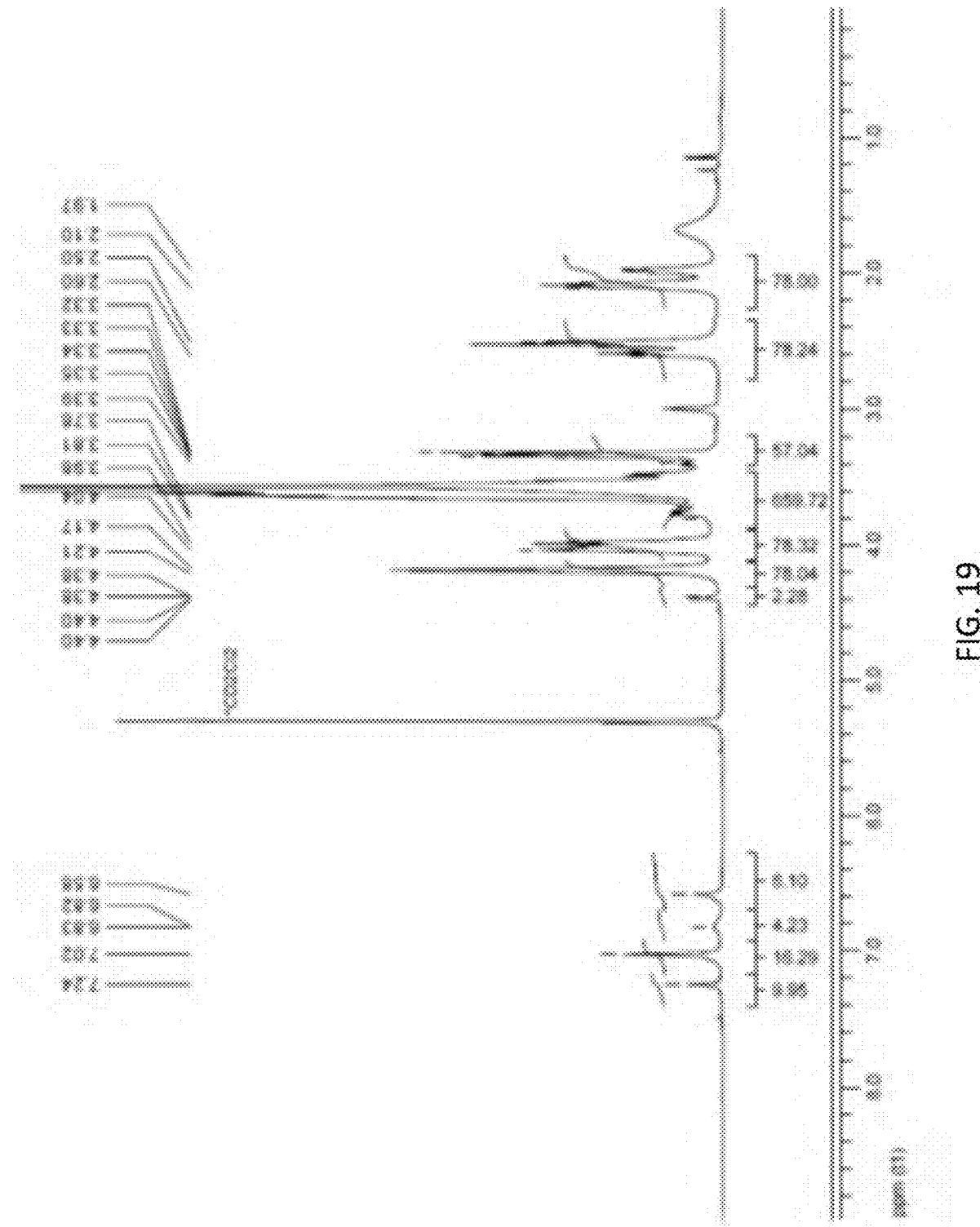
FIG. 19—$^1$H spectrum of PEG-fb[G3]-$N_3$ (12).
Figure 20:
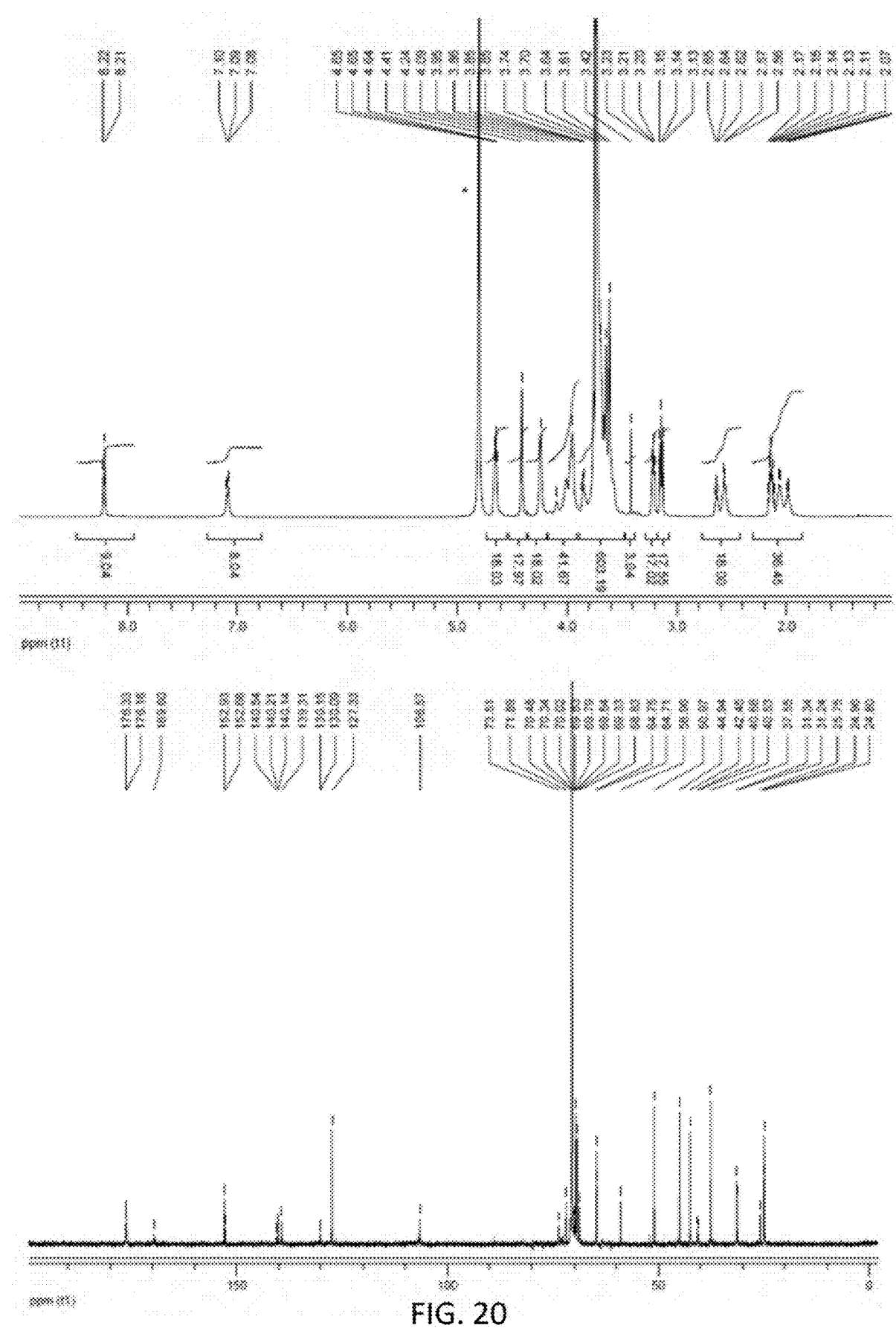
FIG. 20—$^1$H and $^{13}$C NMR spectra of bD (15).
Figure 21:
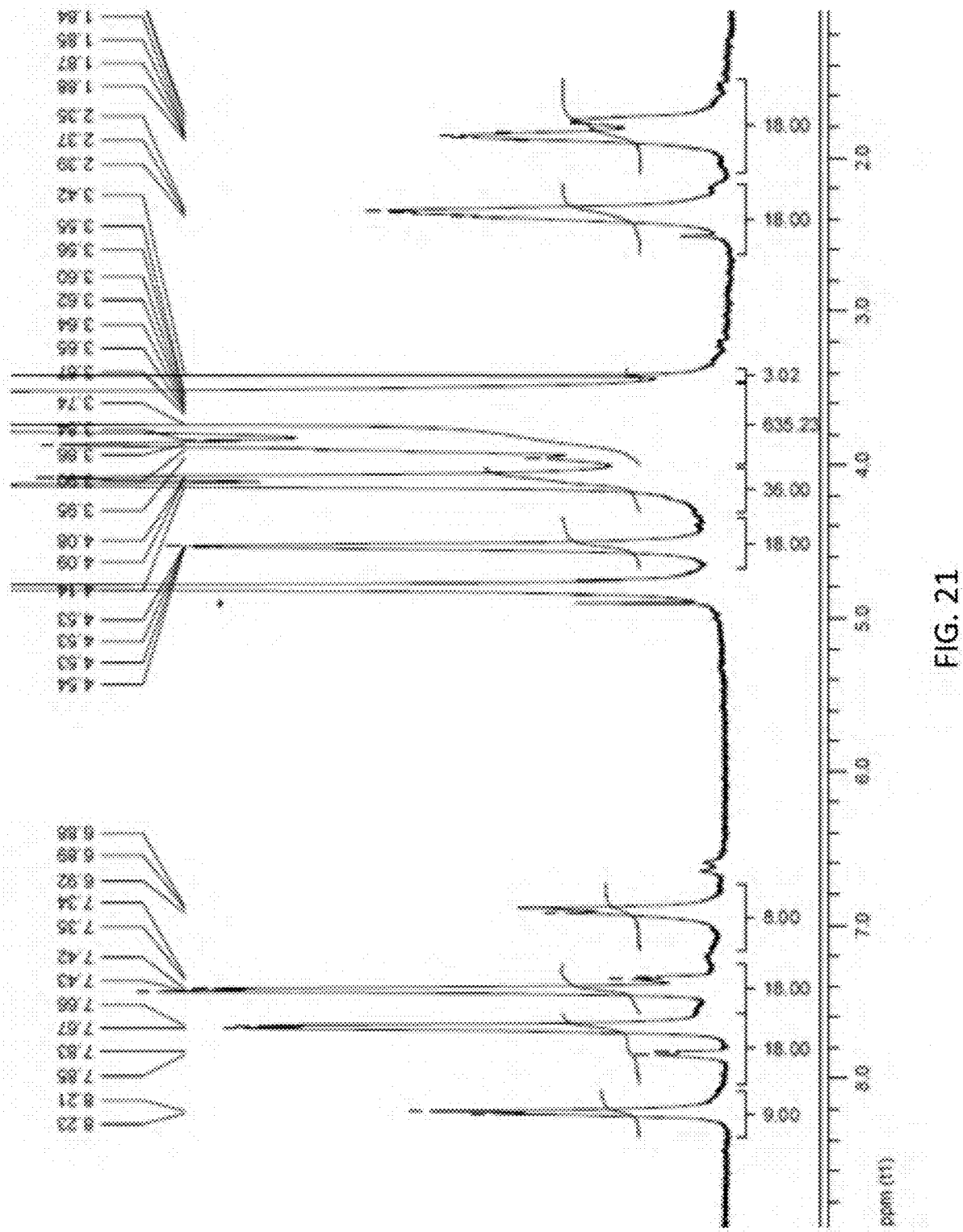
FIG. 21—$^1$H NMR spectrum of bB (16).

In an embodiment, the fully biodegradable block copolymers 10, 11 and 12 were characterized by NMR (FIGS. 17, 18 and 19).

In an embodiment, the dendritic growth was monitored by $^1$H-NMR spectroscopy ($CD_2Cl_2$) by following signals adjacent to the azide groups (~3.32-3.35 ppm), and by the disappearance of the signals corresponding to the methylene protons adjacent to the amine groups (2.72-2.78 ppm). And also by the effect of the growing generation on the splitting of the aromatic signals: while a sharp singlet at 7.25 ppm appeared in the $^1$H NMR spectrum of PEG-fb[G1]-$N_3$ (FIG. 17), two singlets at 7.02 and 7.25 ppm were found in the spectra of PEG-fb[G2]-$N_3$ and PEG-fb[G3]-$N_3$ (FIGS. 18 and 19, respectively).

Functionalization with Unprotected Amines by CuAAC as example of Multivalent Functionalization of Biodegradable PEG-GATGE Copolymer.

Figure 3A:
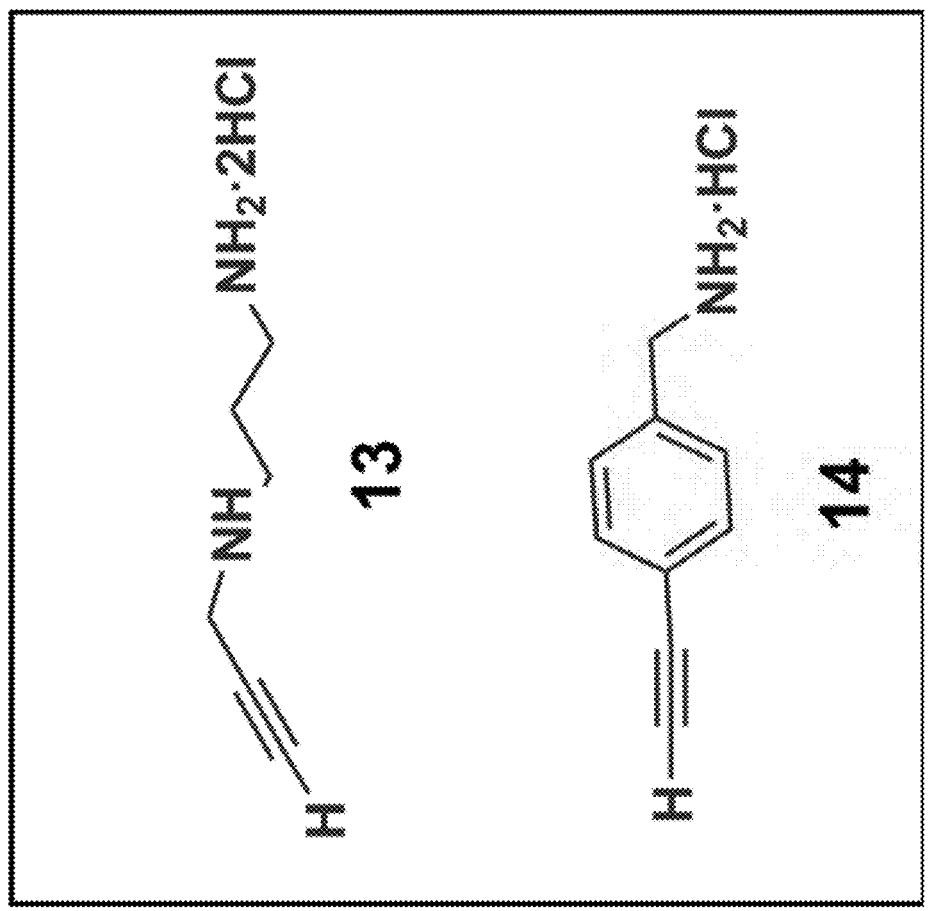

In an embodiment, the multivalent functionalization of biodegradable PEG-GATGE copolymer with unprotected amines by CuAAC was carried out as follows. The cationic nature of amines at physiological pH is usually exploited to enable the ionic condensation and protection of NAs within dendriplexes. It has been previously proposed amine-terminated GATG dendrimers and their PEGylated copolymers as pDNA vectors. However, the use of the same copolymers for siRNA delivery resulted in very limited internalization efficiency with only a 23% of positive cells, probably related to a deficient stability of the dendriplexes. Fundamental differences between pDNA and siRNA molecules regarding size, morphology, flexibility and charge, can result in a less efficient interaction and lower protection of the latter.[19] Thus, commonly used cationic vectors for gene delivery do not necessarily result in optimal siRNA vectors.[20] Here, it is demonstrated that after CuAAC functionalization with alkynated propylenediamine (13) and benzylamine (14) ligands (FIG. 3A), cationic PEG-GATG and PEG-GATGE copolymers enable the efficient complexation of siRNA and its delivery into cells. The use of the diamine (13) aimed to boost the dendrimer-siRNA binding strength by increasing the positive multivalency. The use of benzylamine (14) seeks to increase further the hydrophobicity of the system. It has been previously observed that polyion complex (PIC) micelles derived from PEG-GATG copolymers carrying this aromatic moiety presented higher stability as protein carriers.[21]

In an embodiment, the functionalization of PEG-b[G2]-$N_3$ (9) and PEG-fb[G3]-$N_3$ (12) were carried out with the alkynated free amines, without N-protecting groups, which simplified the number of steps of the process. Instead, their ammonium salts 13 and 14 were used as a means to mask their nucleophilicity and avoid degradation by side-reaction with the ester groups. Moreover, this strategy allows already having the positive charges necessary to complex nucleic acids.

Figure 3C:
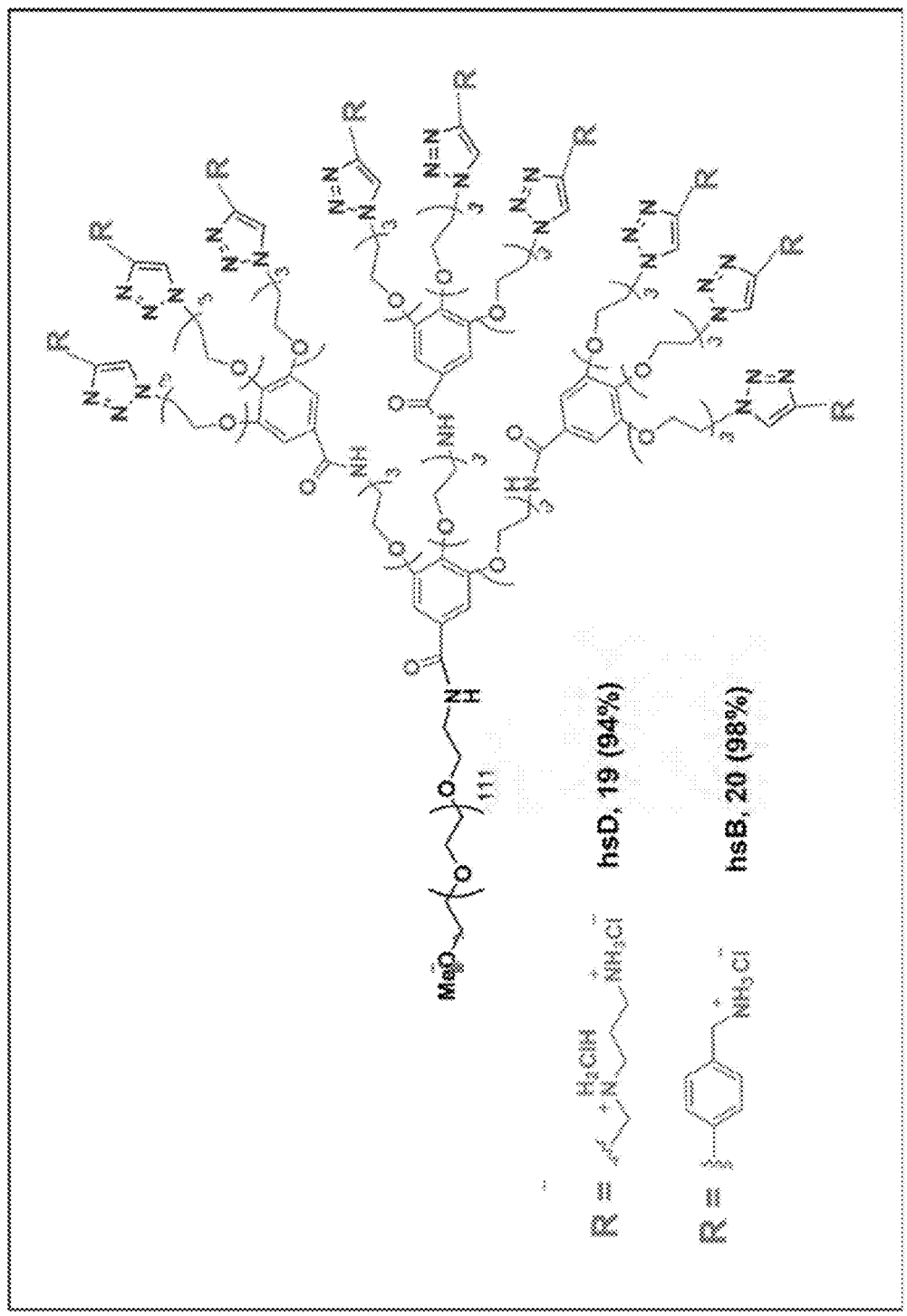
Figure 30:
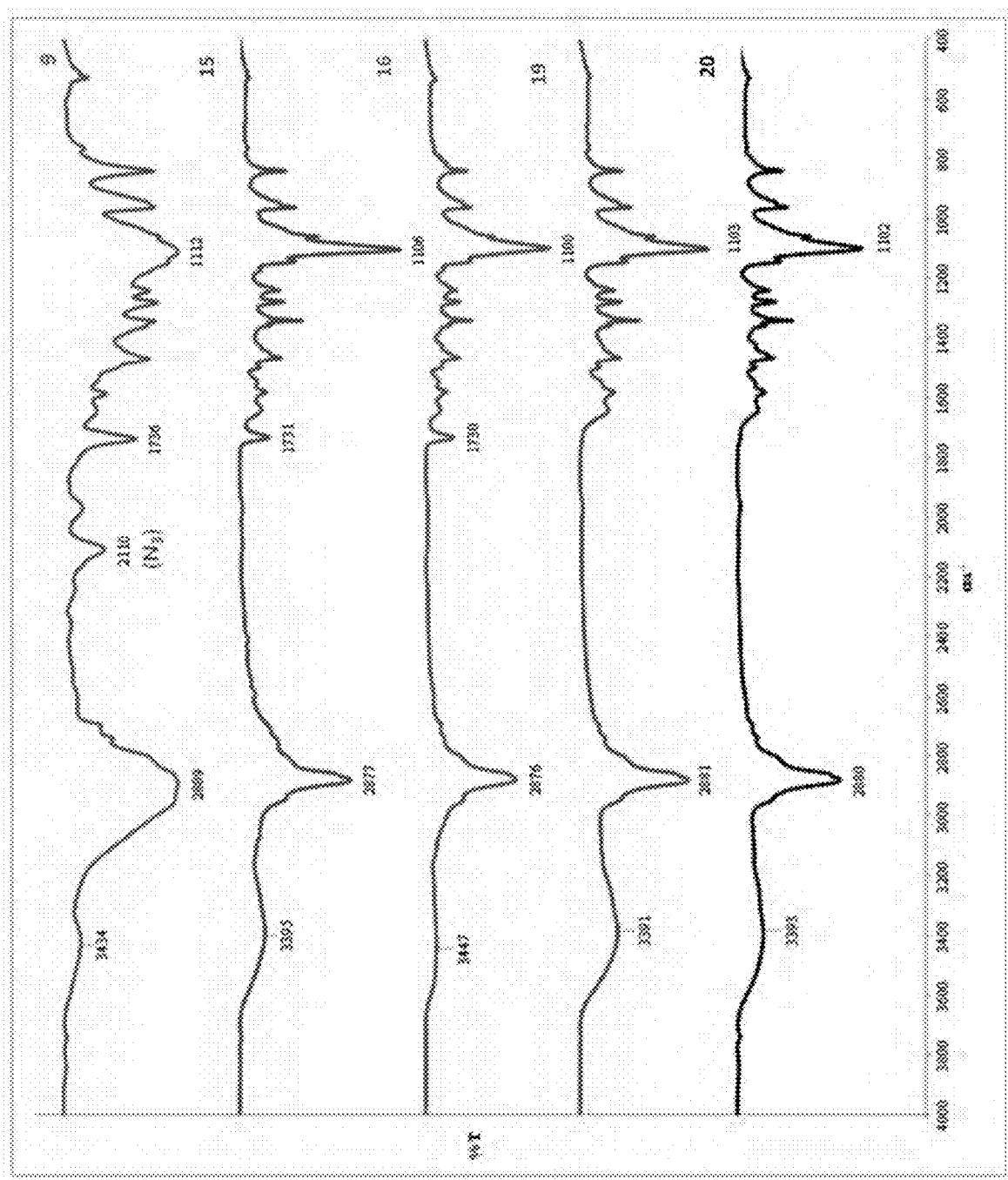
FIG. 30—FTIR Transmittance spectra of PEG-b[G2]-N₃ (9), bD (15), bB (16), hsD (19) and hsB (20) (ATR).

In an embodiment, CuAAC was performed with $CuSO_4$, in particular 5 mol % per azide and sodium ascorbate 25 mol % per azide in $DMF:H_2O$ 1:1, in particular at room temperature for 12 h for G2 and 24 h for G3. The resulting diamine and benzylamine terminated copolymers bD (15) and bB (16) were easily obtained in quantitative yields after purification by ultrafiltration (FIG. 3B). Completion of the conjugation was monitored by $^1$H NMR ($D_2O$) (signal of the methylene protons adjacent to the azide group, FIG. 3B), and FTIR (azide band (2101 $cm^{-1}$) in FIG. 30). Successful coupling was also confirmed in $^1$H NMR by appearance of: a signal around 8.20 ppm corresponding to the triazol protons (m and a multiplet around 4.5-4.7 ppm due to the protons in alpha to the triazol group (I and I'), as well as for the characteristic signals of the amine ligands (n, o, p and q for 15, and r, s and t for 16) (FIG. 3B). Following similar reaction conditions, amine terminated copolymers fbD (17), fbB (18) derived from the fully biodegradable PEG-fb[G3] (12) were also synthesized. In the same way, hsD (19), hsB (20) derived from the hydrolytically stable PEG-GATG copolymer of G2 were also synthesized as controls for siRNA delivery assays (FIG. 3C). Details about the synthesis and characterization of these four amine-dendritic copolymers (17, 18, 19 and 20) can be found in the present document (FIGS. 22-27).

Figure 31:
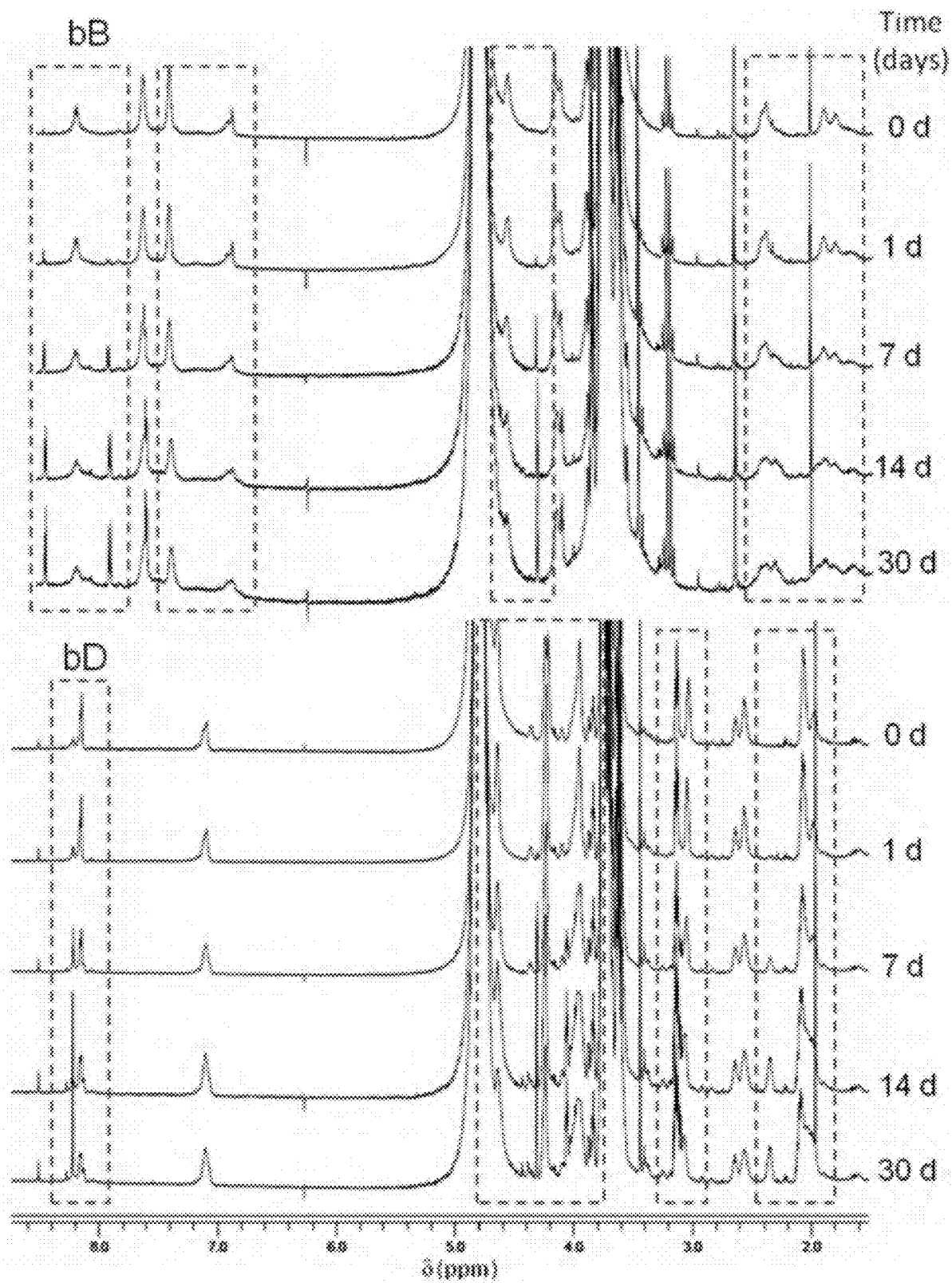
FIG. 31—Degradability studies. ¹H NMR spectra (600 MHz, D2O, PBS 3×, pD 7.4) of amine-terminated bD (15) and bB (16) at different time points (0, 1, 7, 14 and 30 days). The most significant alterations observed on the spectra are highlighted with the dotted rectangles.

Similarly, to the studies performed for the GATGE unit 6, degradability tests were carried out for the biodegradable copolymers bD (15) and bB (16). Qualitative NMR data analysis also point to the degradation of these dendritic copolymers over time at pD 7.4 (FIG. 31), since significant changes, which indicate the instability/degradability of the proposed dendritic copolymers under simulated physiological conditions, can be clearly observed on the spectra. These changes include alterations on the signals intensity and/or shape, as well as appearance and/or disappearance of signals corresponding to the protons of the degraded products and new fragments.

Example of biomedical application of dendritic structures presenting GATGE building unit 5: Biofunctionality assessment of PEG-GATGE copolymers as siRNA vectors.

In an embodiment, the preparation and characterization of dendriplexes was carried out as follows: the association of the amine-terminated copolymers 15, 16, 19 and 20 with siRNA was studied and the physicochemical properties of the resulting dendriplexes evaluated. For the experiments where biological activity is not assessed, a double stranded DNA of exact same sequence as anti-enhanced green fluorescence protein siRNA (anti-eGFP siRNA) was used for mimicking siRNA (siRNAmi) for its ease of synthesis and possibility to obtain in higher yields and purity.

Figure 4B:
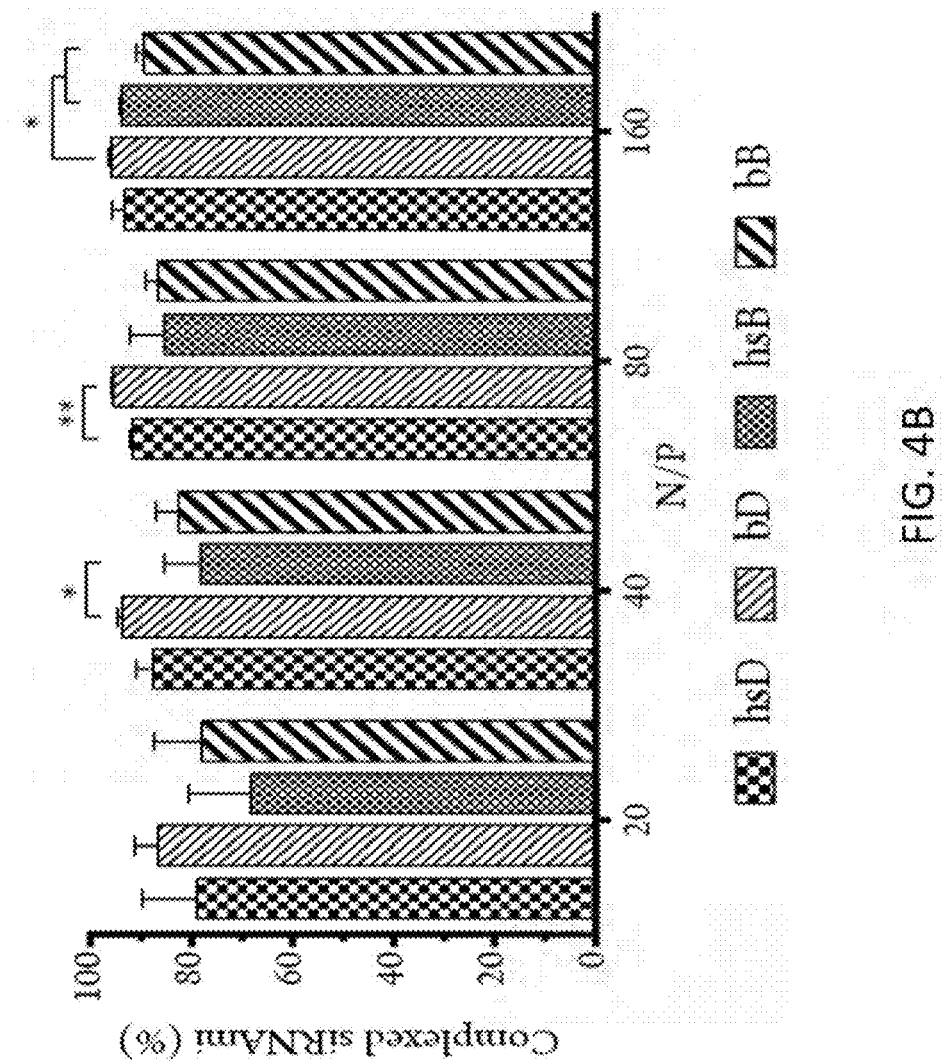
FIGS. 4A-4B—Polyacrylamide gel retention assay (PAGE) of the siRNAmi dendriplexes from: hydrolytically stable PEG-GATG (hsD and hsB) and biodegradable PEG-GATGE (bD and bB) at different N/P (FIG. 4A). SYBR-Gold® exclusion assay at rt. One-way ANOVA tests were used for statistical analysis. Significant differences: *$p<0.05$, **$p<0.01$. Significant differences between N/P's: hsB 20 vs. hsB 160 ($p<0.05$) (FIG. 4B).
Figure 4A:
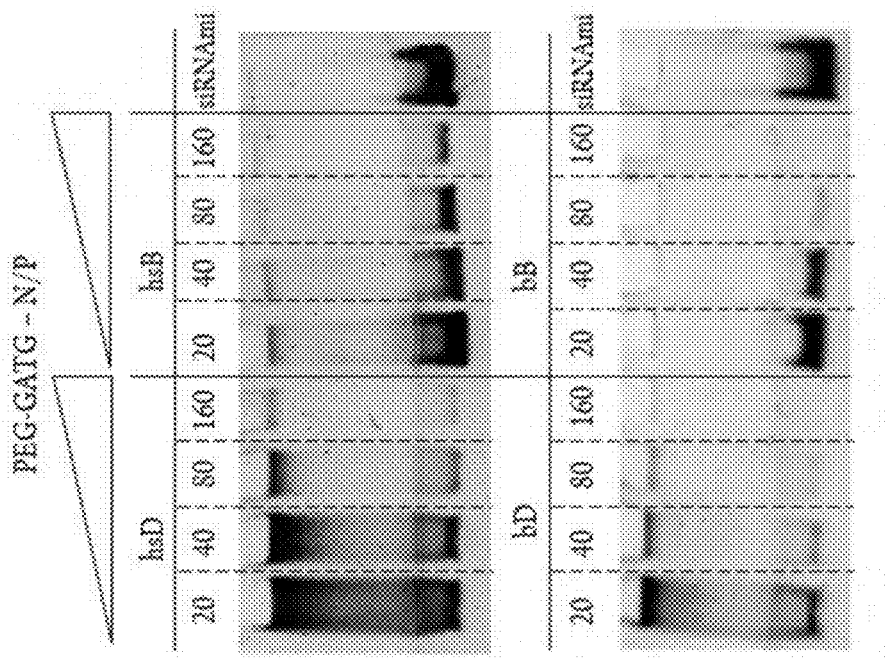

In an embodiment, the siRNA binding ability was determined. The interaction strength of the copolymers with the siRNAmi was initially assessed by polyacrylamide gel retardation assay (PAGE), which for short NA gives a higher resolution compared to traditional agarose gels. The amount of free siRNAmi that migrates in the gel decreased as increasing amounts of copolymers were used (N/P charge ratios ranged from 20 to 160) (FIG. 4A). The charge ratio (N/P) is defined as the ratio between the maximum number of protonable primary amines in the dendritic copolymer and the number of negative phosphates in siRNA or siRNAmi. The complexation efficiency of the copolymers was studied by a nucleic acid dye (SYBRGold®) accessibility assay. The amount of complexed siRNAmi increases with N/P (FIG. 4B). Complexation was 70% for all copolymers in the whole N/P range analyzed, with values >80% at N/P 40. As expected, both PAGE and SYBRGold® assays show the diamine-terminated (D) as the most effective group for retaining and complexing siRNAmi because of the divalent character of the diamine. As for the dendritic framework, the incorporation of the GATGE building unit resulted in a more efficient complexation probably due to the hydrophobic spacers contributing to an enhanced packaging. Altogether, bD resulted the most efficient copolymer in terms of siRNAmi complexation, with around 90% of siRNAmi complexed even at the lowest N/P values studied.

Figures 5A, 5B:
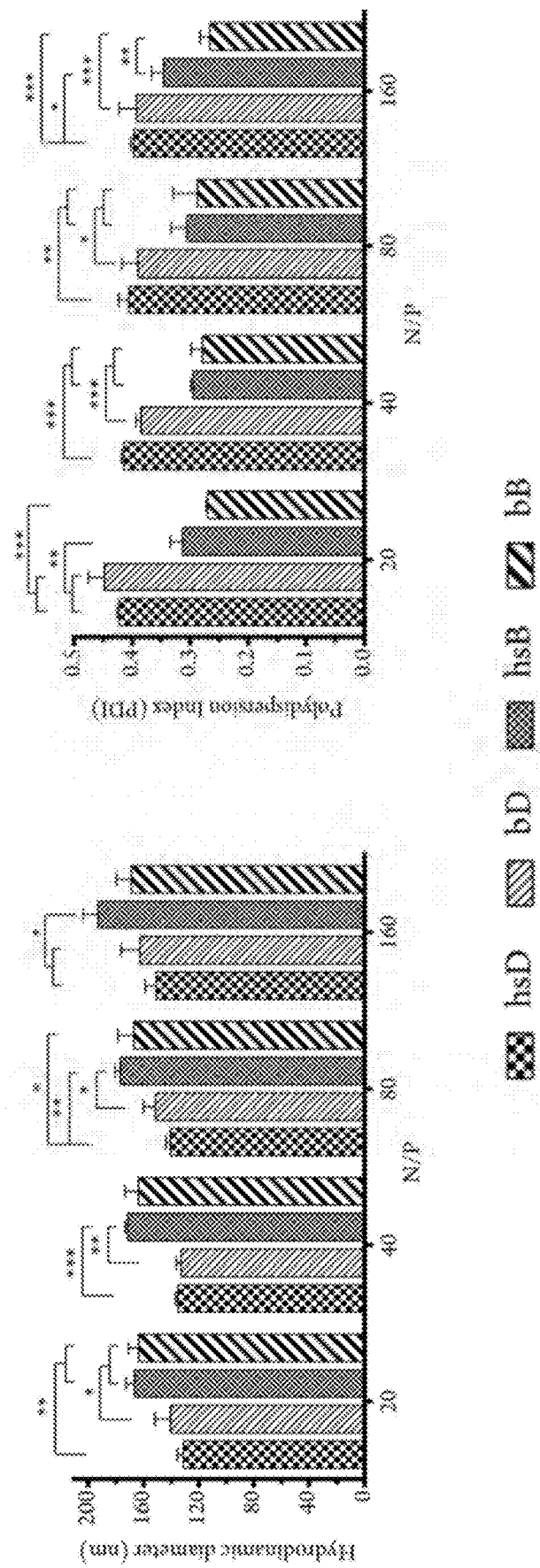
Figure 33A:
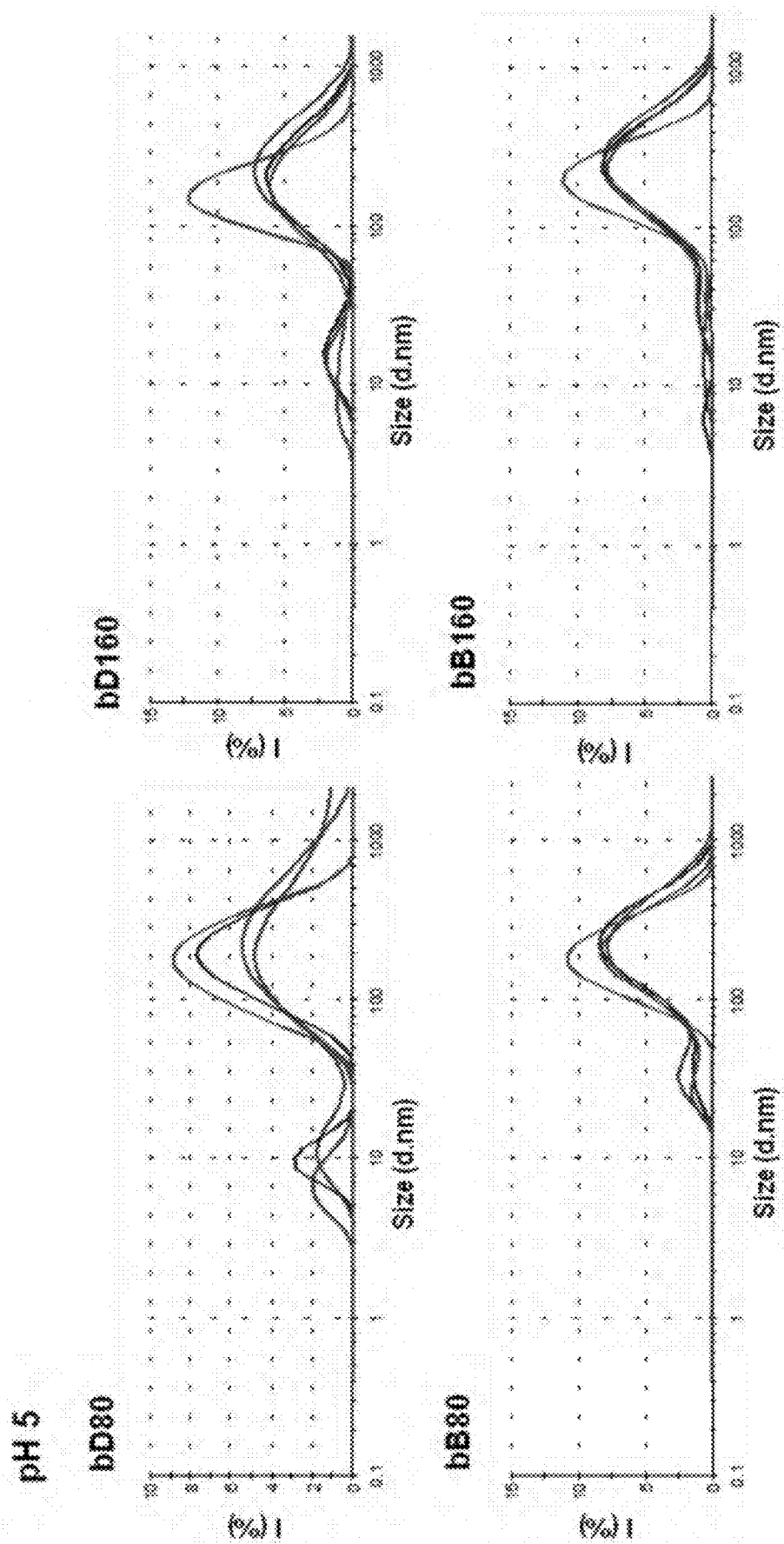
FIGS. 33A-33B—Stability of biodegradable dendriplexes at: pH 5.0 (FIG. 33A) and pH 7.4 (FIG. 33B).
Figure 33B:
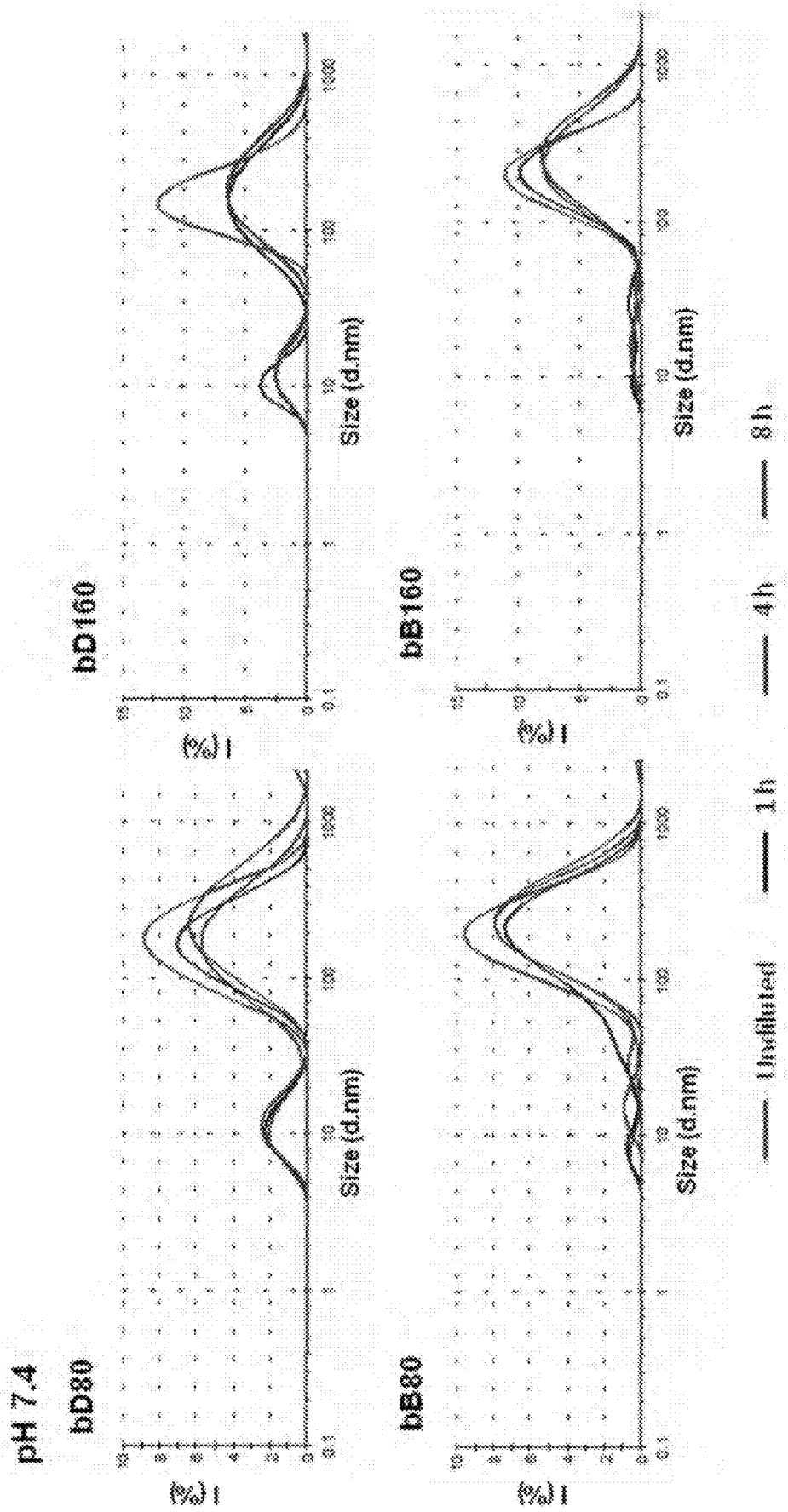

In an embodiment, the size and morphology of the dendriplexes was determined as follows: dendriplexes were characterized in terms of size and morphology using dynamic light scattering (DLS) and transmission electron microscopy (TEM), respectively. Regardless of the dendritic copolymers, a narrow particle size distribution in the nanometer scale was obtained for all N/P tested, with suitable size and polydispersity for cellular uptake.[10e,22] Furthermore, both size and PDI were found to be independent of the N/P. Dendriplexes of average size around 145 nm were obtained for the diamine series and 175 nm for the benzylamine one (FIGS. 5A and 5C). Dendriplex population was slightly more homogenous for the benzylamine than diamine copolymers (PDI around 0.3 and 0.4, respectively, FIG. 5b). Thus, to compare the stability of the dendriplexes based on both terminal amine groups (diamine and benzylamine), sizes of the biodegradable dendriplexes at N/P 80 and 160, were measured after 1, 4 and 8 h of incubation in PBS containing 20% (v/v) of FBS (FIGS. 32A-32D). The peak intensity versus size profile obtained indicates that the incubation of the bD dendriplexes in the presence of serum induced a decrease of the maximum peak intensity, an increase of the peak width and a shift toward increased sizes. However, no significant differences were observed for bB dendriplexes, pointing to the high stability of this system. When the size of the dendriplexes (N/P 80 and 160) were studied as a function of pH (FIGS. 33A-33B) at different time points (1, 4 and 8 h), no significant differences were observed for all formulations at pH 7.4, when analyzing the peak of higher intensity (FIG. 33B). While at pH 5, a slight shift of the dendriplex population toward increased sizes was observed (FIG. 33A). These alterations were less notable for bB dendriplexes, indicating, again, their higher stability. In all cases, it was observed the appearance of smaller populations, which we ascribe to the appearance of dendriplex degradation sub-products. Under these conditions, these can be distinguished due to the absence of other larger molecules (as in the case of the data previously discussed, FIGS. 32A-32D where the characterization was performed in the presence of FBS).

Figure 5E:
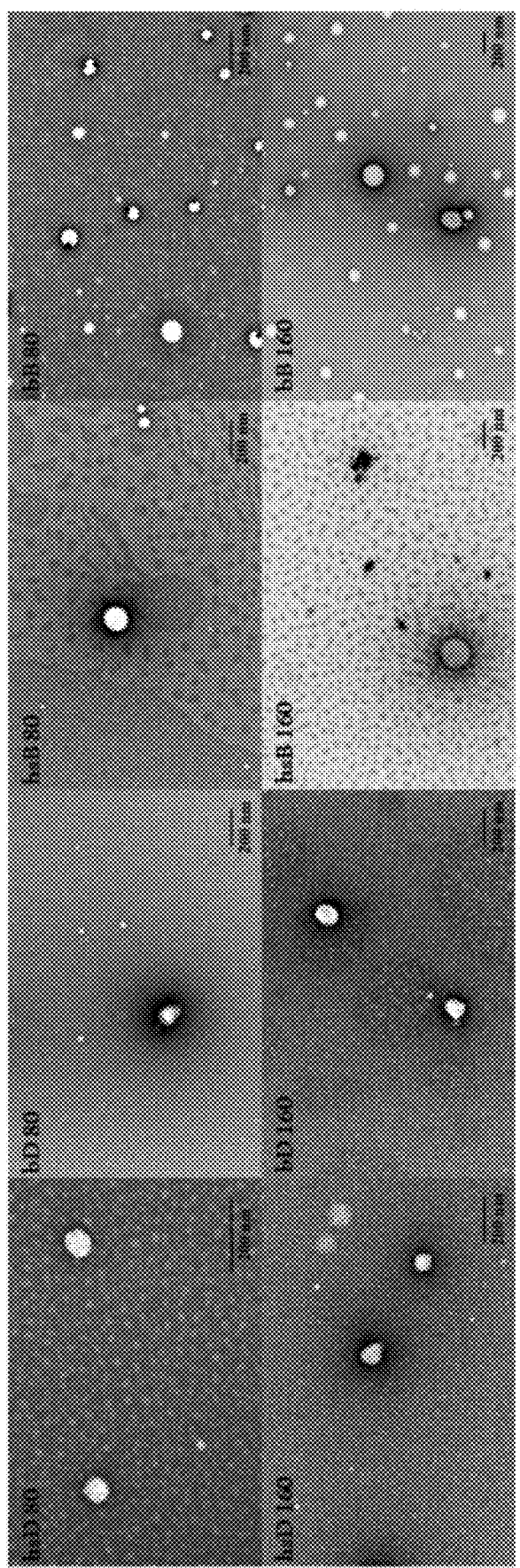

As shown in the TEM images (FIG. 5E), all dendriplexes show spherical and compact structures with sizes that correlate well with those obtained by DLS (FIG. 5A).

Figures 34A, 34B:
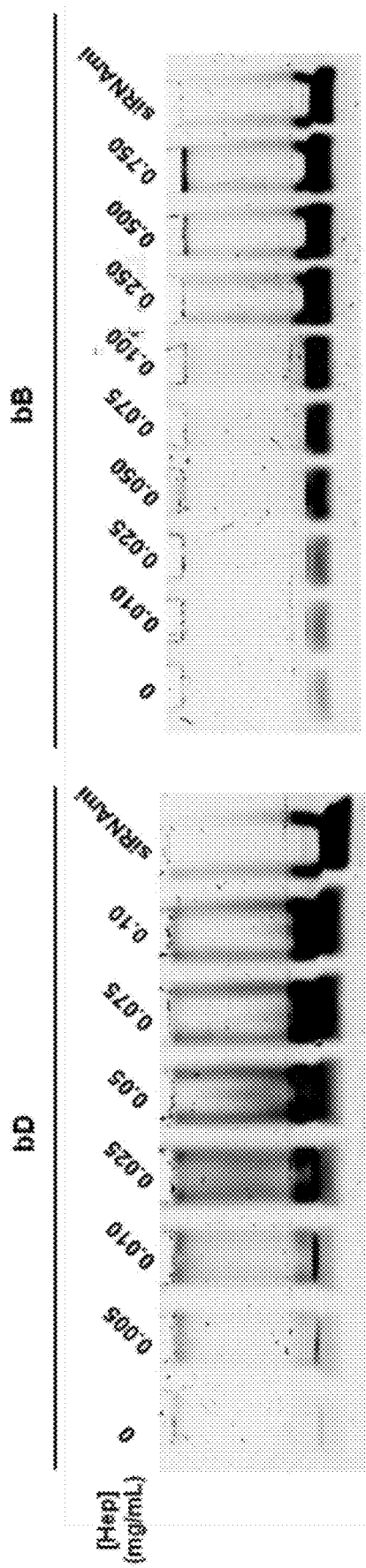
FIGS. 34A-34B—Heparin dissociation assay for: bD (FIG. 34A) and bB (FIG. 34B) dendriplexes. bD and bB dendriplexes at N/P 160 were incubated with increasing concentrations of heparin at 37° C. in physiological salt and pH conditions for 2 h. Samples were then run using PAGE to verify the extent of dissociated siRNAmi from the dendriplexes. In the siRNAmi lane the same amount of free siRNAmi as used for the preparation of the dendriplexes was loaded.

Another important parameter for the cellular activity of the transfection dendriplexes is their capacity to release the siRNA once inside the cell. Thus, to test the reversibility of dendriplex formation, biodegradable dendriplexes were incubated at 37° C. and at physiological salt and pH conditions with heparin, a model polyanion commonly used to test destabilization and release of nucleic acids from dendriplexes.[20c,23] bD and bB dendriplexes (N/P ratio 160) were tested, with an extensive release of siRNA being observed when these challenged with increased concentrations of heparin (FIGS. 34A-34B).

Taken together, these results and the dendriplexes' stability in the presence of serum and as a function of pH, one can conclude that there is a good equilibrium in terms of extracellular stability and intracellular siRNA release, especially for the bB-based dendriplexes. The importance of the hydrophobic interactions between vector and NA seems to emerge again from all these results with terminal aromatic groups leading to more homogeneous and stable dendriplexes.

In an embodiment, the Zeta potential was carried out. The surface charge of the dendriplexes in water was measured by laser Doppler electrophoresis (FIG. 5D). For all tested formulations the dendriplexes net charge was positive, with diamine dendriplexes presenting higher zeta potentials compared to benzylamine, in agreement with the expected higher density of positive charges.

Figures 35A, 35B:
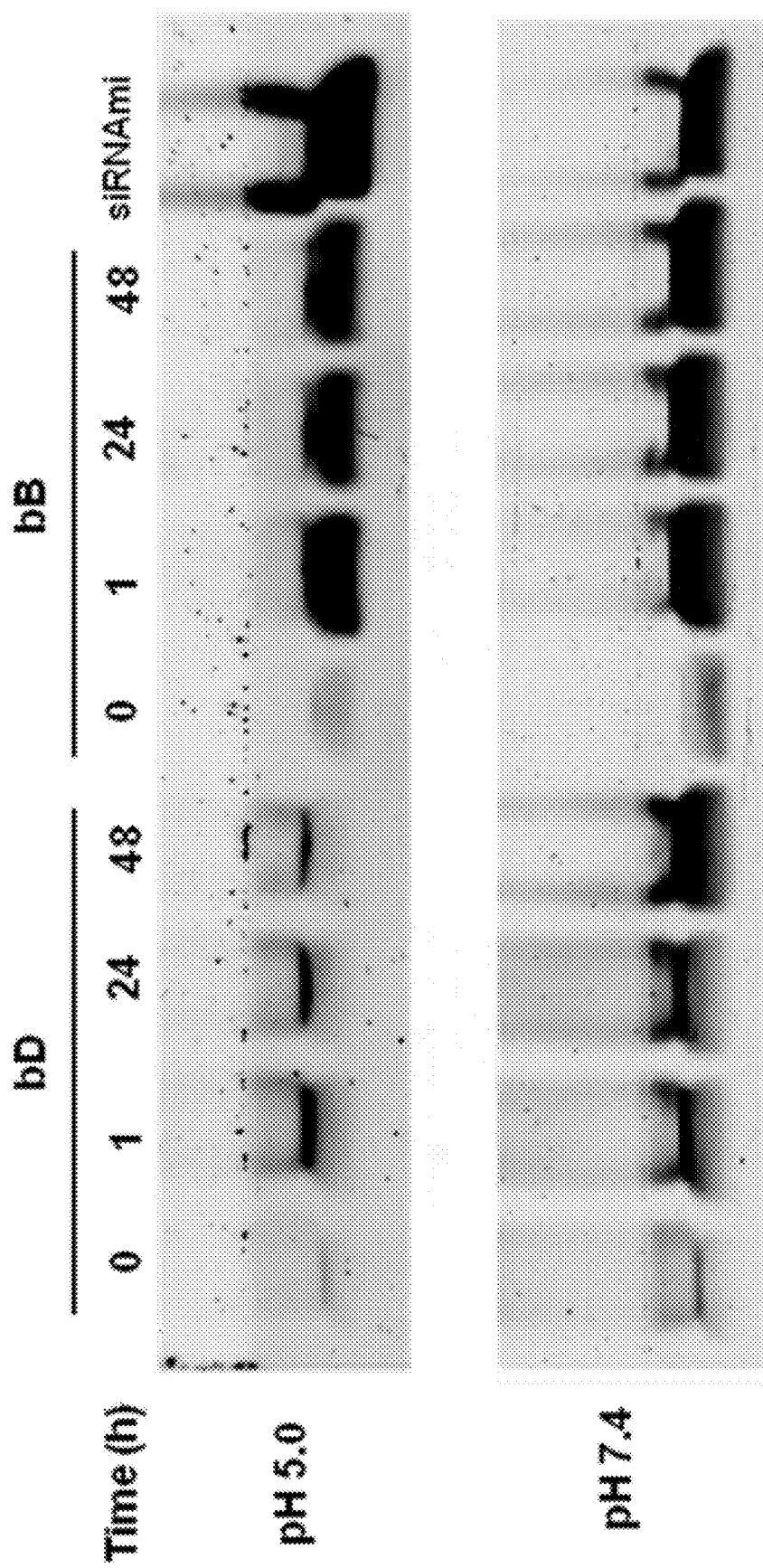
FIGS. 35A-35B—Dendriplexes degradation studies. Degradation studies for: bD (FIG. 35A) and bB siRNA (FIG. 35B) dendriplexes. bD and bB at N/P 160 were incubated under acid (pH 5.0) and physiological pH (pH 7.4) conditions for 1, 24 and 48 h. Then, dendriplexes were incubated with heparin (at a final heparin concentration of 0.010 mg/mL and 0.025 mg/mL for bD and bB dendriplexes, respectively) for 2 h at 37° C., in order to determine, in an indirect way, the amount of siRNA released with the time.
Figure 37:
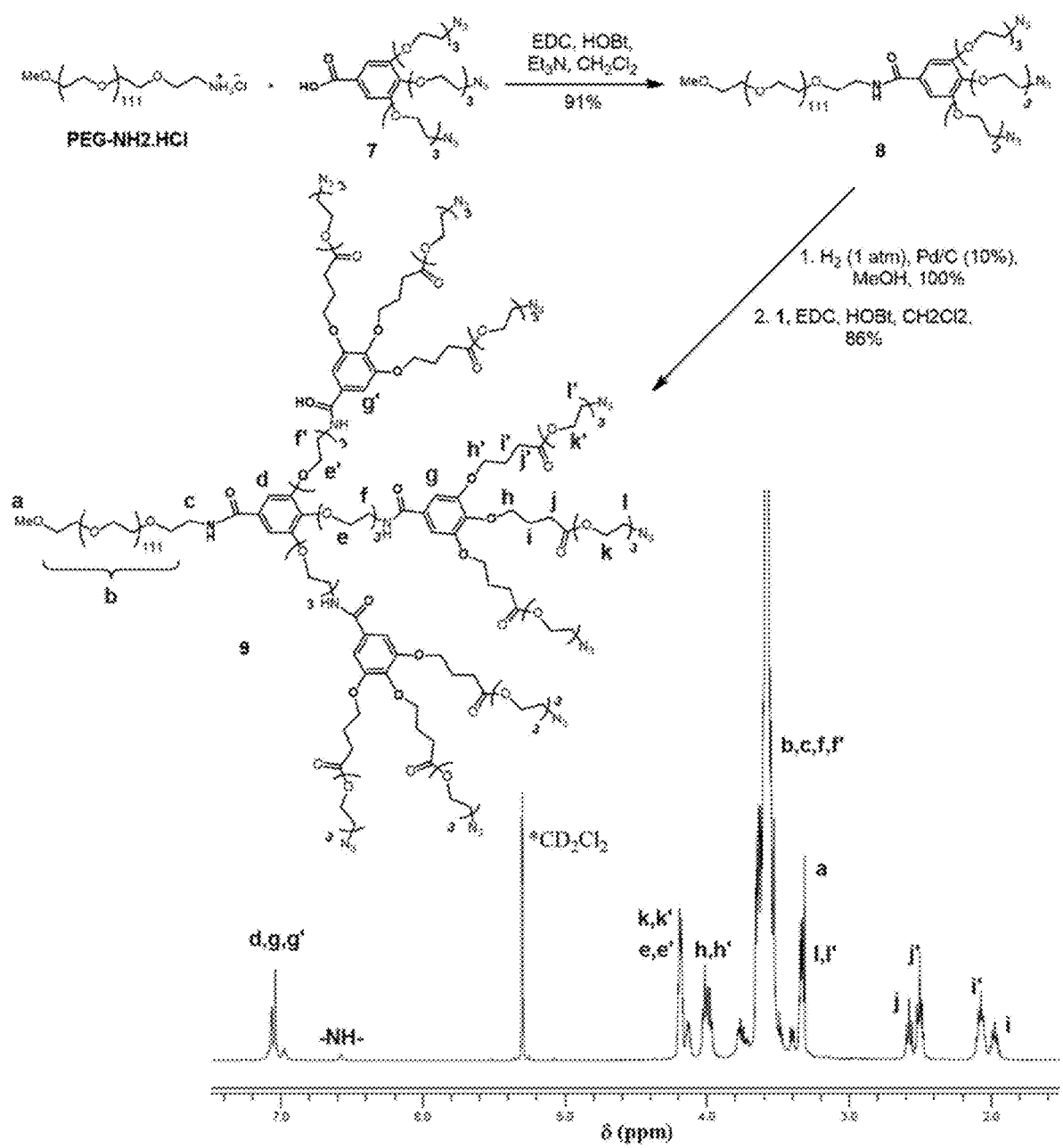
FIG. 37—Scheme 1. Synthesis and ¹H NMR spectrum (400 MHz, CD₂Cl₂) of PEG-GATGE copolymer 9.
Figure 38:
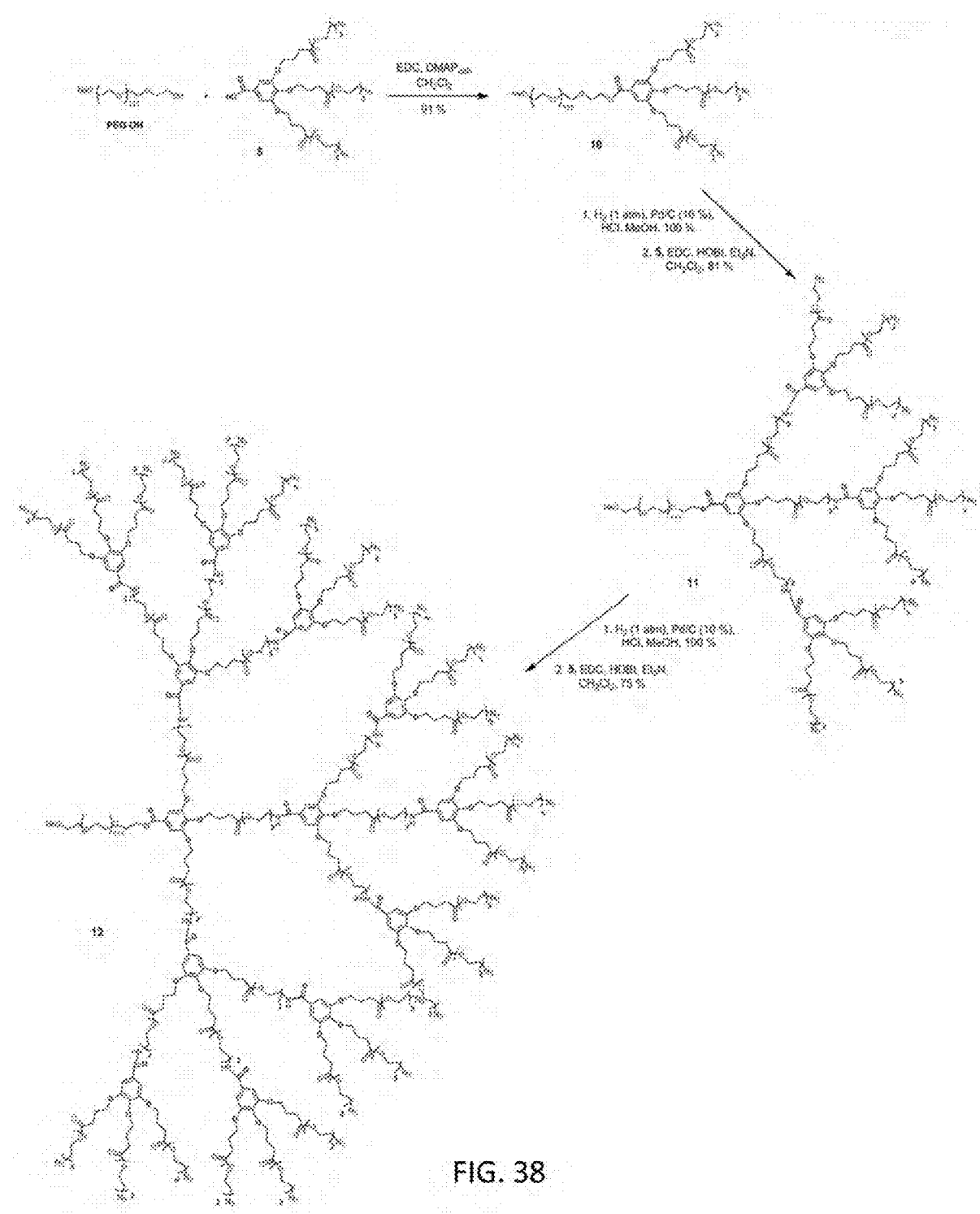
FIG. 38—Scheme 2. Synthesis of fully biodegradable PEG-fbGATGE copolymers 10 (G1), 11 (G2) and 12 (G3).
Figure 39:
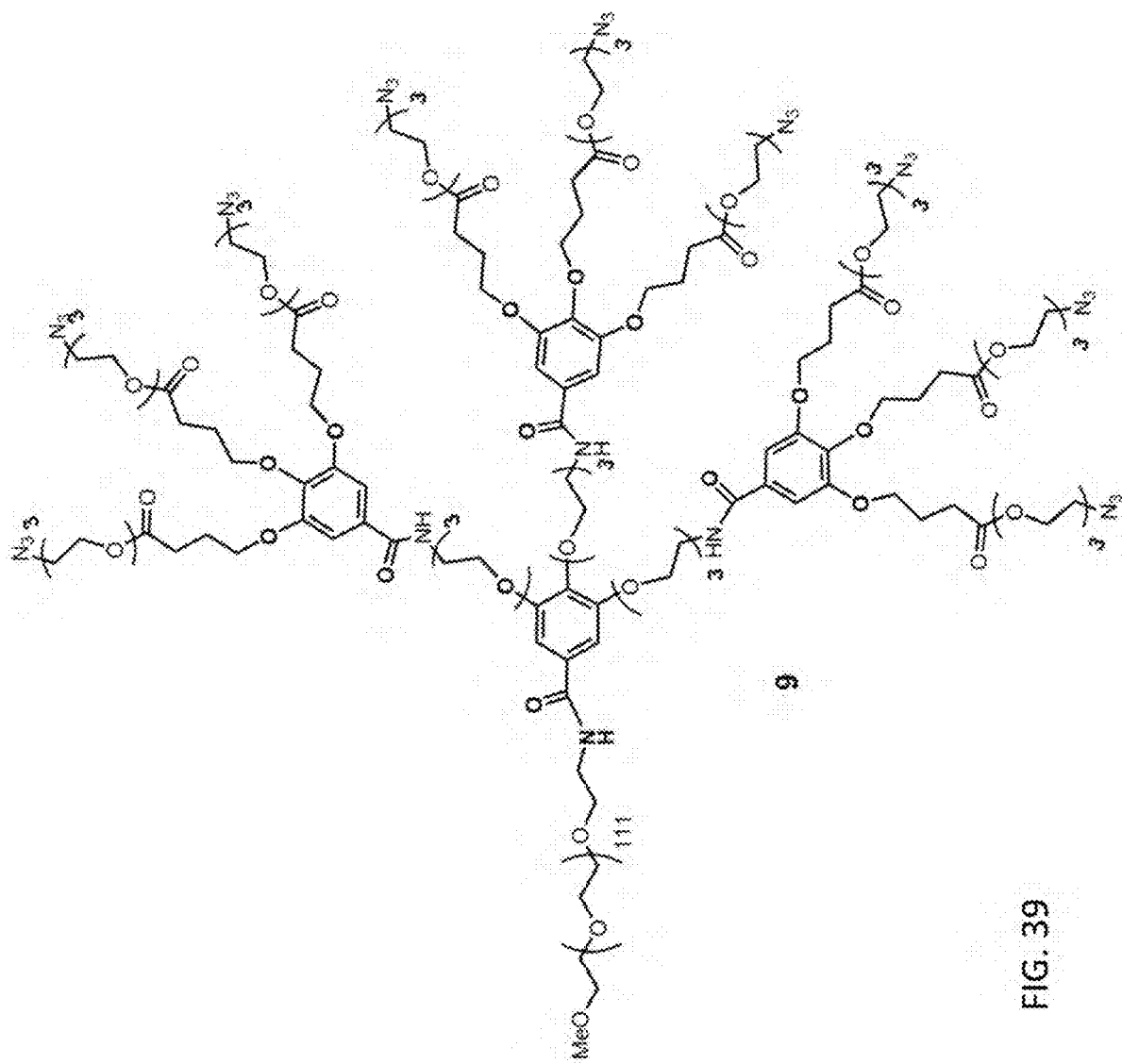
FIG. 39—Structure of G2 biodegradable PEG-GATGE block copolymer (PEG-b[G2]-N₃ 9) with polyethylene glycol 5000.
Figure 40:
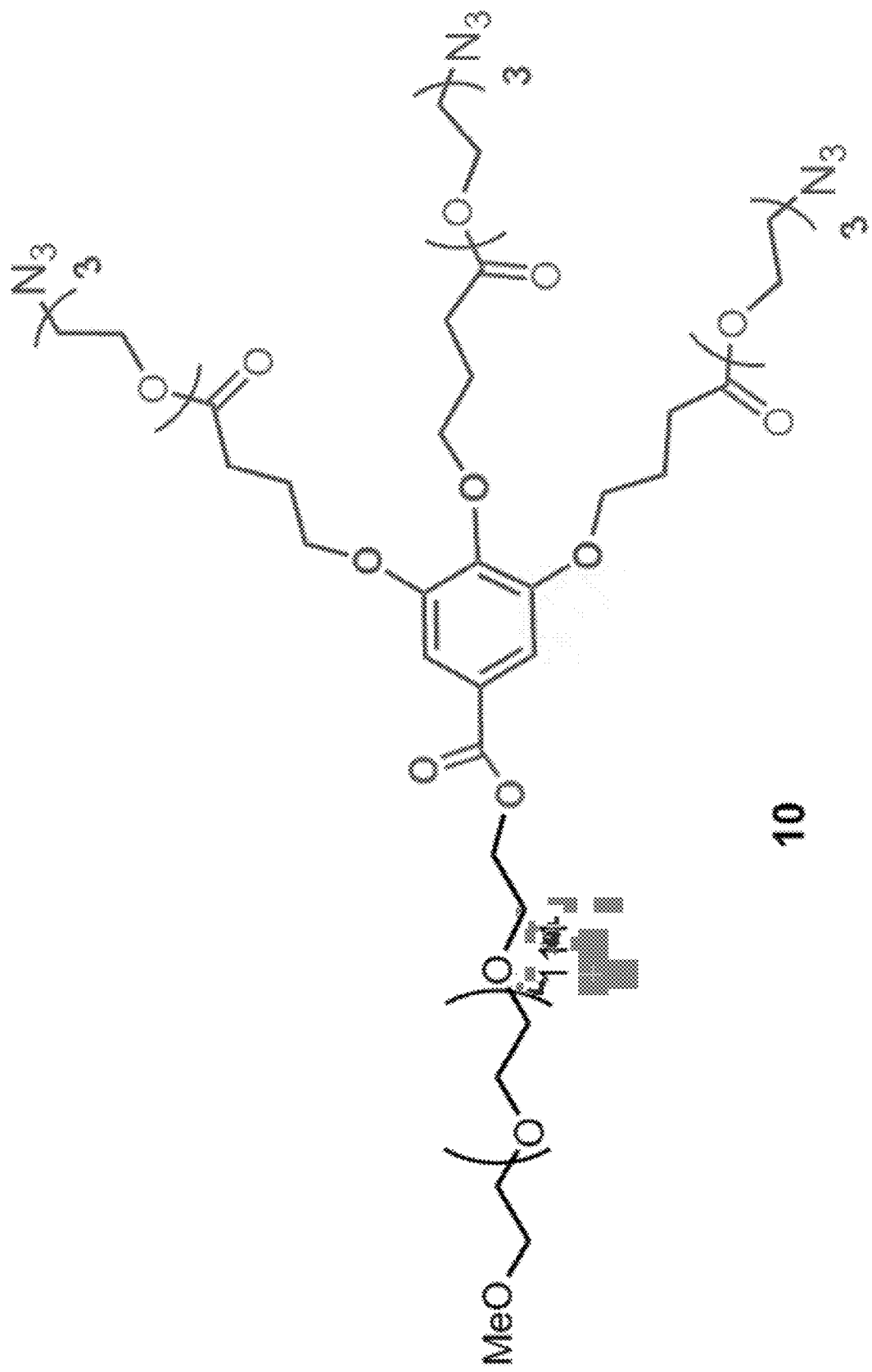
FIG. 40—Structure of G1 fully biodegradable PEG-fb-GATGE block copolymer (PEG-fb[G1]-N₃ 10) with polyethylene glycol 5000.
Figure 41:
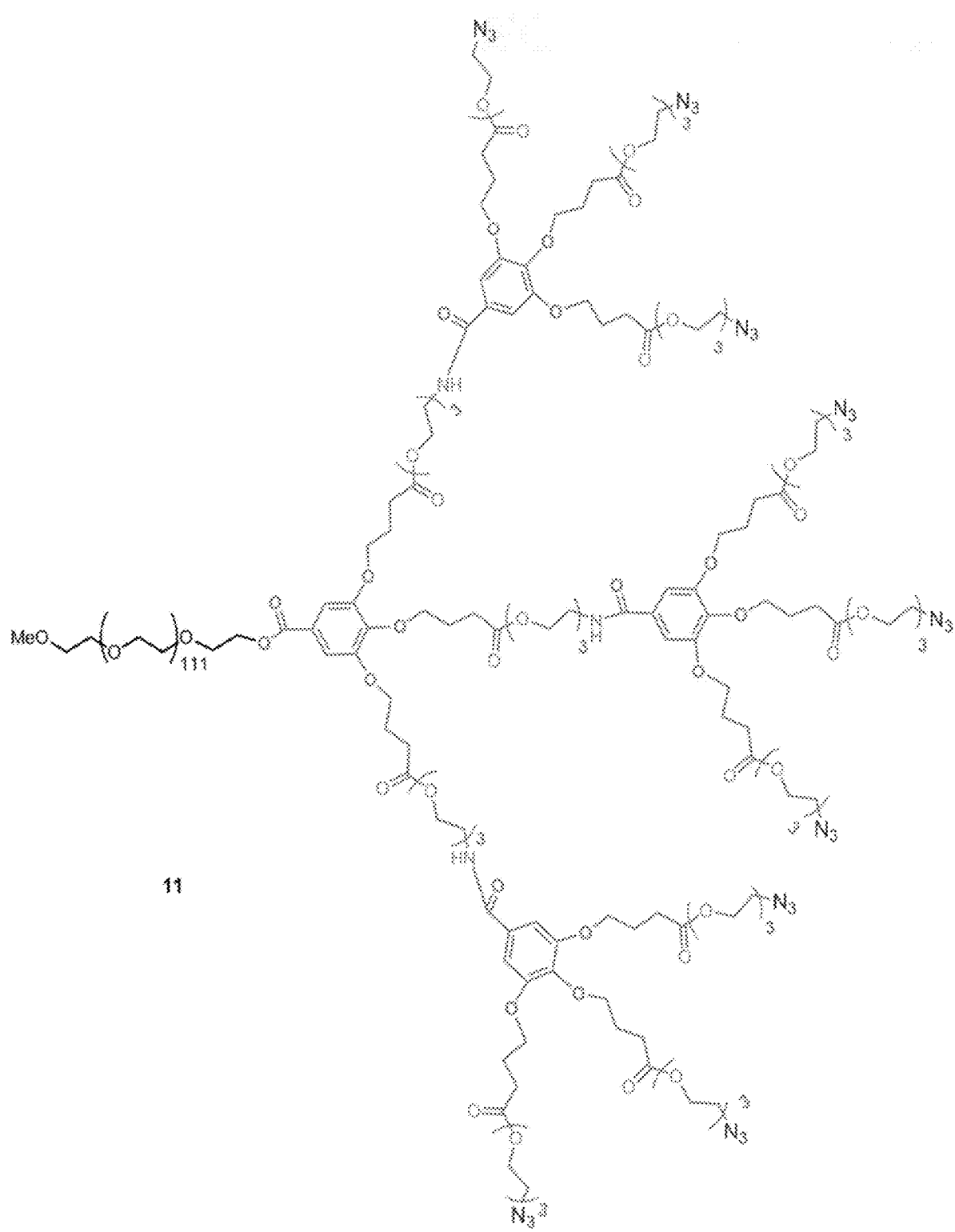
FIG. 41—Structure of G2 fully biodegradable PEG-fb-GATGE block copolymer (PEG-fb[G2]-N₃ 11) with polyethylene glycol 5000.
Figure 42:
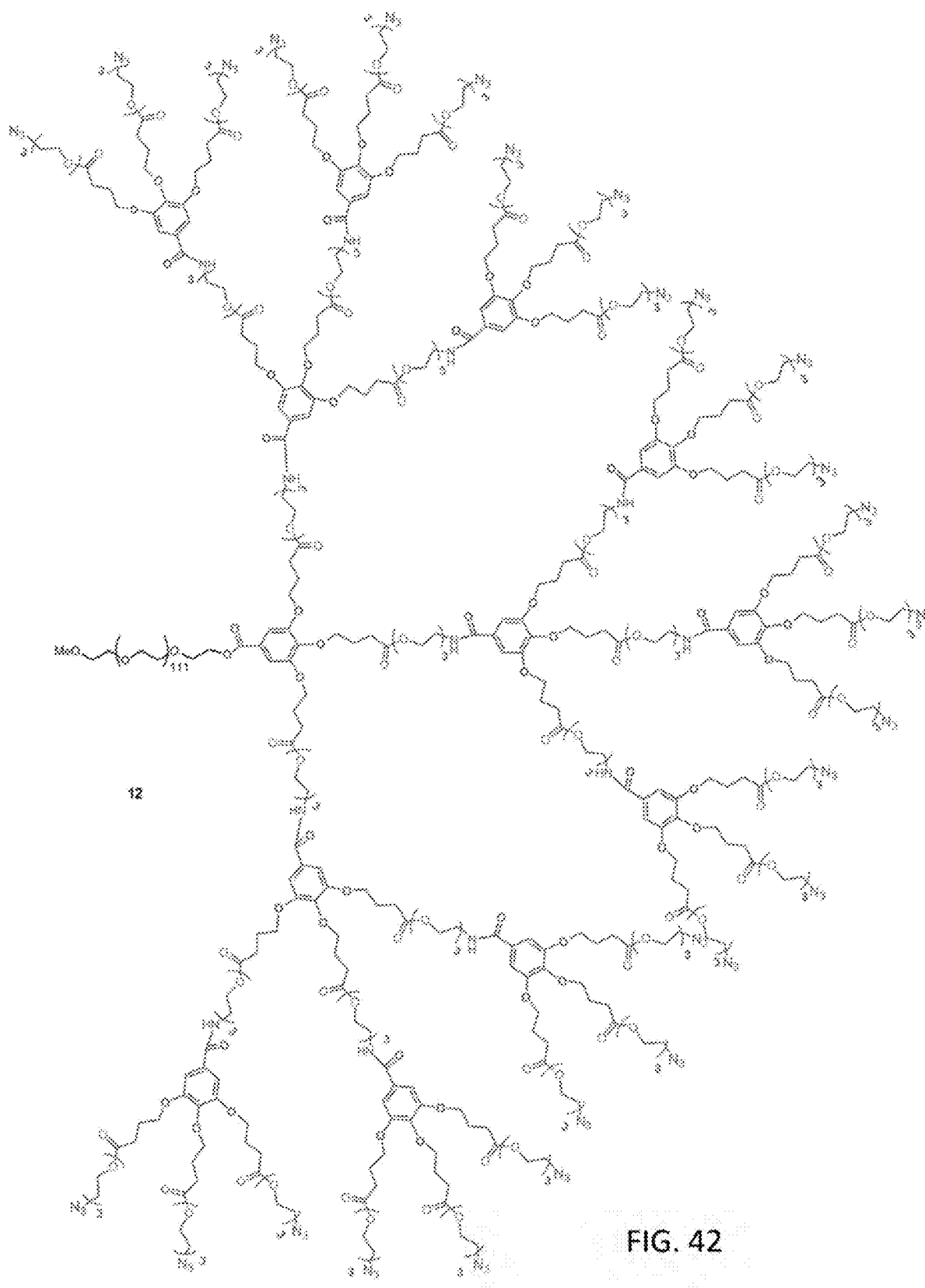
FIG. 42—Structure of G3 fully biodegradable PEG-fb-GATGE block copolymer (PEG-fb[G3]-N₃ 12) with polyethylene glycol 5000.
Figure 43:
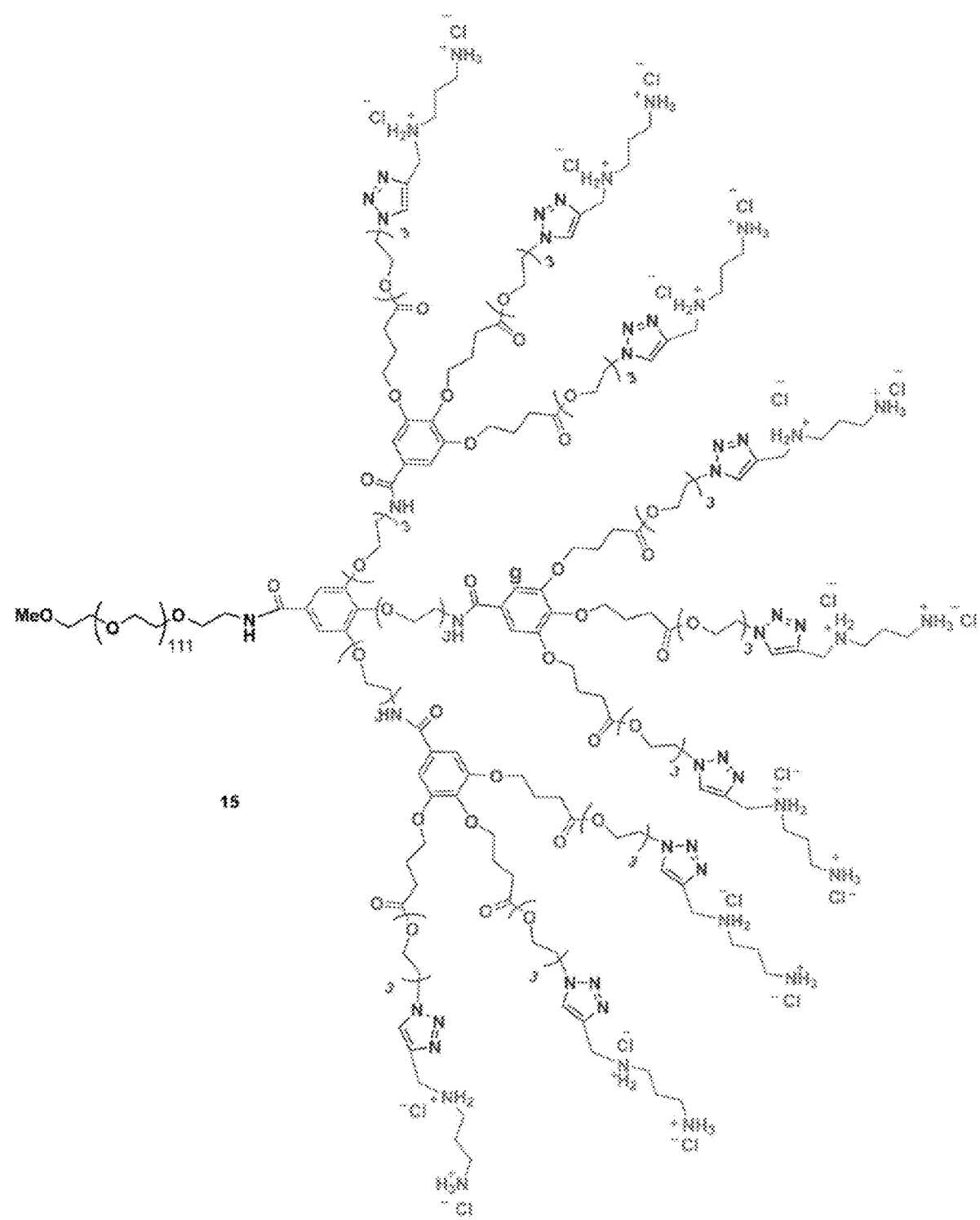
FIG. 43—Structure of G2 biodegradable PEG-GATGE block copolymer (bD 15) with polyethylene glycol 5000 and 1,3-propylene diamine-terminated.
Figure 44:
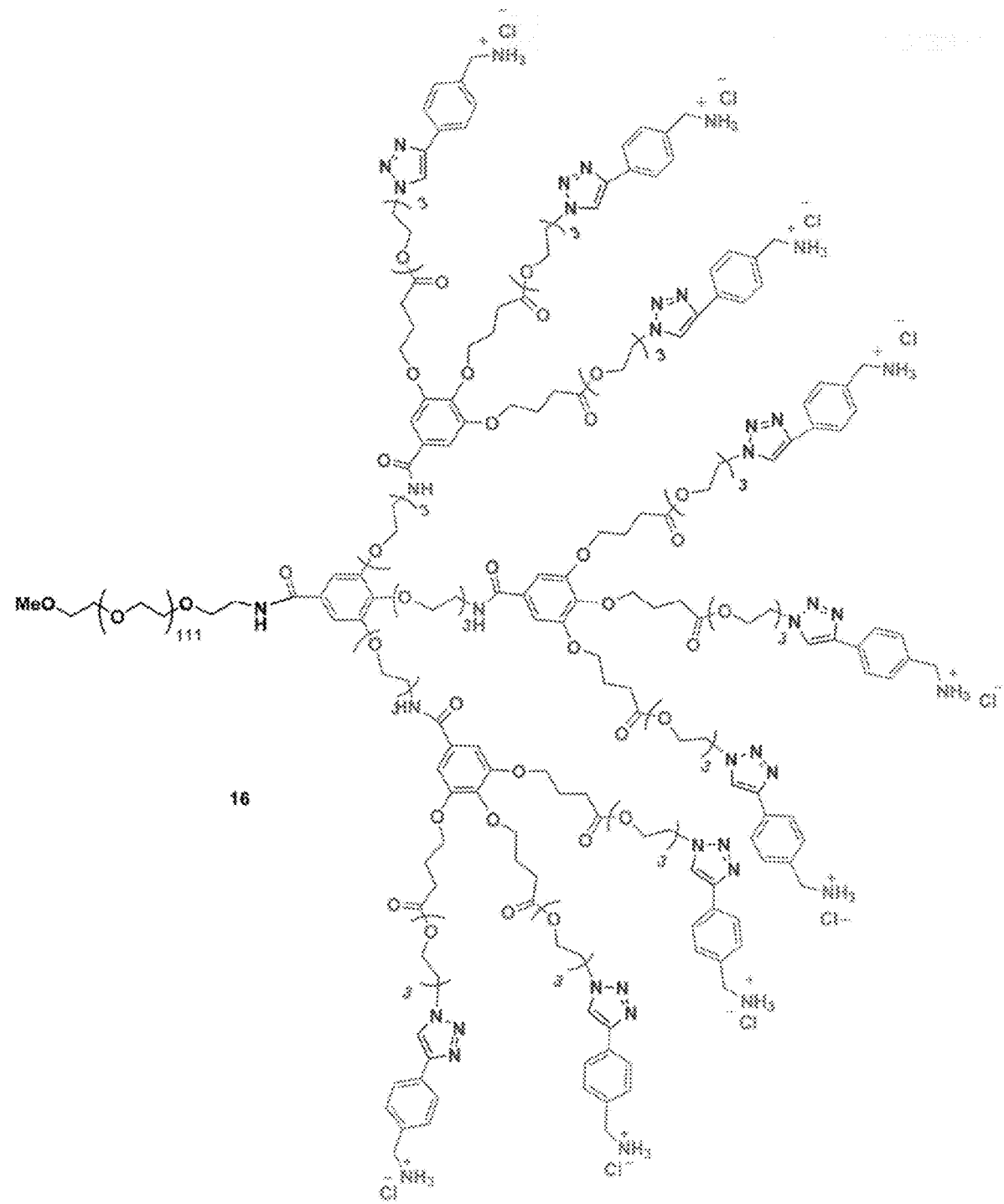
FIG. 44—Structure of G2 biodegradable PEG-GATGE block copolymer (bB 16) with polyethylene glycol 5000 and benzylamine-terminated.
Figure 45:
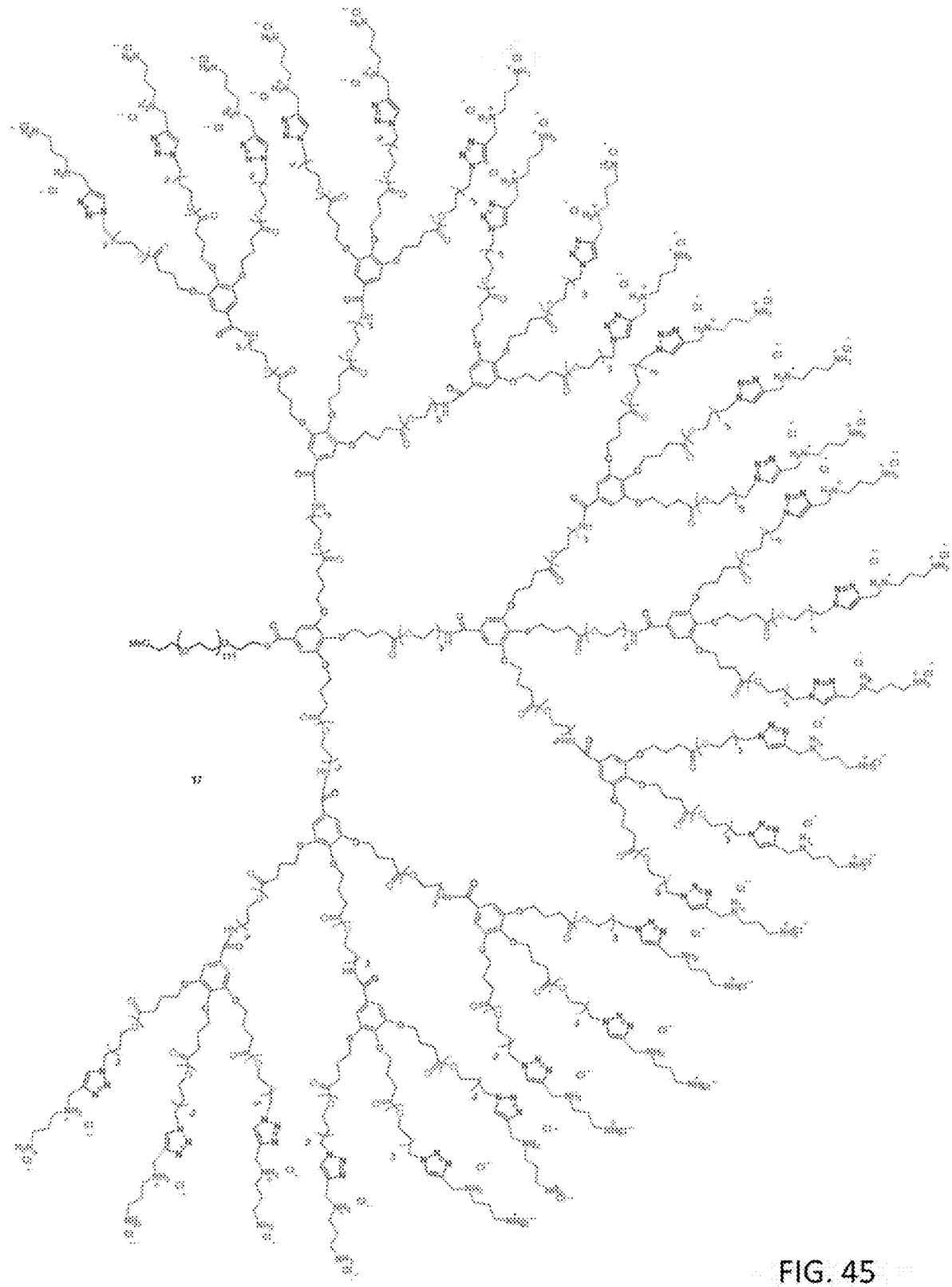
FIG. 45—Structure of G3 fully biodegradable PEG-GATGE block copolymer (fbD 17) with polyethylene glycol 5000 and 1,3-propyleneamine-terminated.
Figure 46:
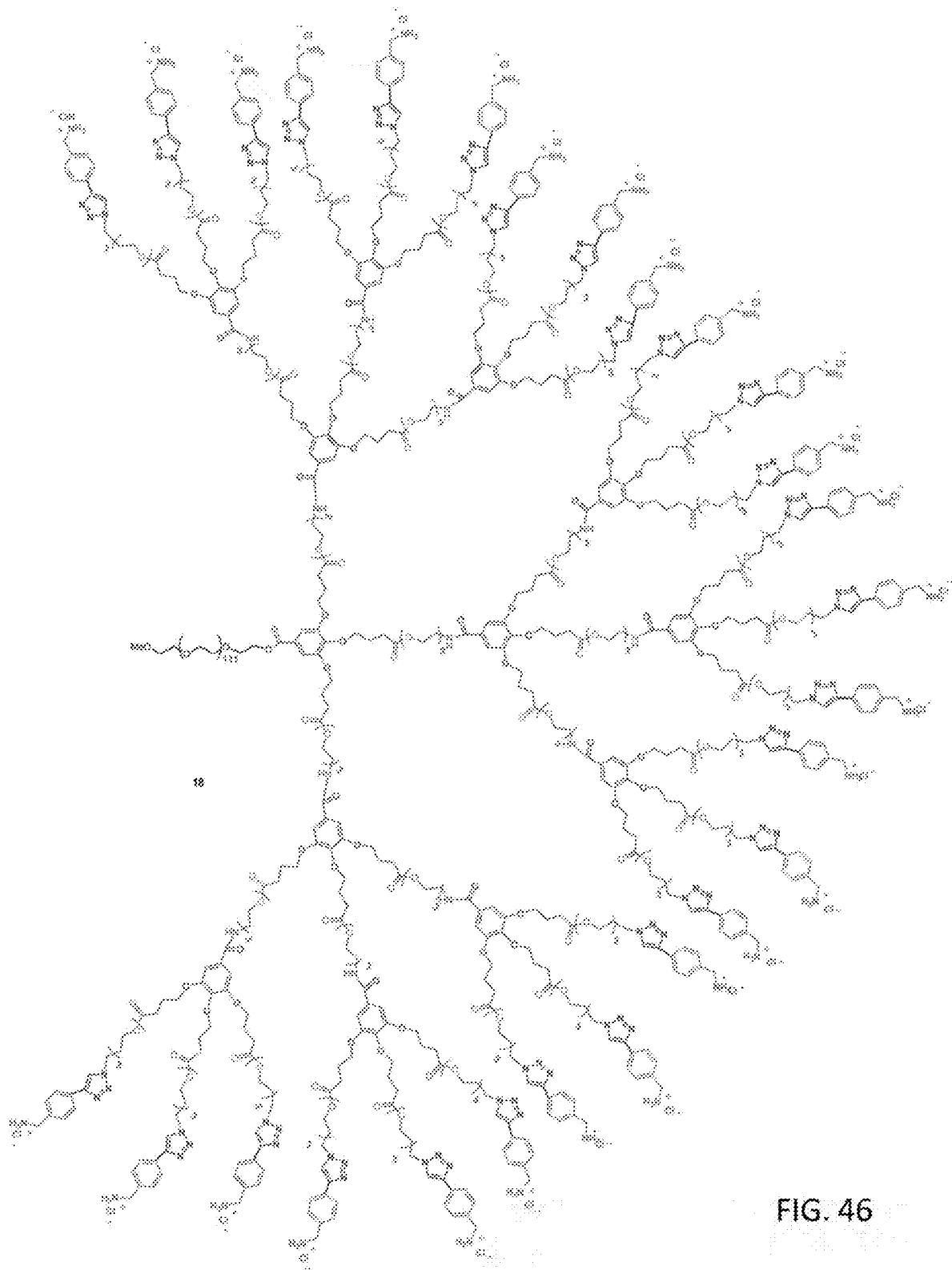
FIG. 46—Structure of G3 fully biodegradable PEG-GATGE block copolymer (fbB 18) with polyethylene glycol 5000 and benzylamine-terminated.
Figure 47:
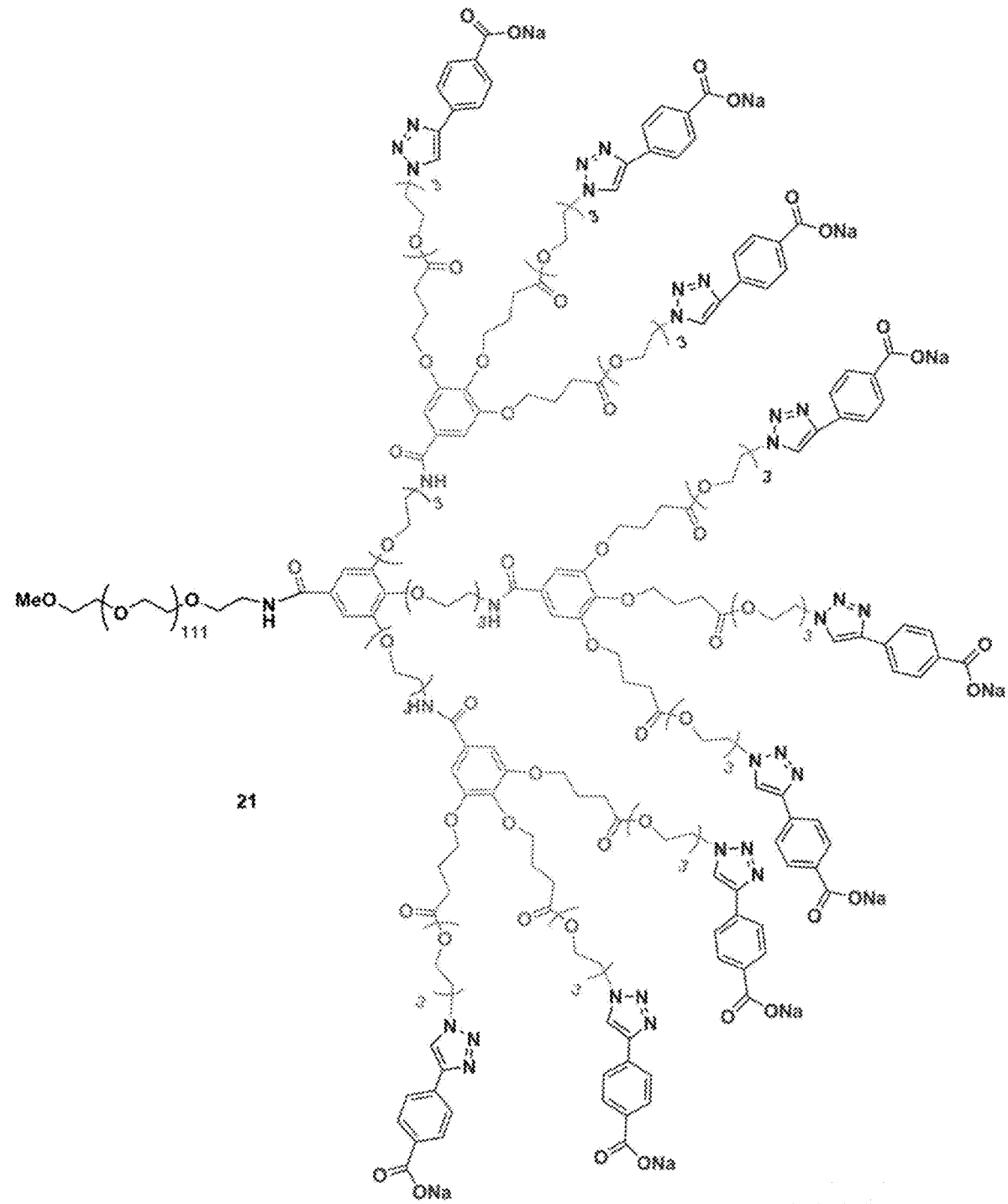
FIG. 47—Structure of G2 biodegradable PEG-GATGE block copolymer (bBz 21) with polyethylene glycol 5000 and benzoic acid-terminated.
Figure 48:
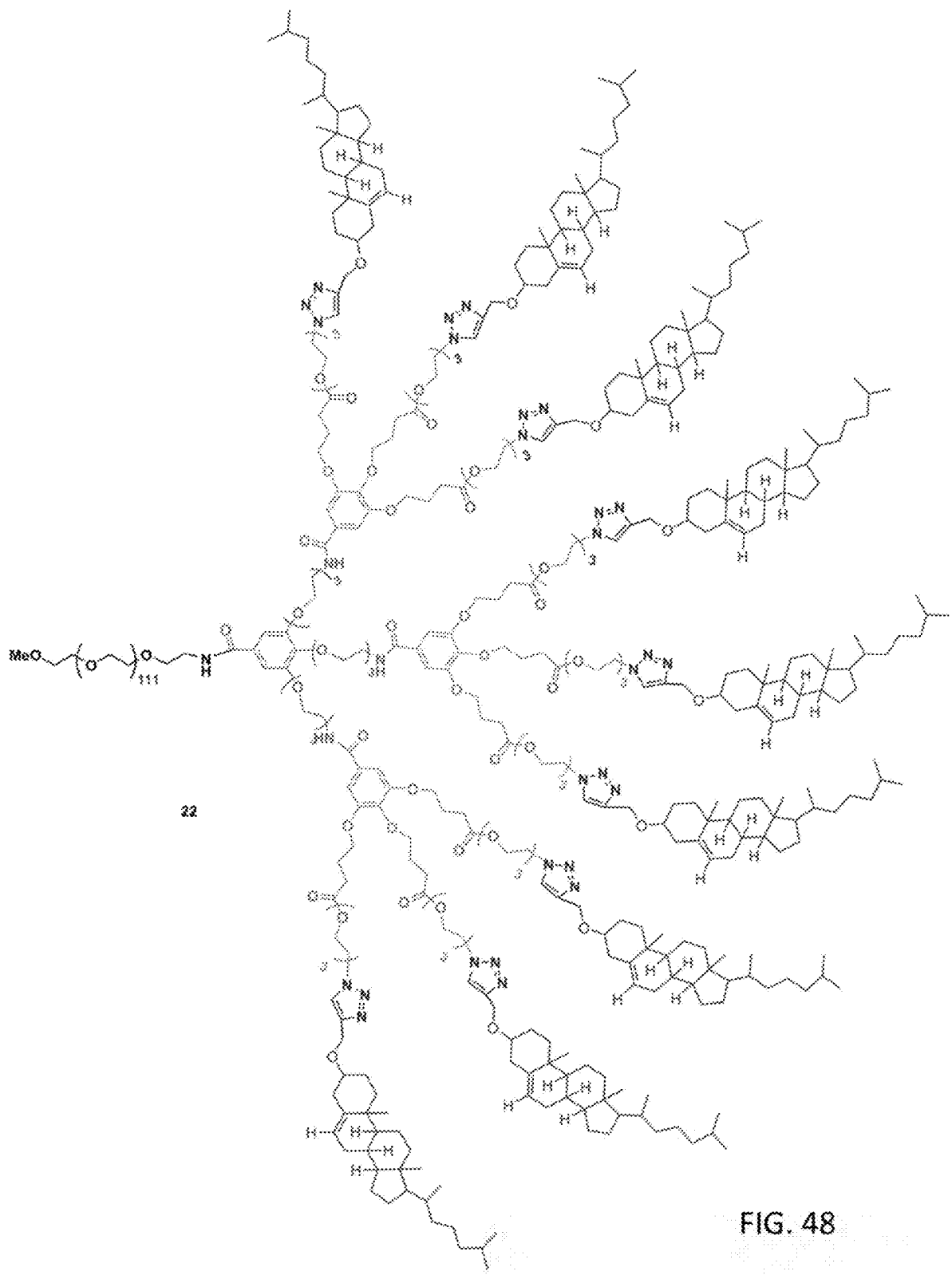
FIG. 48—Structure of G2 biodegradable PEG-GATGE block copolymer (bCh 22) with polyethylene glycol 5000 and cholesterol-terminated.
Figure 49:
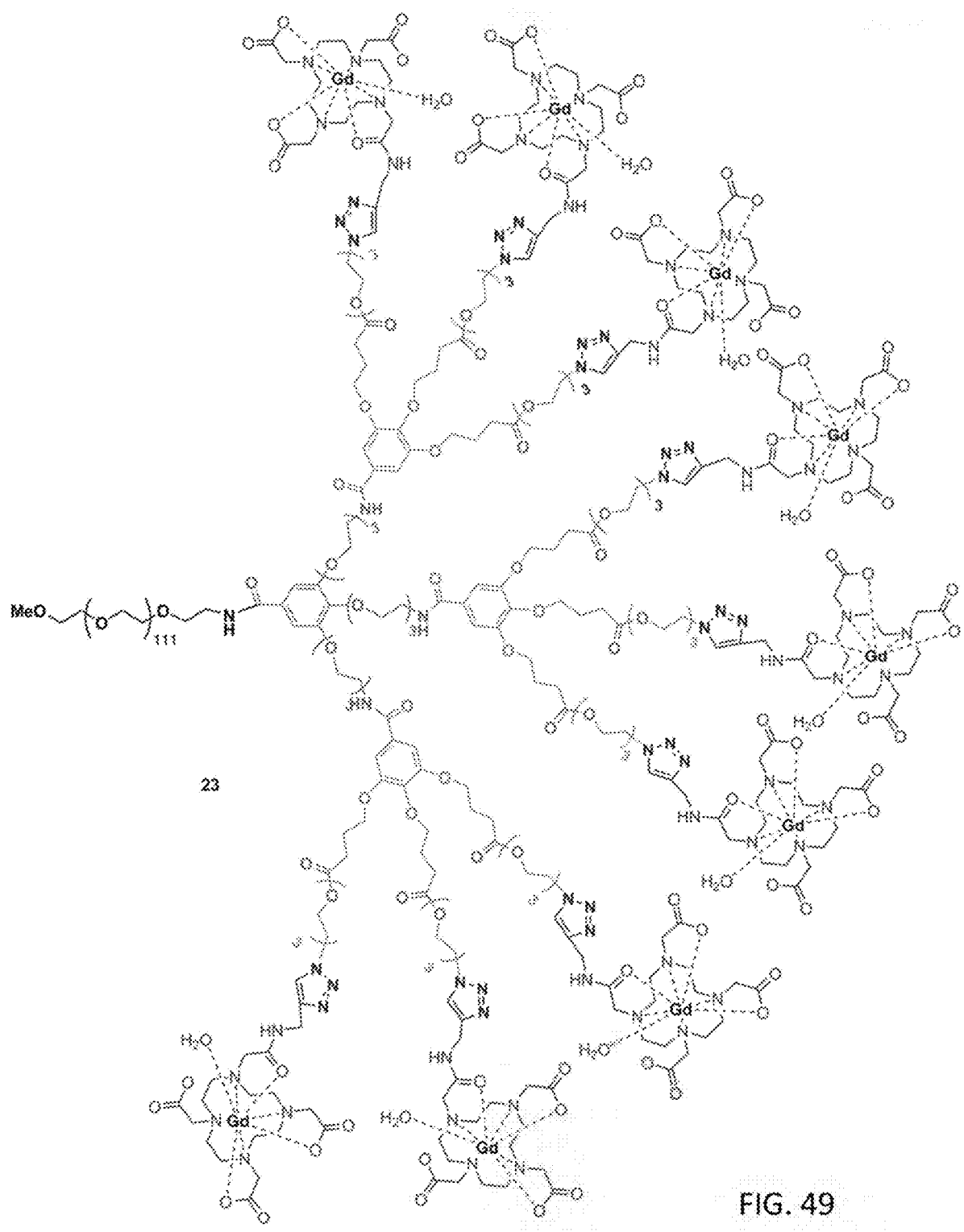
FIG. 49—Structure of G2 biodegradable PEG-GATGE block copolymer (bDO3A-Gd 23) with polyethylene glycol 5000 and DO3A-Gd-terminated. (DO3A-Gd=2,2',2"-(10-(2-(methylamino)-2-oxoethyl)-1,4,7,10-tetraazacyclododecane-1,4,7-triyl)-triacetate gadolinium (III) complex).
Figure 50:
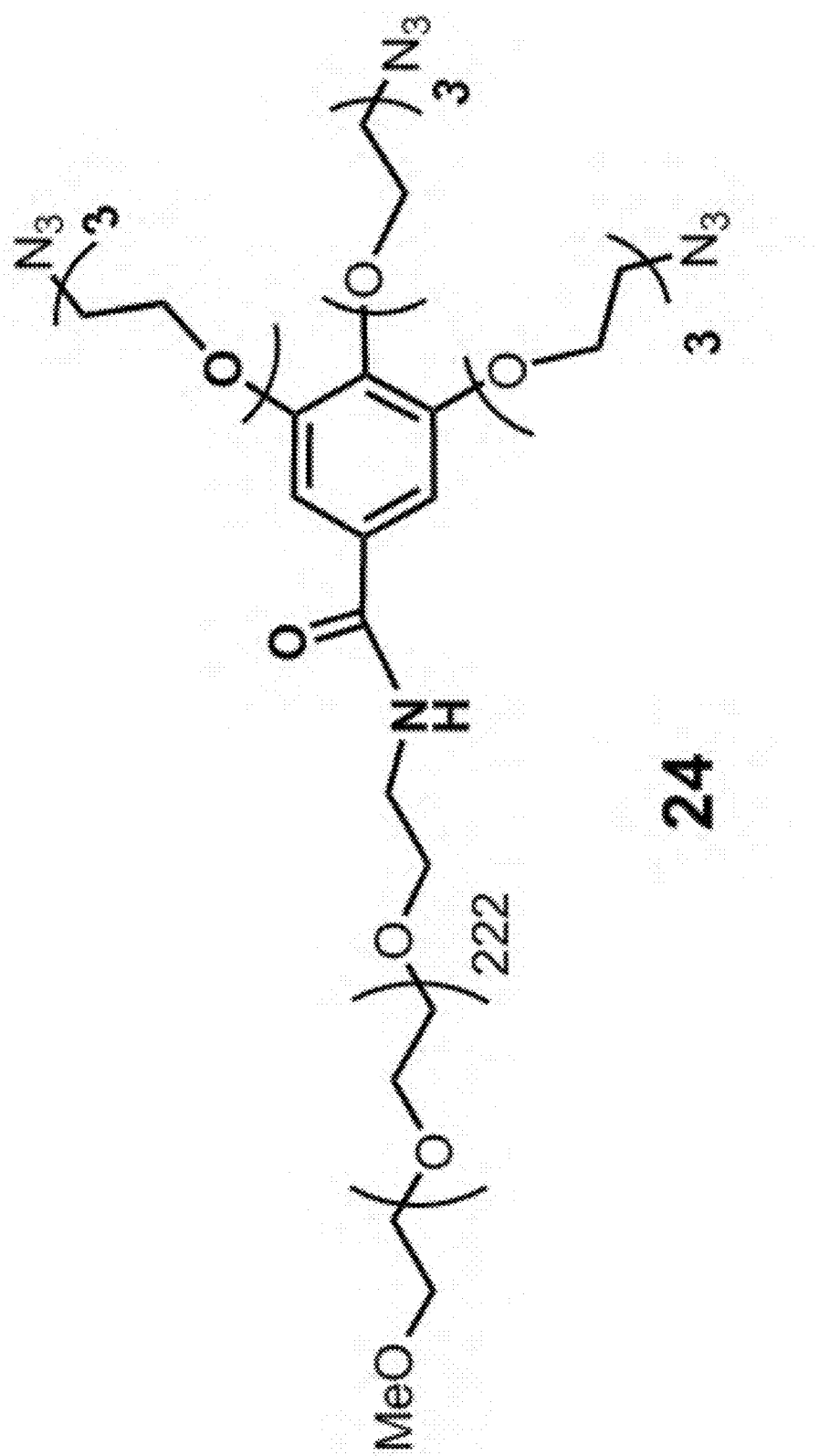
FIG. 50—Structure of G1 non-biodegradable PEG-GATGE block copolymer (PEG(10000)-[G1]-N₃ 24) with polyethylene glycol 10000.
Figure 51:
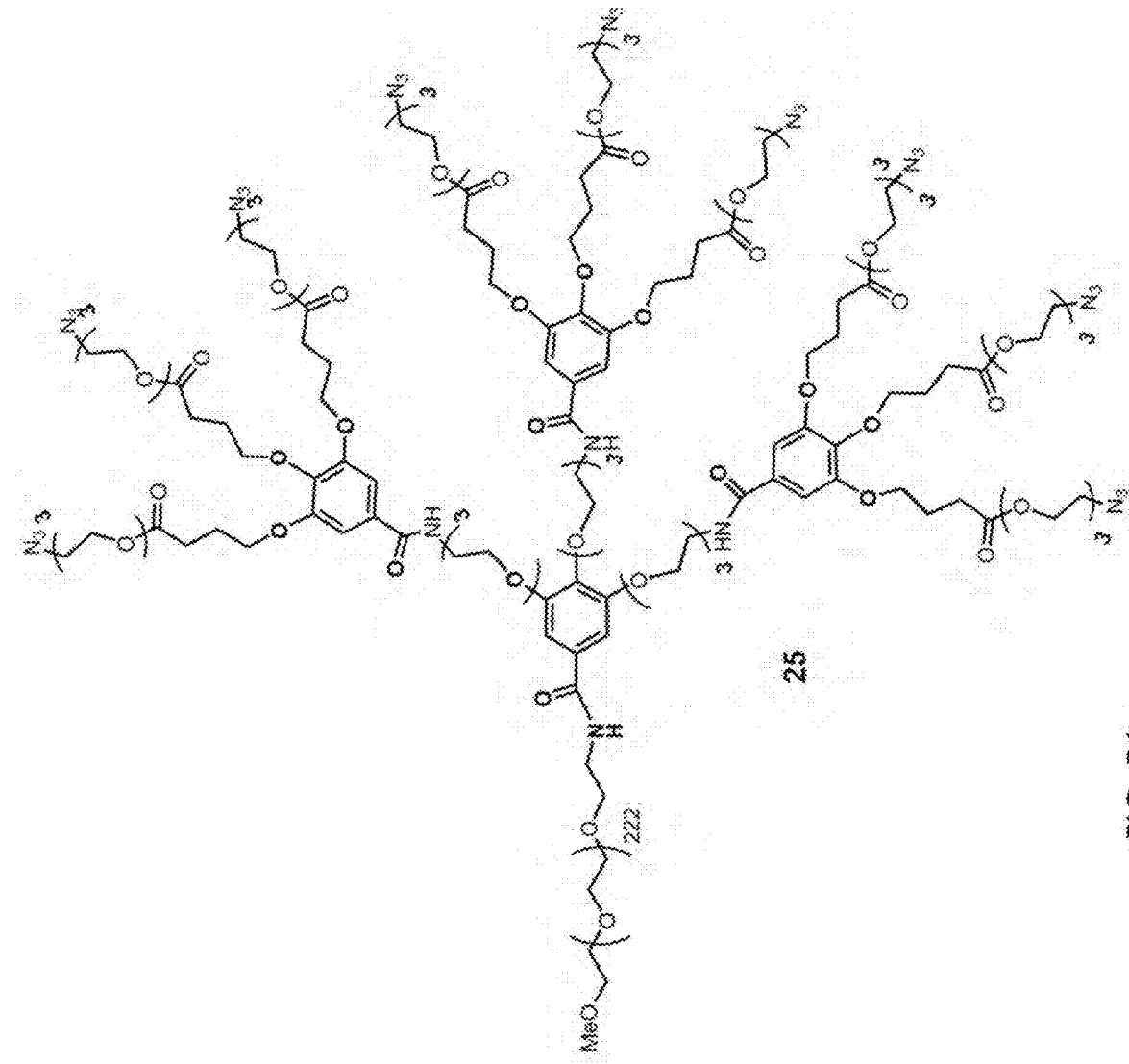
FIG. 51—Structure of G2 biodegradable PEG-GATGE block copolymer (PEG(10000)-b[G2]-N₃ 25) with polyethylene glycol 10000.

Dendriplexes degradation studies. In order to assess the siRNA released from the dendriplexes as a function of the time and at different pHs, bD and bB siRNA dendriplexes were incubated under acidic (pH 5.0) and physiological (pH 7.4) pH conditions for 1, 24 and 48 h. After that, dendriplexes were treated with heparin and the amount of siRNA released was determined by PAGE. The results show that a significant amount of siRNA has been released even after 1 h of incubation (FIGS. 35A-35B). This was particularly noteworthy at pH 7.4, in agreement with the higher percentage of degradation observed for the GATGE unit 6 (FIG. 2B) at pD 7.4.

Observing the degradation studies as a whole, it could be concluded that the hydrolysis rate for the dendritic structures (section 3.1 and FIG. 2B, section 3.2, and FIG. 3I) is slower than those for the dendriplexes. However, one must take into consideration that buffers for both experiments are prepared in different isotopic types of water: deuterated water for the degradability studies by NMR of the dendritic structures, while "normal" water was used for the dendriplex degradation studies by PAGE. As previously discussed, the catalysis rate can be significantly different in both media due to the kinetic isotope effect.[17] Moreover, and regardless of this isotopic effect, only a "low" percentage of degradation in the arms of each PEG-dendritic block copolymer can lead to a "high" instability of the dendriplexes (formed between several PEG-GATGE molecules and several siRNA molecules), which in turn can lead to a significant amount of released siRNA, as showed in FIGS. 35A-35B.

Overall these results confirm that the functionalization of the copolymers with both amino groups results in well-defined dendriplexes, with suitable properties for cellular uptake and siRNA delivery.

In an embodiment, the biological performance evaluation was carried out. All copolymers were evaluated on their cytotoxicity, ability to protect siRNA from endonuclease degradation and transfection efficiency.

Figures 6A, 6B:
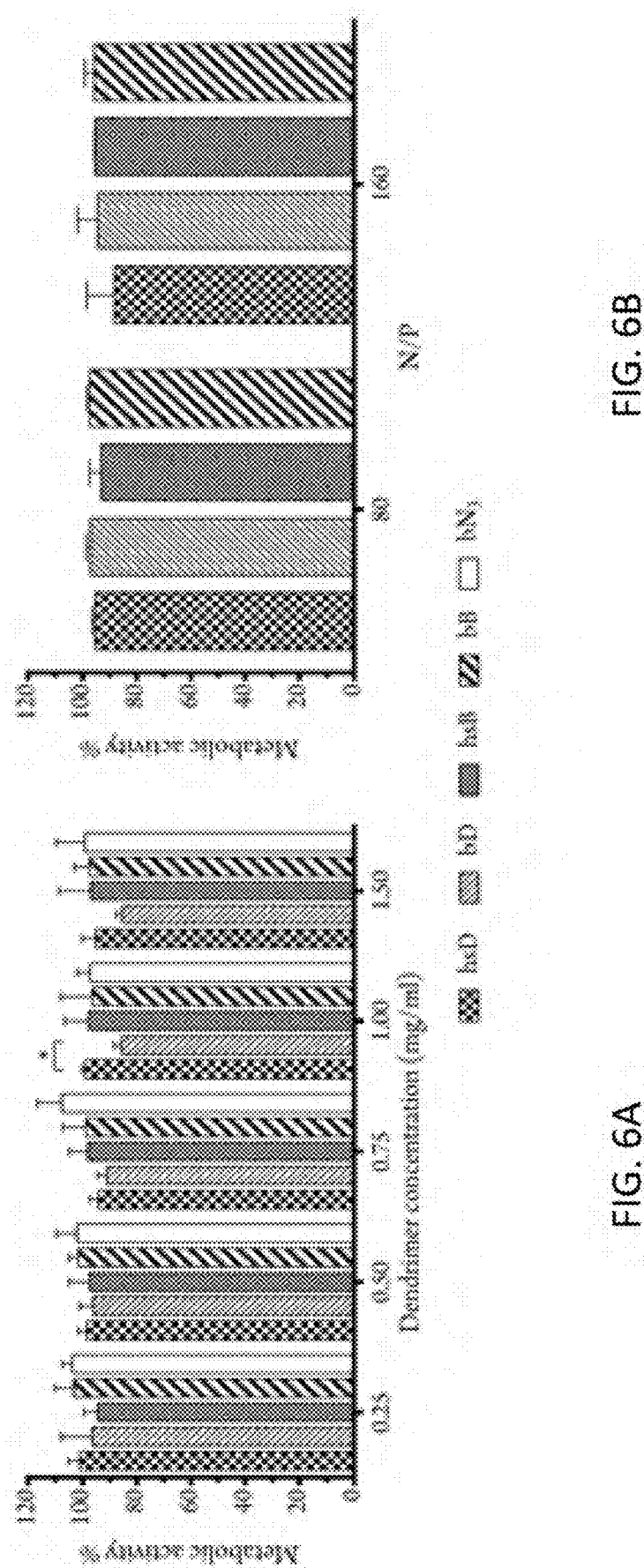
FIGS. 6A-6B—Relative metabolic activity (resazurin assay) using non-treated cells as a reference determined upon 24 h incubation of U2OS cells with: PEG-GATGE and PEG-GATG dendritic copolymers: azide- and amine-terminated (FIG. 6A). Dendriplexes at N/P 80 and 160 (equivalent to a copolymer concentration ca. 0.5 and 1 mg/mL, respectively) (FIG. 6B). Significant differences: *$p<0.05$ (one-way ANOVA test).

In an embodiment, the cell metabolic activity/cellular toxicity was carried out. Given that toxicity can represent a hurdle for the implementation of macromolecular systems in biomedicine, the cytotoxicity of the copolymers and dendriplexes was assessed in human osteosarcoma U2OS cells. Cytotoxicity was evaluated in terms of alterations in cell metabolic activity via a resazurin-based assay. For free azide- and amine-terminated copolymers (9, 15, 16, 19 and 20), the concentrations evaluated ranged between 0.25 and 1.5 mg/mL (FIG. 6A). In all cases, after 24 h of incubation, cell metabolic activity was higher than 85%, which indicates a low cytotoxic profile for these copolymers, even after functionalization with positive terminal groups. Subsequently, the toxicity of the dendriplexes potentially more toxic to the cells (N/P ratios of 80 and 160) was also tested. Here again, viabilities higher than 90% were obtained in all cases (FIG. 6B).

Figure 7:
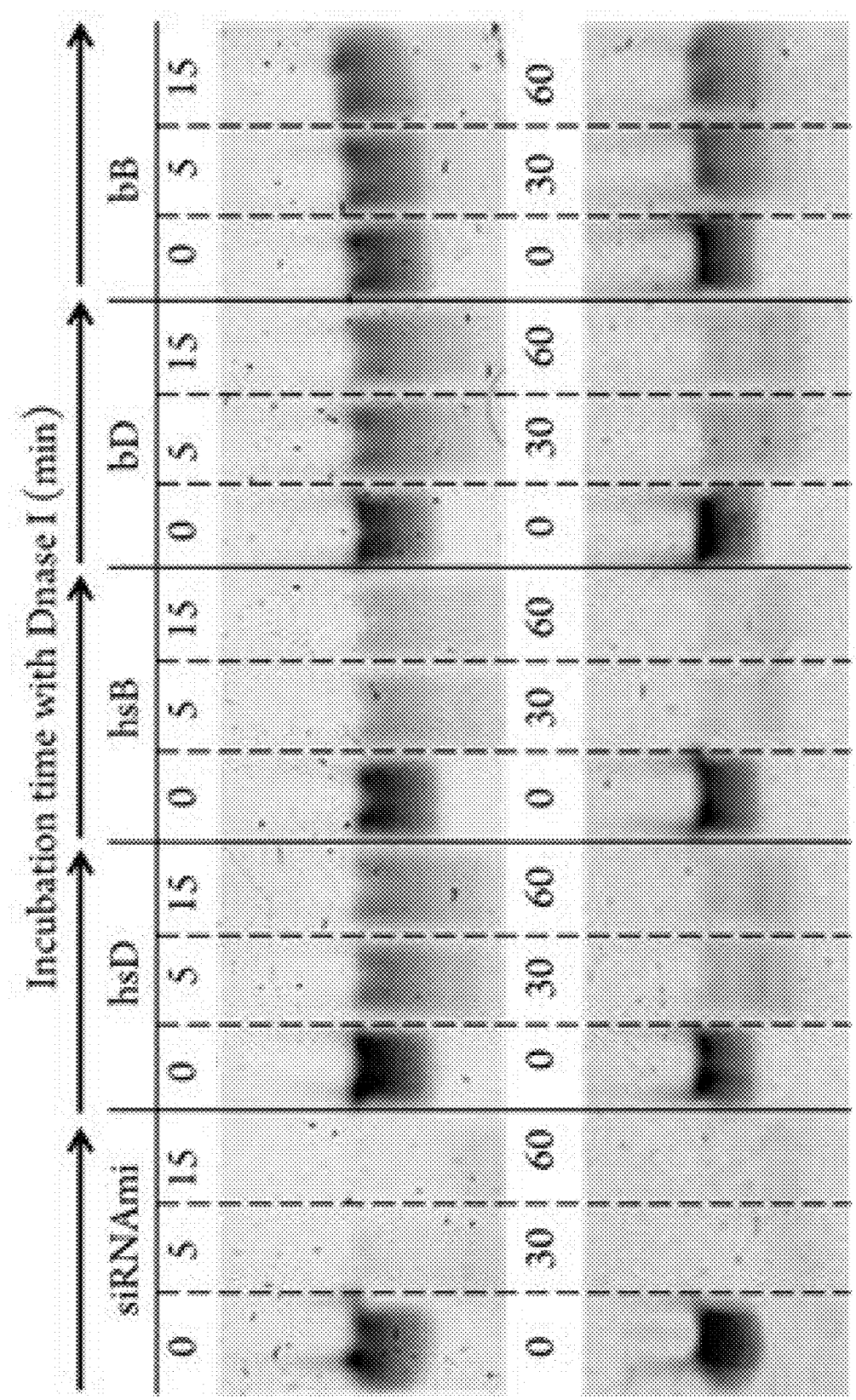
FIG. 7—siRNAmi degradation determined by PAGE after 0, 5, 15, 30 and 60 min of incubation with DNase I. Naked siRNAmi. N/P 160 dendriplexes with: hsD, hsB, bD and bB.

Endonuclease protection. siRNA protection from endogenous nucleases is a critical parameter in the development of new NA vectors. To this end, dendriplexes prepared from the four copolymers and siRNAmi at N/P 160 were incubated with an endonuclease for different periods (5-60 min). Then, after siRNAmi was displaced from the complexes with sodium dodecyl sulphate (SDS), samples were analyzed by PAGE (FIG. 7). While naked NA was completely degraded within 5 min, various degrees of siRNAmi protection were observed for the complexes with time. bB showed the highest protection capacity, with a notable level of unaffected siRNAmi even seen after 60 min of incubation. This points again to the relevance of the extra hydrophobic contribution provided by the aromatic benzylamine (B), that together with the hydrophobic spacers in GATGE, provide a very good protection of NA from degradation. Previous studies showed that amine-terminated PEG-GATG were not able to protect pDNA from degradation for periods longer than 5 min.[24] These results demonstrate the benefit of the peripheral functionalization with these aminated groups.

Figure 8A:
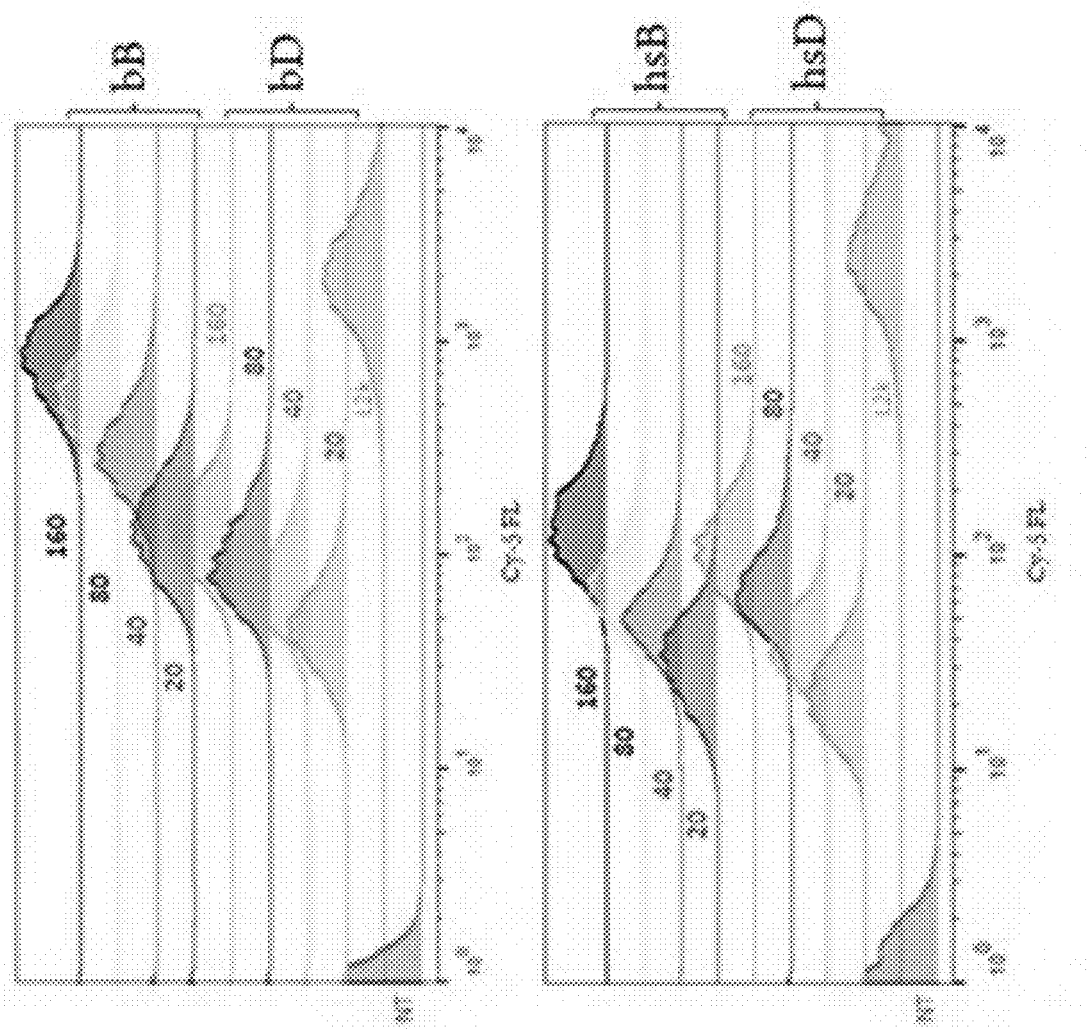
FIGS. 8A-8C—Cellular association of dendriplexes. Dendriplexes containing Cy5 labeled siRNAmi (Cy5-siRNAmi) were incubated for 24 h with U2OS cells at a final siRNAmi concentration of 0.1 μM. Lipofectamine® 2000 (L2k) was used as a control according to manufacturer instructions.

In an embodiment, the cellular association/uptake. The ability of the all developed dendriplexes hsD to associate and/or to cross the cell membrane was assessed. U2OS cells stably expressing the fusion protein eGFP-Luciferase (U2OS/eGFPLuc cells) were incubated for 24 h at 37° C. with the dendriplexes carrying a siRNAmi labelled with Cy5. Cells were analysed by fluorescence-activated cell sorting (FACS) and confocal fluorescence microscopy. For all cells treated with dendriplexes, FACS data (FIG. 8A) showed a shift to higher fluorescence intensity (FL) compared with untreated cells, as a result of dendriplex cell association/internalization. Higher FL values correlated with an increase in the N/P ratio, what can be explained by a higher NA protection in the dendriplexes. For all vectors, the percentage of positive cells was always above 95% (Table 1). bB (N/P 80 and 160) showed the highest efficiency of internalization with the FL values closer to Lipofectamine® 2000 (L2k), a gold standard agent for in vitro transfection (FIG. 8A).

TABLE 1

Percentage of cells with associated dendriplexes (positive cells) by flow cytometry

| Treatment | N/P | % Positive Cells |
|---|---|---|
| NT | | 0.38 |
| L2k | | 99.2 |
| hsD | 20 | 96.4 |
| | 40 | 98.8 |
| | 80 | 98.7 |
| | 160 | 99.3 |
| bD | 20 | 98.2 |
| | 40 | 98.2 |
| | 80 | 98.3 |
| | 160 | 98.2 |
| hsB | 20 | 98.3 |
| | 40 | 99.0 |
| | 80 | 99.1 |
| | 160 | 99.1 |
| bB | 20 | 98.1 |
| | 40 | 98.1 |
| | 80 | 98.2 |
| | 160 | 98.8 |

Figure 8B:
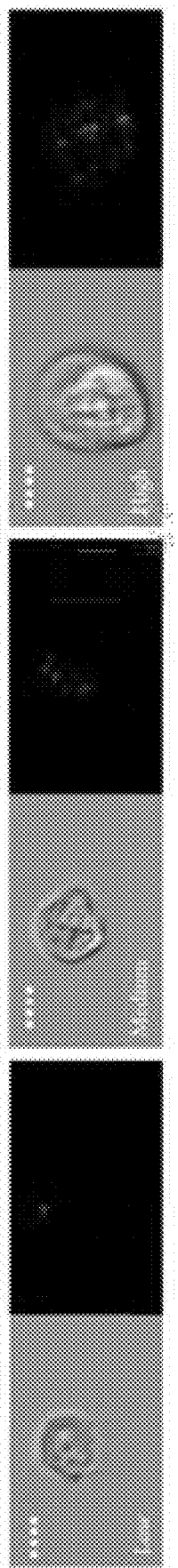

The internalization of dendriplexes was further quantified and characterized by imaging flow cytometry, as this technique allows the distinction between nanoparticles only associated to the cell membrane from nanoparticles present in the cell cytoplasm(internalized). The percentage of positive cells was always above 95% (Table 2), confirming that after 24 h of contact the dendriplexes were already fully internalized. For all copolymers, the percentage of dendriplex-loaded vesicles (DLVs) per cell (Table 3 and FIGS. 36A-36D) was determined. Cell images were taken in several different planes on the z axis and an image projection was created. Three groups defining cells with low (<1.5), medium (1.5-5.5) or high (>5.5) number of DLVs per cell were determined (FIG. 8B as well as Table 3 and FIGS. 36A-36D). It was found that biodegradable copolymers showed higher relative internalization efficiency than their hydrolytically stable counterparts. bB was the copolymer with the highest percentage of cells with high number of DLVs (44%) (FIG. 8B and Table 3).

TABLE 2

Percentage of cells with internalized dendriplexes (positive cells) at N/P 160 by imaging flow cytometry

| Treatment | % Positive Cells |
|---|---|
| NT | 0.4 |
| L2K | 98.7 |
| hsD | 99.0 |
| bD | 94.6 |
| hsB | 99.8 |
| bB | 99.8 |

TABLE 3

Dendriplex-loaded vesicles (DLVs).

| | Dendriplex-loaded Vesicles (DLV) | | |
|---|---|---|---|
| Copolymer | Low (<1.5 spots) | Medium (1.5 – 5.5 spots) | High (>5.5 spots) |
| hsD | 23% | 62% | 15% |
| hsB | 13% | 63% | 24% |
| bD | 16% | 51% | 33% |
| bB | 4% | 52% | 44% |

Further, confocal microscopy images of U2OS cells reveal a dotted-like Cy5 fluorescence pattern indicative of an endosomal uptake of the dendriplexes (FIG. 8B).

The increased NA protection capacity in the bB dendriplexes imparted by the GATGE units and benzyl groups may justify the highest uptake mediated by this system in two ways: i) better siRNA protection means that more of the intact labelled Cy5-siRNA will be able to enter the cell; ii) the extra hydrophobicity imparted by the GATGE can improve cell membrane interactions and assist in internalization.

Figures 9A, 9B:
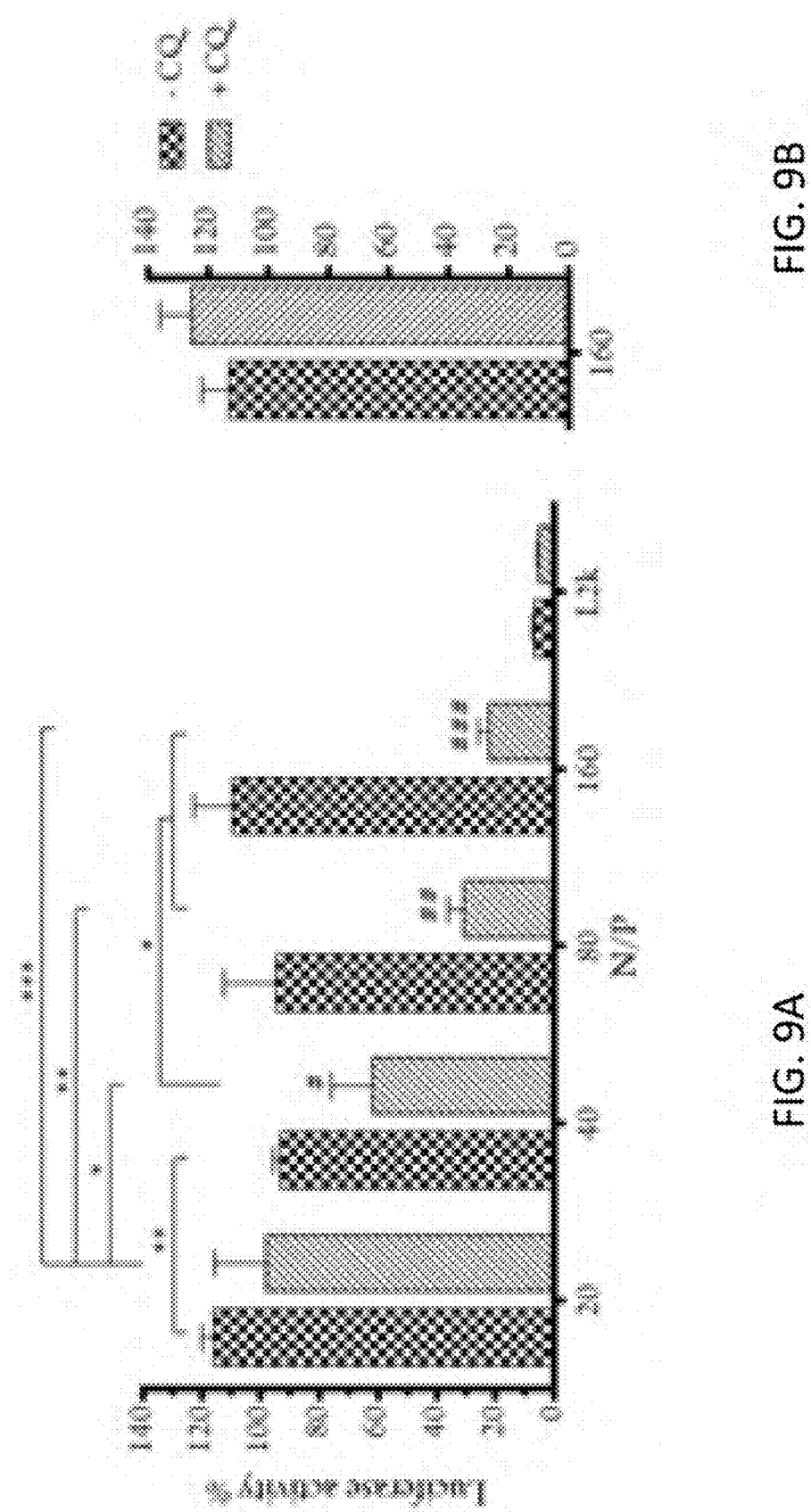
FIGS. 9A-9C—Percentage of Luciferase activity upon 72 h post-transfection for: anti-eGFP siRNA/bD dendriplexes at different N/P, and L2k (FIG. 9A). non-coding siRNA/bD dendriplex at N/P 160. Experiments in the absence (−) and presence (+) of CQ (FIG. 9B). Hydrolytically stable and biodegradable anti-eGFP siRNA/PEG-GATG dendriplexes: hsD, bD, hsB, bB at N/P 160 (FIG. 9C). (Experiments in the absence (−) and presence (+) of CQ). Significant differences: *$p<0.05$, $p<0.01$ and *$p<0.001$ (one-way ANOVA tests). For each N/P, the symbol # indicates significant differences between experiments in the absence and presence of CQ.
Figure 9C:
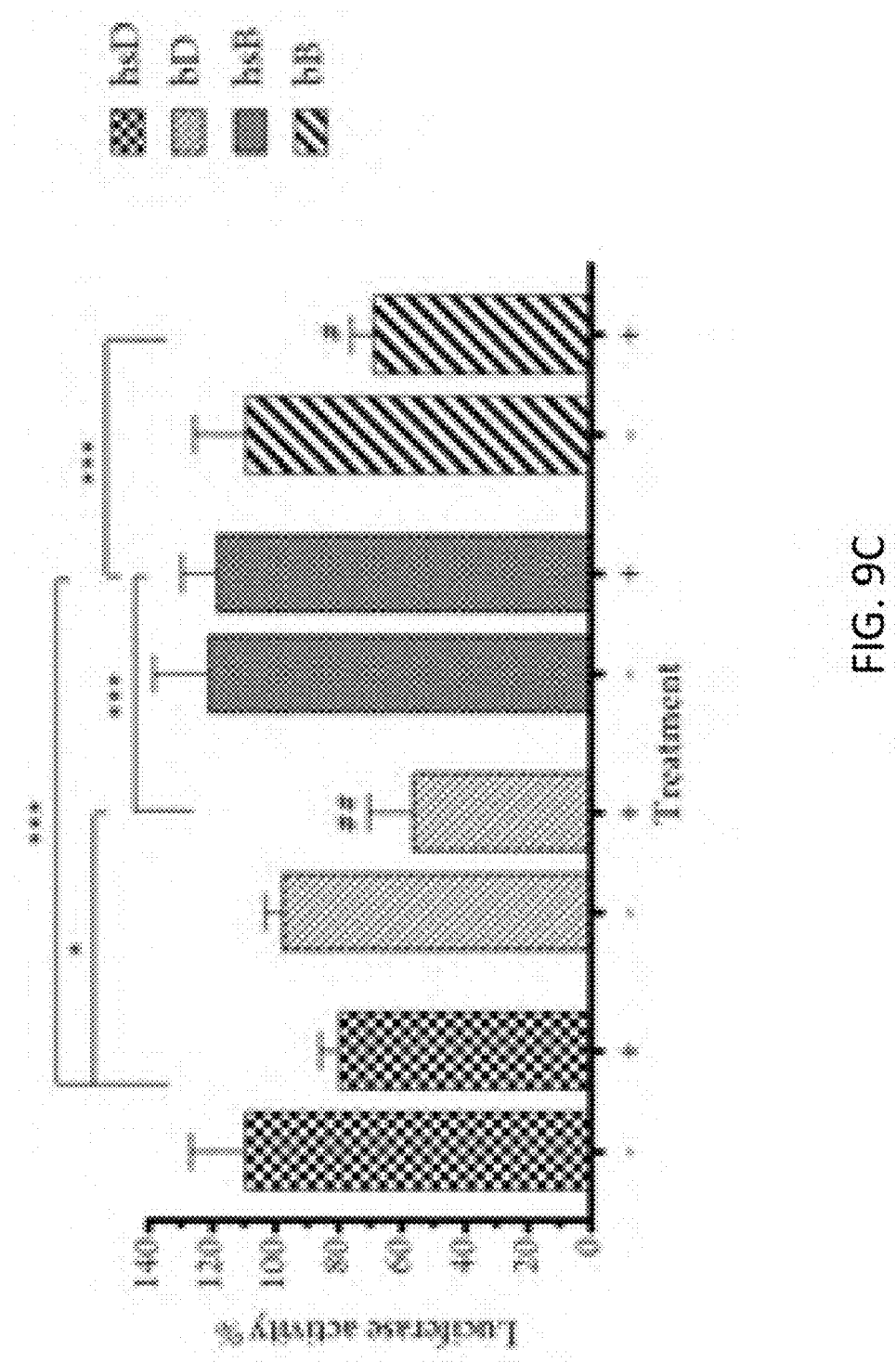
Figure 10:
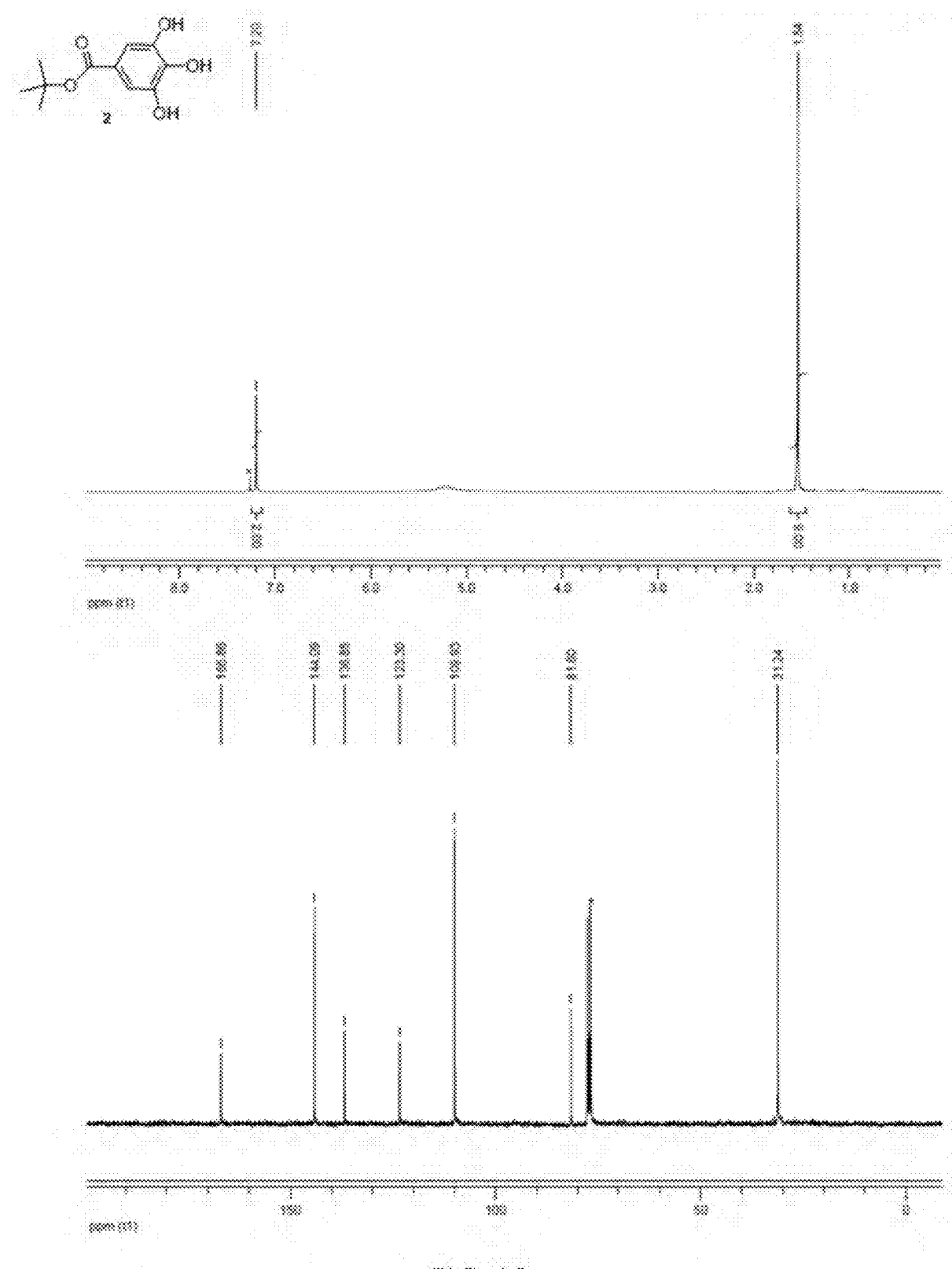
FIG. 10—$^1$H and $^{13}$C NMR Spectra of tert-butyl gallate (2).
Figure 11:
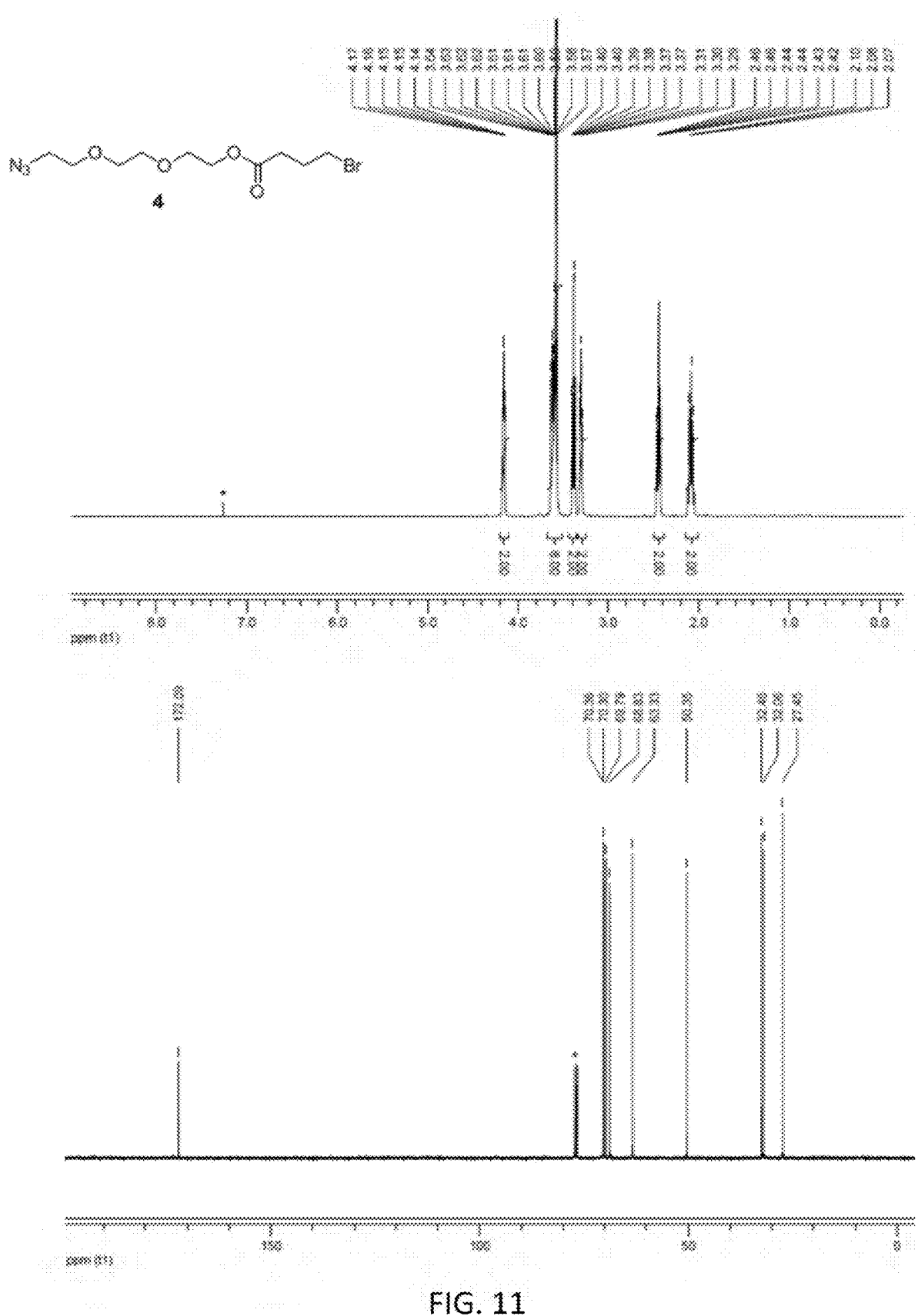
FIG. 11—$^1$H and $^{13}$C NMR spectra of 2-[2-(2-azidoethoxy)ethoxy]ethyl 4-bromobutanoate (4) Tris{2-[2-(2-azidoethoxy)ethoxy]ethyl} 4,4',4"-{[5-(tert-butoxycarbonyl)benzene-1,2,3-triyl]tris(oxy)}tributanoate.
Figure 12:
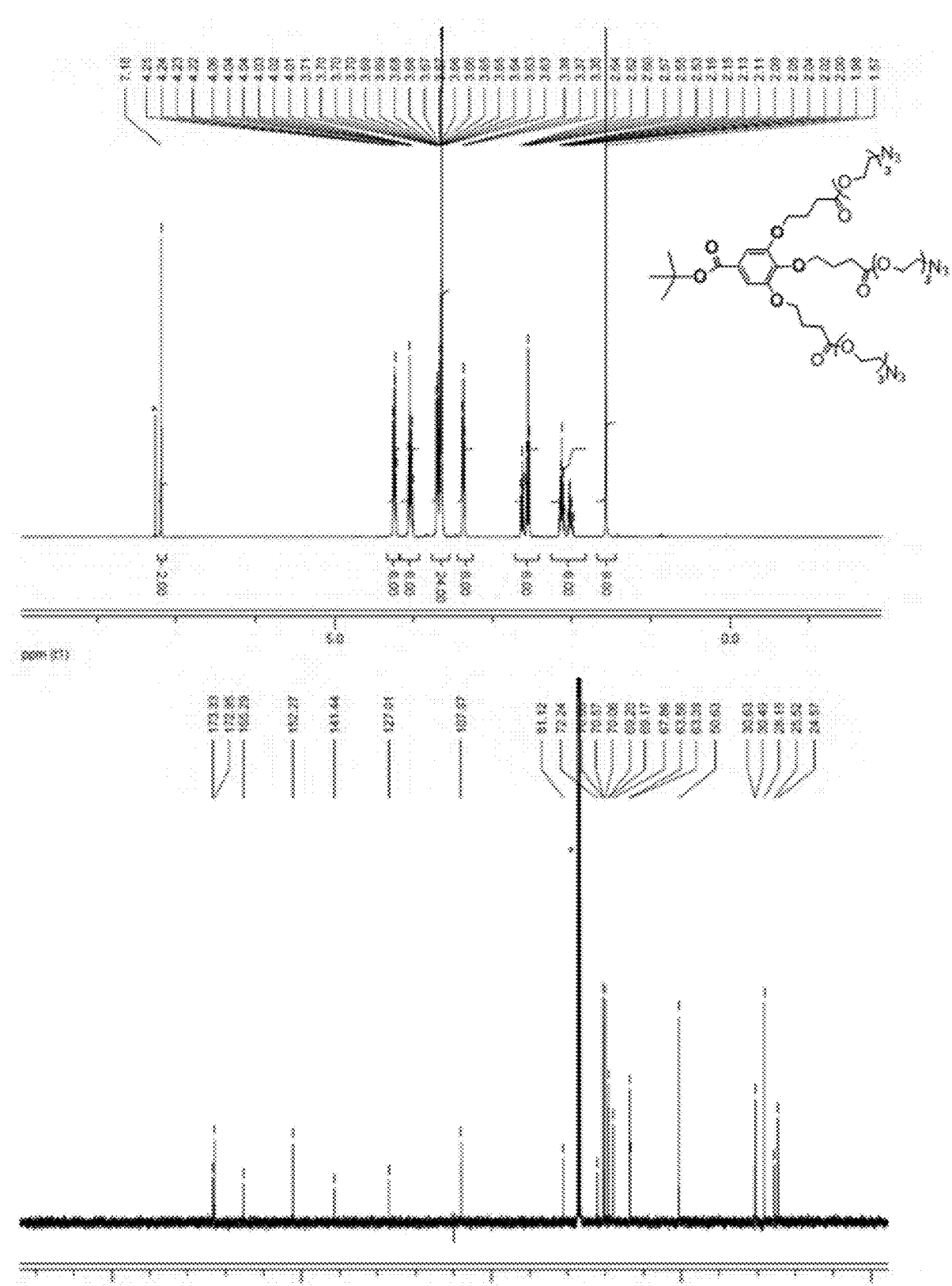
FIG. 12—$^1$H and $^{13}$C NMR spectra of tris{2-[2-(2-azidoethoxy)ethoxy]ethyl} 4,4',4"-{[5-(tert-butoxycarbonyl)benzene-1,2,3-triyl]tris(oxy)}tributanoate FIG. 13—$^1$H and $^{13}$C NMR spectra of 3,4,5-tris(4-{2-[2-(2-azidoethoxy)ethoxy]ethoxy}-4-oxobutoxy)benzoic acid (5) (GATGE building unit)
Figure 13:
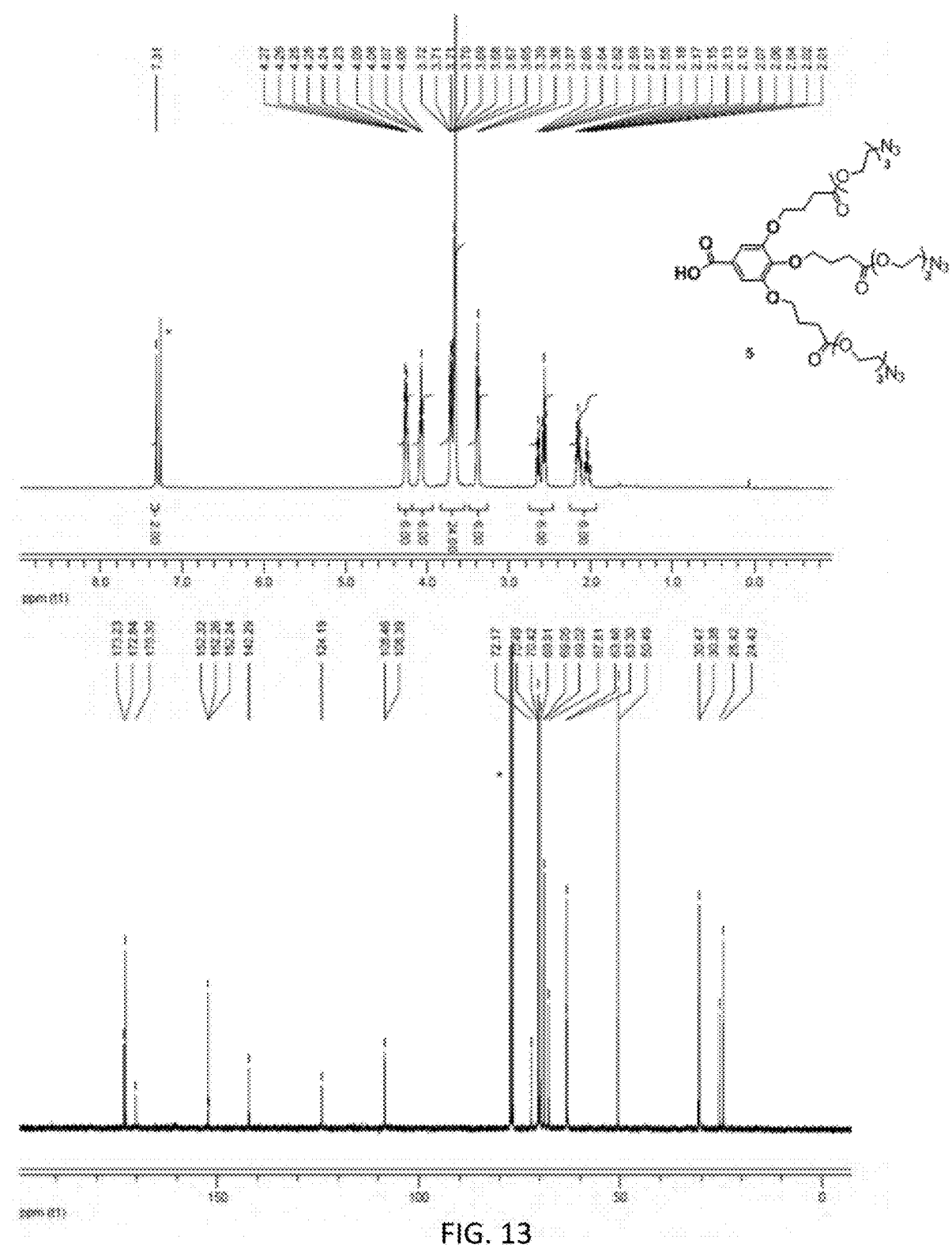
Figure 14:
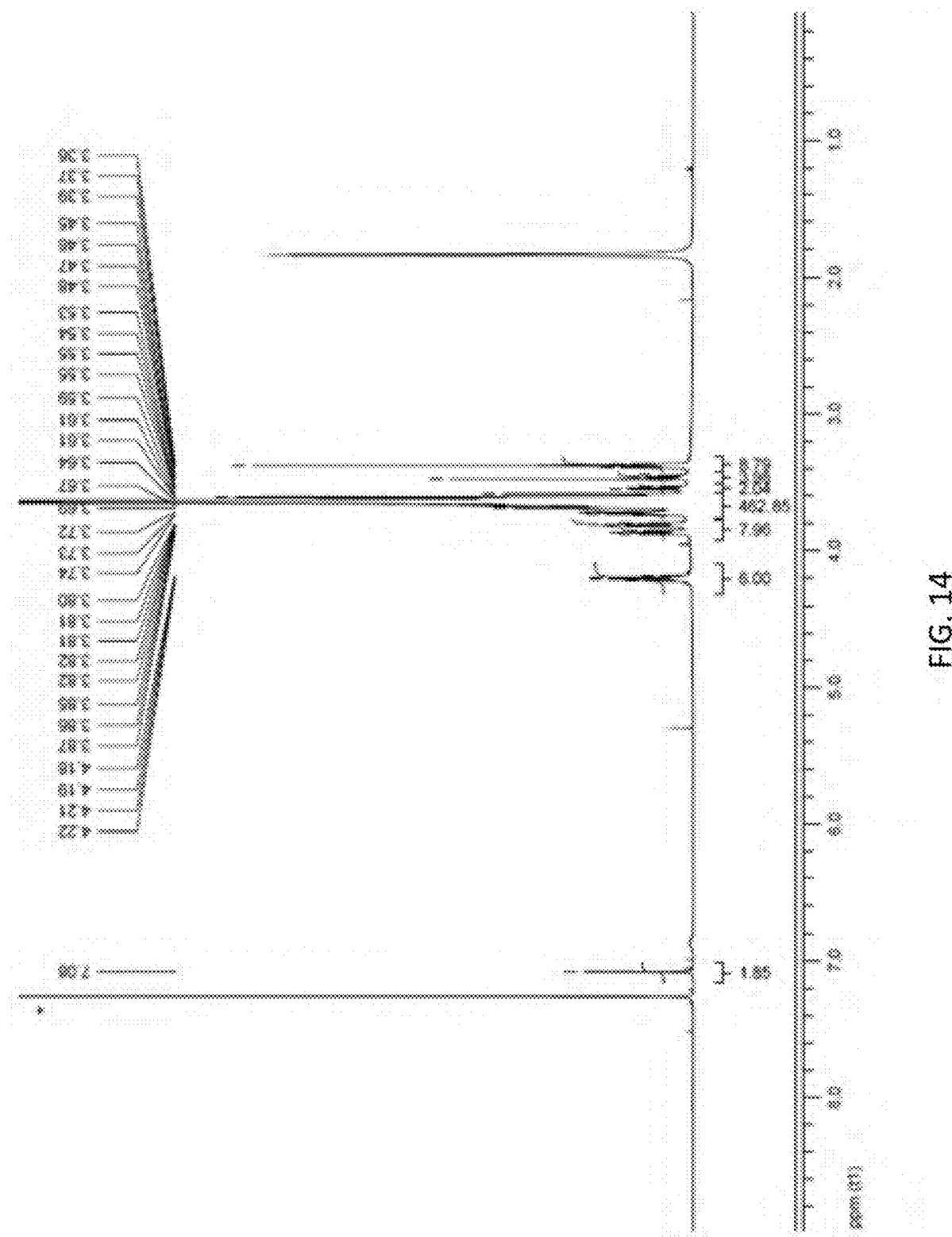
FIG. 14—$^1$H NMR spectrum of PEG-[G1]-$N_3$ (8).

In an embodiment, the transfection Efficiency was as follows. The ability of the dendriplexes to mediate gene silencing was tested in U2OS/eGFPLuc cells. Cells were incubated for 24 h at 37° C. with dendriplexes containing an anti-eGFP siRNA (FIGS. 9A and 9C) and with dendriplexes complexing a non-coding siRNA (negative control, FIG. 9B). Transfection efficiency was assessed by the decrease of luciferase activity relative to non-treated cells. When cells were treated with bD dendriplex complexing the non-coding siRNA (N/P 160) an increase in luciferase activity was observed (FIG. 9B), an effect that can be ascribed to influences of the vector on promoter activity.[25] Experiments performed with a nti-eGF P siRNA dendriplexes based on bD at several N/P afforded a small decrease on luciferase activity (FIG. 9A), in agreement with previous reports from other groups.[13,26] To explore if these results pointed to an impairment of the endosomal escape process—a critical challenge in siRNA delivery—chloroquine (CQ), a disruptor of endosomal vesicles, was added during the transfection period. Under the applied conditions, CQ will induce the accumulation of counter ions in the endosomes, resulting in endosomal swelling and rupture.[27] In the presence of CQ, a significant decrease in luciferase activity was observed at N/P 40, which accounts at N/P 160 for a silencing up to 80%. When the transfection efficiency for all dendritic carriers at a constant N/P was tested in the presence of this agent, silencing was observed in all cases, except for the hydrolytically stable hsB copolymer (FIG. 9C); being the highest transfection efficiencies mediated by the biodegradable series (bD and bB). This functional effect can be associated with the degradability of the GATGE repeating unit, having degradation points close to the siRNA binding sites.

Figure 8C:
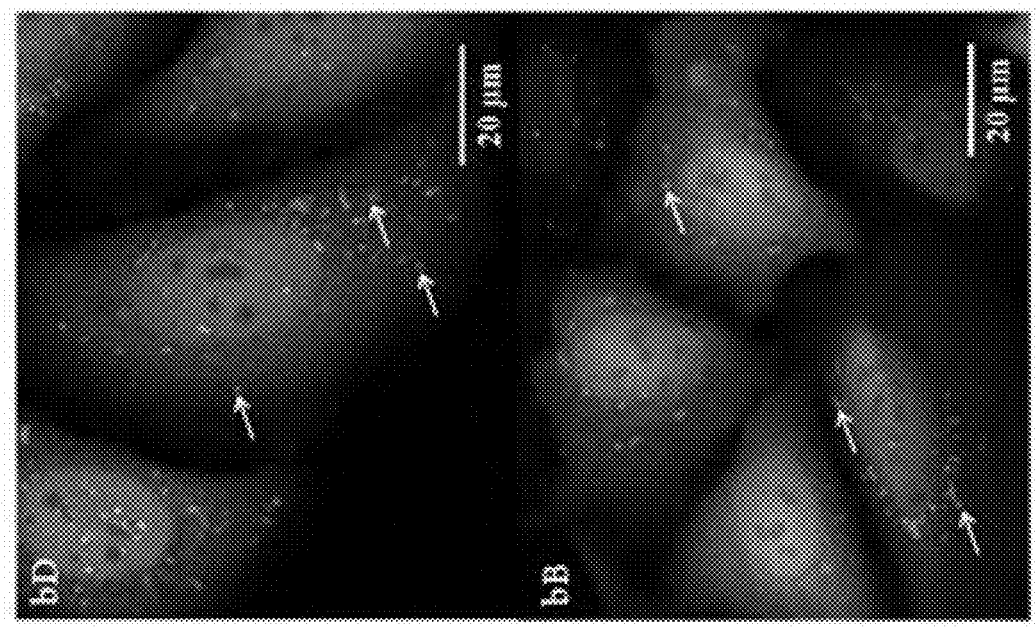

Consequently, degradability is revealed to be an important feature for siRNA release from these particles, contributing to the improvement of the transfection efficiency relative to the hydrolytically stable PEG-GATG counterparts. Interestingly, the higher ability of bB than bD to internalize siRNA (FIG. 8) does not translate in superior silencing efficiency. This effect is probably because its higher NA protection compromises the subsequent intracellular siRNA release regarding bD.

As the dendriplexes show good potential when aided by an endosomal disrupting molecule, the capacitation of the dendriplexes with these endosomolytic properties as we had previously explored.[28]

In an embodiment, dry $CH_2Cl_2$ was purchase from Prolabo. Dry DMF, $Et_3N$, gallic acid, tert-butanol, oxalic acid, $NaHCO_3$, $Na_2SO_4$, 4-bromobutanoic acid, N,N'-dicyclohexylcarbodiimide (DCC), dimethylaminopyridine (DMAP), $K_2CO_3$, 18-crown-6, Pd/C, hydroxybenzotriazole (HOBt), sodium ascorbate, and poly(ethylene glycol) methyl ether (PEG-OH; Mw 5000 g/mol) were purchased from Sigma. Monomethyl ether PEG(5000) amino (PEG-$NH_2$.HCl, Mn=5079 Da, Mw=5113, Mw/Mn=1.007) and monomethyl ether PEG(10000) amino (PEG-$NH_2$.HCl, Mn=10083 Da, Mw=10153, Mw/Mn=1.007) were purchased from Jenkem Technology USA. N1-(prop-2-yn-1-yl)propane-1,3-diamine.2 HCl and 4-ethynyl-benzenemethanamine.HCl were purchased from Amatek Chemical. All solvents were HPLC grade and used without further purification. Deuterated solvents were purchase from Cortecnet SAS.

In an embodiment, column chromatography was performed with 230-400 mesh silica gel. Thin-layer chromatography (TLC) was done on silica 60/F-254 aluminum-backed plates (E. Merck). Ultrafiltration was performed on Amicon stirred cells with Ultracel® 1 KDa membranes. Ultrafiltration membranes were purchase from Millipore. Nanopure water (18 MΩ·cm) was obtained from a Milli-Q water filtration system, Millipore Corp. Non-labeled siRNAmi/siRNA and siRNAmi/siRNA duplexes labeled at the 5' end of the sense strand were purchased from Integrated DNA Technologies. Nuclease free water was purchased from Qiagen. Luciferase assay system was purchased from Promega. DMEM and Opti-MEM were purchased from Gibco. Fetal bovine serum (FBS) was purchased from Gibco. Cell culture plates were purchased from BD Biosciences. Hoecsht 33342 was purchased from Life Technologies. U2OS/GFPLuc cells were kindly gifted by Prof. Edvard Smith (Karolinska Institute, Sweden). 2-[2-(2-azidoethoxy)ethoxy]ethanol (azidetriethylene glycol), 3,4,5-Tri-(2-(2-(2-azidoethoxy)ethoxy) ethyl)benzoic acid (GATG building unit 7), [4,10-Bis-carboxymethyl-7-[(2-propynyl-carbamoyl)-methyl]-1,4,7,10-tetraaza-cyclododec-1-yl]-acetate gadolinium (III) complex (Alkynyl-DO3A-Gd) and generations 1 and 2 of hydrolytically stable PEG-GATG dendritic block copolymers were prepared following protocols previously reported.[16,18,29] 4-ethynylbenzoic acid was prepared following a known procedure in the literature.[30] $K_2CO_3$ was dried under reduced pressure at 65° C. NMR spectra were recorded with a Bruker Avance III 400 MHz and a Bruker Avance III HD 600 MHz spectrometers in $D_2O$, $CD_2Cl_2$, or $CDCl_3$. Chemical shifts are reported in ppm (δ units) and were referenced to the residual solvent signals ($CD_2Cl_2$, $CDCl_3$) or the HOD signal ($D_2O$). SI-MS analysis was carried out with a LTQ Orbitrap XL mass spectrometer controlled by LTQ Tune Plus 2.5.5 and Xcalibur 2.1.0. The capillary voltage of the electrospray ionization (ESI) was set to 3000 V. The capillary temperature was 250° C. The sheath gas flow rate (nitrogen) was set to 5 (arbitrary unit as by the software). The capillary voltage was 16 V and the tube lens voltage 80 V. IR spectra were recorded with a FTIR-RAMAN Perkin Elmer 2000 spectrometer (KBr) and a FT-IR Perkin Elmer Spectrum Two spectrometer equipped with a diamond crystal (ATR). For KBr technique, each pellet was prepared by blending 2 mg of the PEG-dendritic block copolymer (vacuum dried 24 h at 45° C.) with 200 mg of KBr (dried 24 h at 105° C.). After a 5-min purge of the sample chamber with N2, IR spectra were immediately recorded by accumulation of 200 interferograms at a 4 $cm^{-1}$ spectral resolution over the range from 400 to 4000 $cm^{-1}$ with background subtraction. For ATR technique, PEG-dendritic block copolymers were used directly without further preparation. The IR spectra were recorded by accumulation of 20 interferograms at a 4 $cm^{-1}$ spectral resolution over the range from 400 to 4000 $cm^{-1}$ with background subtraction. MALDI-TOF MS were carried out on a Bruker Autoflex III with NdYAG laser, operating in positive linear mode. Samples were dissolved in MeOH at a concentration $2\times10^{-4}$ M and were mixed with the matrix (trans-2-[3-(4-tert-butylphenyl)-2-methyl-2-propenylidene]nalononitrile, DCTB, 10 mg/mL in $CH_2Cl_2$) in a proportion matrix:sample 4:1. NaI was employed as cationizing agent. Inductively coupled plasma optical emission spectrometry (ICP-OES) measurements were taken on a Perkin-Elmer Optima 4300-DV. All standards and samples were spiked with an internal standard of In at a final concentration of 2 mg/L. Thermogravimetric analysis (TGA) measurements were performed on a Setaram SETSYS Evolution TGA.

In an embodiment, the synthesis and characterization of tert-butyl gallate (2) was conducted was follows: EDC.HCl (1180 mg, 6.17 mmol) was slowly added, in small portions, to a suspension of gallic acid (1000 mg, 5.88 mmol) in dry tBuOH (35 mL). The reaction mixture was magnetically stirred at rt for 48 h under inert atmosphere (Ar). Then, $Et_2O$ (25-40 mL) and oxalic acid (970 mg, 0.29 mmol) were added. The resulting mixture was filtered and the filtrate was washed with 0.3 M $NaHCO_3$, dried ($Na_2SO_4$) and concentrated to give 2 (980 mg, 74%) as a pale yellow solid. $^1H$ NMR (300 MHz, $CDCl_3$) δ: 1.54 (s, 9H), 5.22 (br s, 3H), 7.20 (s, 2H). $^{13}C$ NMR (75 MHz, $CDCl_3$) δ: 31.0, 81.4, 109.7, 123.1, 136.6, 143.9, 166.6. ESI-MS Calcd for $C_{11}H_{13}O_5^-$: 225.08412. Found $[M-H]^-$: 225.07795.

In an embodiment, the synthesis and characterization of 2-[2-(2-azidoethoxy)ethoxy]ethyl 4-bromobutanoate (4) was conducted as follows: 2-[2-(2-azidoethoxy)ethoxy]ethanol (referred in the manuscript as "azidetriethylene glycol") (504 mg, 2.88 mmol), 4-bromobutanoic acid (720 mg, 4.31 mmol), DCC (890 mg, 4.31 mmol) and 4-dimethylaminopyridine (DMAP) (35 mg, 0.29 mmol) were dissolved in dry $CH_2Cl_2$ (5.7 mL). The suspension was magnetically stirred for 12 h at rt, after which $Et_3N$ (1.0 mL, 7.19 mmol) was added and stirred for 1 h. The suspension was evaporated and the resulting residue was resuspended in $Et_2O$ and filtered. The filtrate was evaporated and the resulting yellow oil was purified by column chromatography (hexane/ethyl acetate [2:1]) to yield 4 (906 mg, 97%) as a pale yellow oil. $^1H$ NMR (400 MHz, $CDCl_3$) δ: 2.08 (quint, J=6.8 Hz, 2H), 2.44 (t, J=7.1 Hz, 2H), 3.30 (t, J=4.6 Hz, 2H), 3.38 (t, J=6.5 Hz, 2H), 3.57-3.64 (m, 8H), 4.16 (t, J=4.7 Hz, 2H). $^{13}C$ NMR (100 MHz, $CDCl_3$) δ: 27.4, 32.1, 32.4, 50.3, 63.3, 68.8, 69.8, 70.3, 70.4, 172.1. ESI-MS Calcd for $C_{10}H_{18}BrN_3NaO_4^+$: 346.03784. Found $[M+Na]^+$: 346.03663.

In an embodiment, the synthesis and characterization of 3,4,5-tris(4-{2-[2-(2-azidoethoxy)ethoxy]ethoxy}-4-oxobutoxy)benzoic acid (5) (GATGE building unit) was conducted as follows: tert-butyl gallate 2 (97 mg, 0.43 mmol), dry $K_2CO_3$ (596 mg, 4.31 mmol), and 18-crown-6 (11.4 mg, 0.04 mmol) were sequentially added to a solution of 4 (559 mg, 1.72 mmol) in dry DMF (0.86 mL) under Ar. Then, the reaction mixture was heated at 80° C. for 12 h under magnetic stirring. After cooling down to rt, the solvent was evaporated and the resulting crude product was filtered to remove solid residues. The filtrate was concentrated and the resulting residue was purified by column chromatography (hexane/ethyl acetate [1:2]) to yield tris{2-[2-(2-azidoethoxy)ethoxy]ethyl} 4,4',4"-{[5-(tert-butoxycarbonyl)benzene-1,2,3-triyl]tris(oxy)}tributanoate (336 mg, 82%) as a pale yellow oil. $^1H$ NMR (400 MHz, $CDCl_3$) δ: 1.57 (s, 9H), 1.98-2.16 (dm, 6H), 2.58 (dt, J=28.6 Hz, J=7.4 Hz, 6H), 3.37 (t, J=5.0 Hz, 6H), 3.63-3.71 (m, 24H), 4.03 (dt, J=8.5 Hz, J=6.1 Hz, 6H), 4.29-4.33 (m, 6H), 7.18 (s, 2H). $^{13}C$ NMR (100 MHz, $CDCl_3$) δ: 24.6, 25.5, 28.1, 30.5, 30.6, 50.6, 63.4, 63.5, 67.9, 69.1, 69.2, 70.0, 70.6, 72.2, 81.1, 108.0, 127.0, 141.4, 152.3, 165.3, 173.0, 173.3. EI-MS: Calcd for $C_{41}H_{65}N_9NaO_{12}^+$: 978.43961; Found $[M+Na]^+$: 978.43760.

In an embodiment, Tris{2-[2-(2-azidoethoxy)ethoxy]ethyl} 4,4',4"-{[5-(tert-butoxycarbonyl)benzene-1,2,3-triyl]tris(oxy)}tributanoate (336 mg, 0.35 mmol) was dissolved in a mixture of dried $CH_2Cl_2$/trifluoroacetic acid (1:1) (3.5 mL)

and was stirred under Ar for 1.5 h and then concentrated to dryness to afford 3,4,5-tris(4-{2-[2-(2-azidoethoxy)ethoxy]ethoxy}-4-oxobutoxy)benzoic acid 5 as a pale yellow oil (316 mg, 100%). $^1$H NMR (400 MHz, CDCl$_3$) δ: 2.09 (dm, 6H), 2.60 (dt, J=29.0 Hz, J=7.3 Hz, 6H), 3.38 (t, J=5.0 Hz, 6H), 3.65-3.72 (m, 24H), 4.07 (t, J=6.1 Hz, 6H), 4.23-4.27 (m, 6H), 7.31 (s, 2H). $^{13}$C NMR (100 MHz, CDCl$_3$) δ: 24.4, 25.4, 30.4, 30.5, 50.5, 63.3, 63.5, 67.8, 69.0, 69.0, 69.9, 70.4, 70.5, 72.2, 108.4, 108.5, 124.2, 142.0, 142.3, 152.3, 170.3, 172.8, 173.2. EI-MS: Calcd for $C_{37}H_{37}N_3NaO_{17}^+$: 922.37646; Found [M+Na]$^+$: 922.37809.

In an embodiment, the synthesis and characterization of PEG-b[G2]-N$_3$ (9) was made as follows: Pd/C (33 mg, 10% w/w) was added to a solution of PEG-[G1]-N$_3$ (167 mg, 0.03 mmol) in MeOH (10 mL). The resulting mixture was vigorously stirred under H$_2$ (1 atm) for 5 h. Then, the catalyst was removed by filtration and the filtrate was concentrated and dried. HOBt (18 mg, 0.13 mmol) and EDC.HCl (26 mg, 0.13 mmol) were added to a solution of the above residue and 5 (121 mg, 0.13 mmol) in dry CH$_2$Cl$_2$ (1 mL). The resulting solution was stirred for 48 h at room temperature under inert atmosphere (Ar), and then it was concentrated and precipitated from CH$_2$Cl$_2$/iPrOH to give PEG-b[G2]-N3 as a white powder (208 mg, 86%). FTIR (KBr): 3434, 2889, 2110, 1736, 1112 cm$^{-1}$. $^1$H NMR (400 MHz, CD$_2$Cl$_2$) δ: 1.94-2.10 (m, 18H), 2.48-2.60 (m, 18H), 3.31-3.35 (m, 21H), 3.39-3.78 (m, ~554H), 3.96-4.03 (m, 18H), 4.11-4.20 (m, 24H), 7.04-7.07 (m, 8H). $^{13}$C NMR (100 MHz, CD$_2$Cl$_2$) δ: 24.1, 25.1, 29.9, 30.1, 39.5, 50.3, 50.3, 58.1, 62.9, 63.1, 67.5, 68.6, 68.7, 69.3, 69.4, 69.5, 70.0, 71.4, 71.7, 105.3, 105.3, 129.4, 139.8, 151.9, 152.1, 166.3, 172.4, 172.7. MALDI-TOF MS (DCTB+NaI, linear mode, m/z): Mp 8092.0 ([M+Na]$^+$), Mn 8045.5, Mw 8062.3. Calcd: Mp 8222.4 ([M+Na]$^+$), Mn 8269.0.

In an embodiment, the synthesis and characterization of PEG-fb[G1]-N$_3$ (10) was made as follows: EDC.HCl (8 mg, 0.04 mmol) and catalytic DMAP (0.3 mg, 2 ma) were added to a solution of PEG-OH (100 mg, 0.02 mmol) and GATGE unit 5 (35 mg, 0.04 mmol) in CH$_2$Cl$_2$ (1.2 mL). The resulting solution was stirred at room temperature for 12 h under Ar, and then it was concentrated and precipitated from CH$_2$Cl$_2$/iPrOH to give pure PEG-fb[G1]-N3 as a white powder (108 mg, 91%). $^1$H NMR (400 MHz, CD$_2$Cl$_2$, Me$_4$Si) δ: 1.96-2.14 (dm, 6H), 2.56 (dt, J=23.2, J=7.4, 6H), 3.32 (s, 3H), 3.34 (t, J=5.0, 6H), 3.39-3.79 (m, ~552H), 4.04 (m, 6H), 4.19 (m, 6H), 4.40 (dd, J=5.1, J=4.8, 2H), 7.25 (s, 2H).

In an embodiment, the synthesis and characterization of PEG-fb[G2]-N$_3$ (11) was made as follows: Pd/C (22 mg, 10% w/w) and 1 M HCl in MeOH (109 µL, 0.11 mmol) were added to a solution of PEG-fb[G1]-N$_3$ (108 mg, 0.02 ma) in MeOH (4 mL). The resulting mixture was vigorously stirred under H$_2$ (1 atm) for 3 h. Then, the catalyst was removed by filtration and the filtrate was concentrated and dried. HOBt (15 mg, 0.11 mmol), EDC.HCl (21 mg, 0.11 mmol) and Et$_3$N (15 µL, 0.11 mmol) were added to a solution of the above residue and 5 (98 mg, 0.11 mmol) in dry CH$_2$Cl$_2$ (546 µL). The resulting solution was stirred for 48 h at RT under inert atmosphere (Ar), and then it was concentrated and precipitated from CH$_2$Cl$_2$/iPrOH to give PEG-fb[G2]-N3 as a white powder (169 mg, 81%). $^1$H NMR (400 MHz, CD$_2$Cl$_2$) δ: 1.95-2.13 (dm, 24H), 2.56 (dt, J=25.6, J=7.3, 24H), 3.32 (s, 3H), 3.34 (m, 18H), 3.39-3.78 (m, ~552H), 4.02 (m, 24H), 4.19 (m, 24H), 4.38-4.41 (m, 2H), 6.69-6.79 (m, 3H), 7.01 (s, 4H), 7.25 (s, 4H).

In an embodiment, the synthesis and characterization of PEG-fb[G3]-N$_3$ (12) was made as follows: Pd/C (13 mg, 10% w/w) and 1 M HCl in MeOH (203 µL, 0.20 mmol) were added to a solution of PEG-fb[G2]-N$_3$ (64 mg, 8 ma) in MeOH (3 mL). The resulting mixture was vigorously stirred under H$_2$ (1 atm) for 7 h. Then, the catalyst was removed by filtration and the filtrate was concentrated and dried. HOBt (18 mg, 0.13 mmol), EDC.HCl (26 mg, 0.13 mmol) and Et$_3$N (19 µL, 0.13 mmol) were added to a solution of the above residue and 5 (121 mg, 0.13 mmol) in dry CH$_2$Cl$_2$ (1.5 mL). The resulting solution was stirred for 48 h at RT under inert atmosphere (Ar), and then it was concentrated and precipitated from CH$_2$Cl$_2$/iPrOH to give PEG-fb[G3]-N$_3$ as a white powder (91 mg, 75%). $^1$H NMR (400 MHz, CD$_2$Cl$_2$) δ: 1.95-2.12 (dm, 78H), 2.50-2.60 (dm, 78H), 3.32 (s, 3H), 3.32-3.35 (m, 54H), 3.39-3.78 (m, ~552H), 3.95-4.05 (m, 78H), 4.17-4.21 (m, 78H), 4.38-4.40 (m, 2H), 6.58 (br s, 8H), 6.82 (br s, 4H), 7.02 (s, 16H), 7.24 (s, 10H).

In an embodiment, the general procedure for the multivalent functionalization of PEG-GATGE-N$_3$, PEG-fb-GATGE-N$_3$ and PEG-GATG-N$_3$ with alkynated amine ligands by CuAAC is as follows: PEG-GATG dendritic block copolymers (PEG-b[G2]-N$_3$, PEG-fb[G3]-N$_3$ and PEG-[G2]-N$_3$) were dissolved in DMF/H$_2$O (1:1) to give a 0.1 M final concentration of terminal azides. Then, alkynated ammonium salts 10 and 11 (200 mol % per azide) and aqueous 0.1 M CuSO$_4$.5H$_2$O (5 mol % per azide) and 0.1 M sodium ascorbate (25 mol % per azide) were added. The resulting solution was stirred at room temperature for 24 h, and the product was isolated by ultrafiltration (Ultracel® 1,000 MWCO) of the concentrated reaction mixture washing with 0.1 M EDTA (pH 6), 0.6 M NaCl and H$_2$O.

In an embodiment, the synthesis and characterization of bD (15) is as follows: from PEG-b[G2]-N$_3$ (92 mg, 11.4 µmol), 10 (38 mg, 0.21 mmol), 0.1 M sodium ascorbate (257 µL), and 0.1 M CuSO$_4$.5H$_2$O (51 µL) in DMF (514 µL)/H$_2$O (206 µL), and following the above general procedure, bD (111 mg, 100%) was obtained as a white foaming solid. $^1$H NMR (400 MHz, D$_2$O) δ: 1.98-2.07 (m, 18H), 2.14 (quint, J=7.8 Hz, 18H), 2.56-2.65 (m, 18H), 3.14 (t, J=7.8 Hz, ~18H), 3.21 (t, J=7.3 Hz, 18H), 3.42 (s, 3H), 3.57-3.86 (m, ~536H), 3.95-4.09 (m, 42H), 4.23-4.25 (m, ~18H), 4.40-4.41 (m, ~18H), 4.64-4.67 (m, ~18H), 7.08-7.11 (m, ~8H), 8.21 (s, 6H), 8.22 (s, 3H). $^{13}$C NMR (100 MHz, D$_2$O) δ: 24.8, 25.0, 25.8, 31.3, 31.4, 37.6, 40.5, 40.7, 42.5, 45.0, 51.0, 59.0, 64.7, 64.8, 68.8, 69.3, 69.6, 69.8, 69.8, 70.0, 70.3, 70.5, 71.9, 73.5, 106.3, 127.3, 130.1, 130.2, 139.3, 140.1, 140.2, 140.5, 152.7, 152.9, 169.6, 176.2, 176.3. An intramolecular degradation up to 5% was determined for 12 by integration of the appropriate signals (k, l, n, o, p and q) in the $^1$H NMR spectrum (FIG. 3B).

In an embodiment, the synthesis and characterization of bB (16) is as follows: from PEG-b[G2]-N$_3$ (45 mg, 5.57 µmol), 11 (17 mg, 0.10 mmol), 0.1 M sodium ascorbate (124 µL), and 0.1 M CuSO$_4$.5H$_2$O (25 IA) in DMF (249 µL)/H$_2$O (100 µL), and following the above general procedure, bB (53 mg, 100%) was obtained as a white foaming solid. $^1$H NMR (400 MHz, D$_2$O) δ: 1.73-1.88 (m, 18H), 2.33-2.39 (m, 18H), 3.42 (s, 3H), 3.55-3.95 (m, ~578H), 4.08-4.14 (m, 36H), 4.52-4.55 (m, 18H), 6.88-6.92 (m, 8H), 7.34-7.43 (m, 18H), 7.66-7.85 (m, 18H), 8.21-8.23 (m, 9H). $^{13}$C NMR (100 MHz, D$_2$O) δ: 24.4, 25.2, 30.7, 40.0, 40.2, 43.2, 50.5, 58.5, 64.3, 64.3, 67.7, 68.1, 68.6, 68.8, 69.1, 69.4, 69.5, 70.0, 70.4, 71.4, 72.2, 72.5, 72.7, 105.9, 122.9, 126.3, 129.9, 130.6, 133.4, 139.7, 146.9, 152.3, 152.3, 168.7, 175.4, 175.5.

Figure 22:
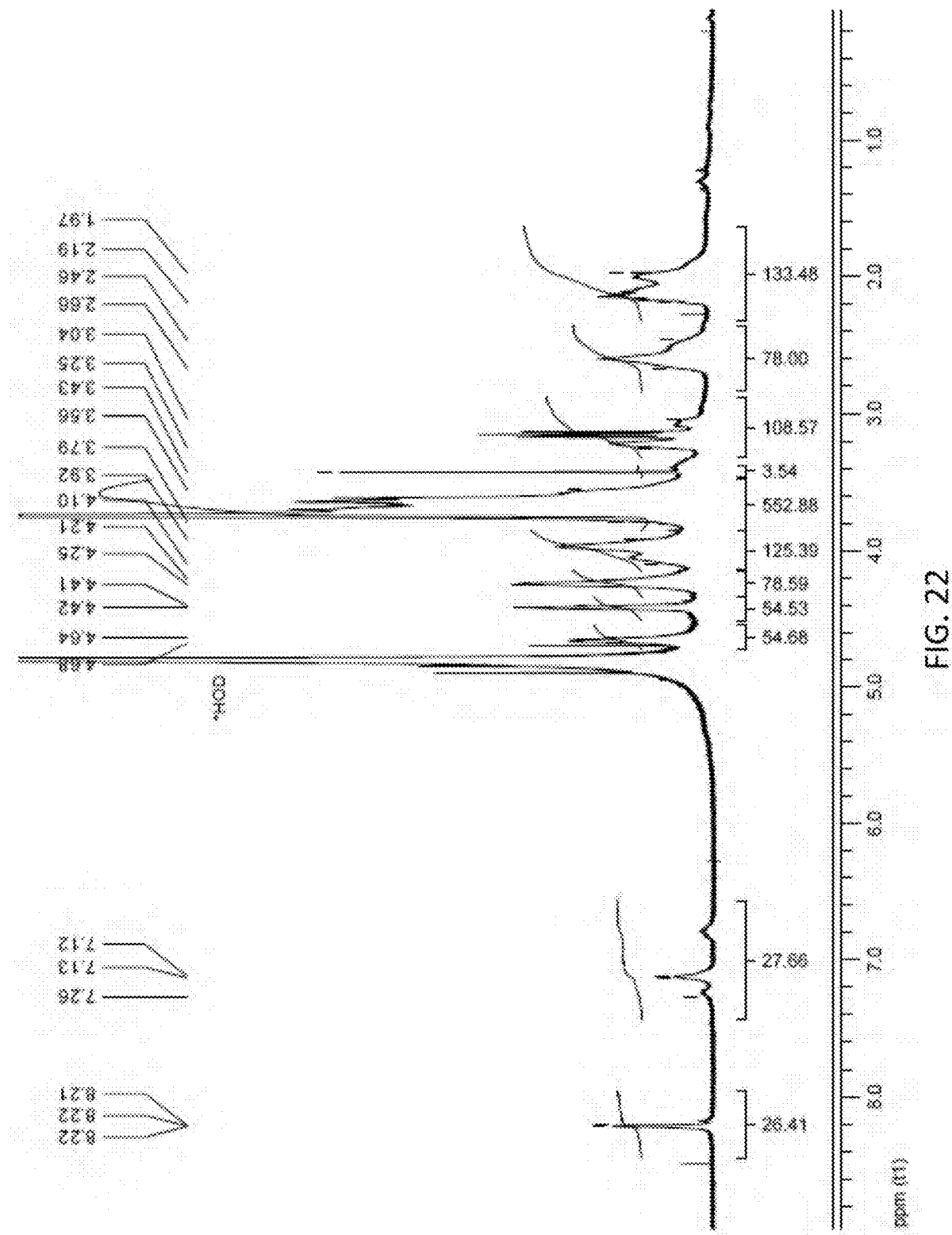
FIG. 22—$^1$H spectrum of fbD (17).

In an embodiment, the synthesis and characterization of fbD (17) is as follows: from PEG-fb[G3]-N3 (23 mg, 1.4 µmol), 10 (14 mg, 0.08 mmol), 0.1 M sodium ascorbate (97 µL), and 0.1 M CuSO$_4$.5H$_2$O (19 IA) in DMF (194 µL)/H$_2$O (78 µL), and following the above general procedure, PEG-fb[G3]-D (29 mg, 97%) was obtained as a white foaming solid. $^1$H NMR (400 MHz, D$_2$O) δ: 1.97-2.19 (m, 132H), 2.46-2.66 (m, 78H), 3.04-3.25 (~108H), 3.43 (s, 3H), 3.56-3.79 (m, ~552H), 3.92-4.10 (m, ~132H), 4.21-4.25 (m, ~78H), 4.40-4.43 (m, ~54H), 4.64-4.68 (m, ~54H), 7.12-7.26 (m, 26H), 8.21-8.22 (m, 27H). An intramolecular degradation up to 5% was determined for 17 by integration of the appropriate signals in the $^1$H NMR spectrum (FIG. 22).

Figure 23:
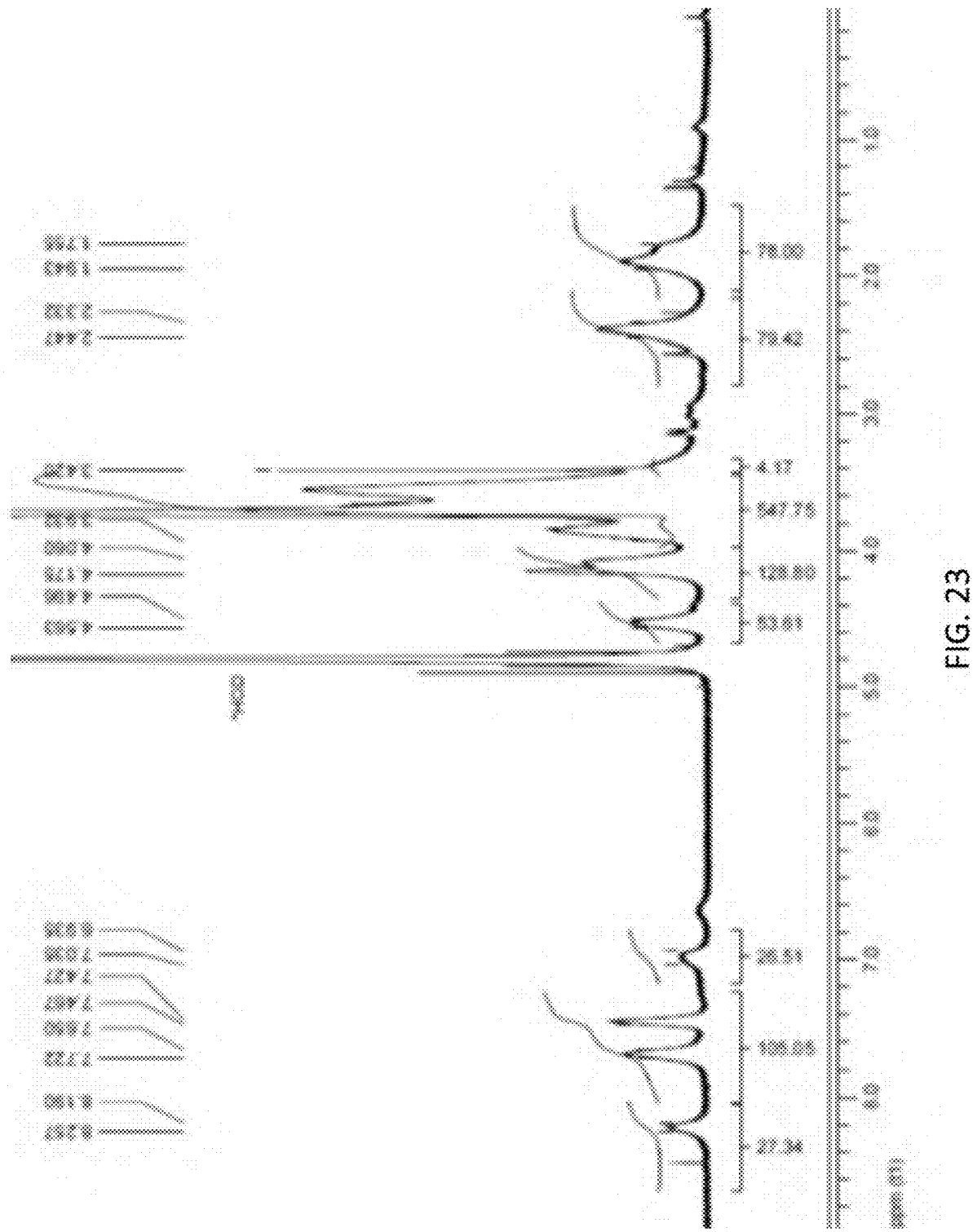
FIG. 23. $^1$H spectrum of fbB (18).
Figure 24:
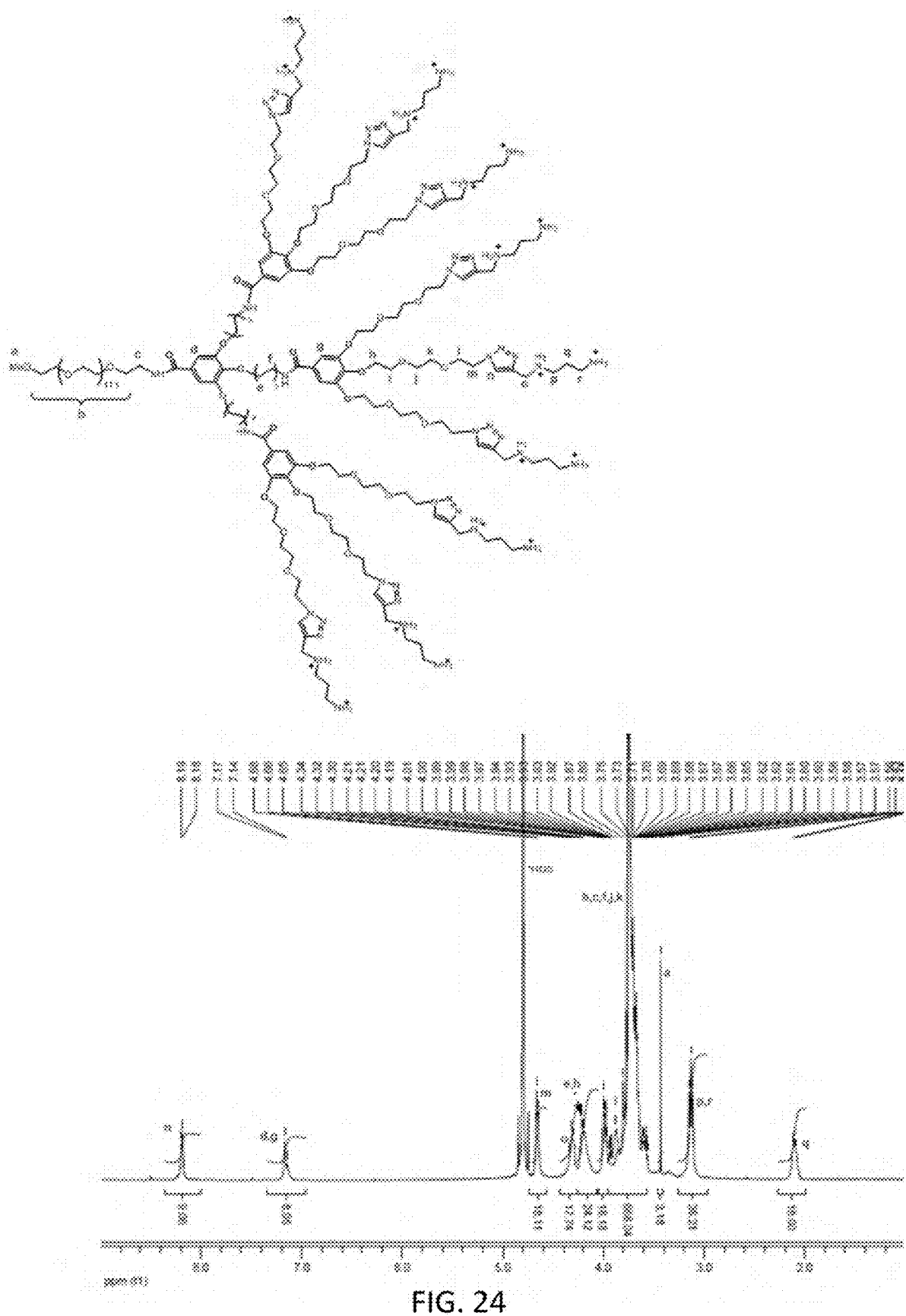
FIG. 24—¹H NMR spectrum and assignment of the signals for hsD (19).
Figure 25:
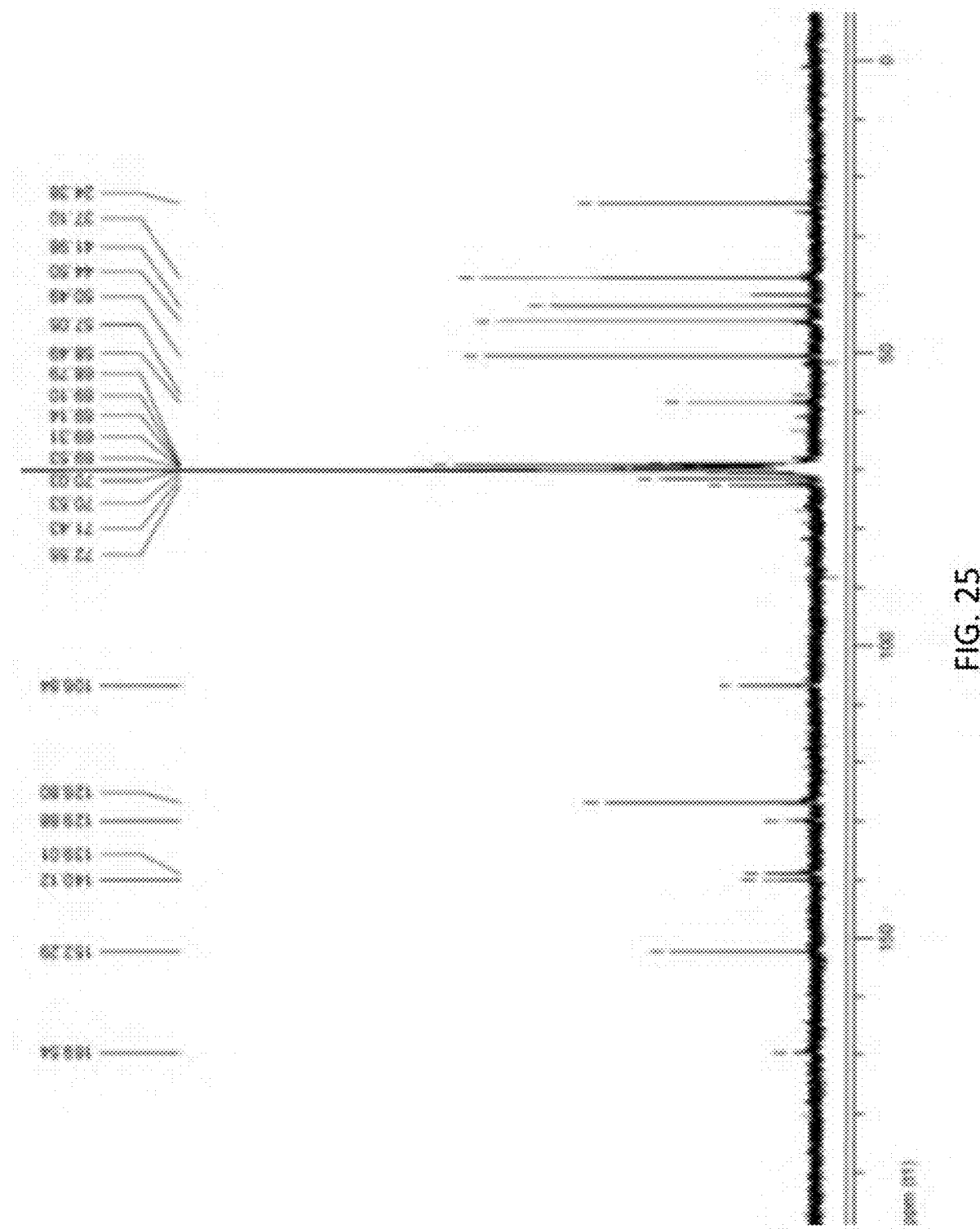
FIG. 25—¹³C NMR spectrum of hsD (19).
Figure 26:
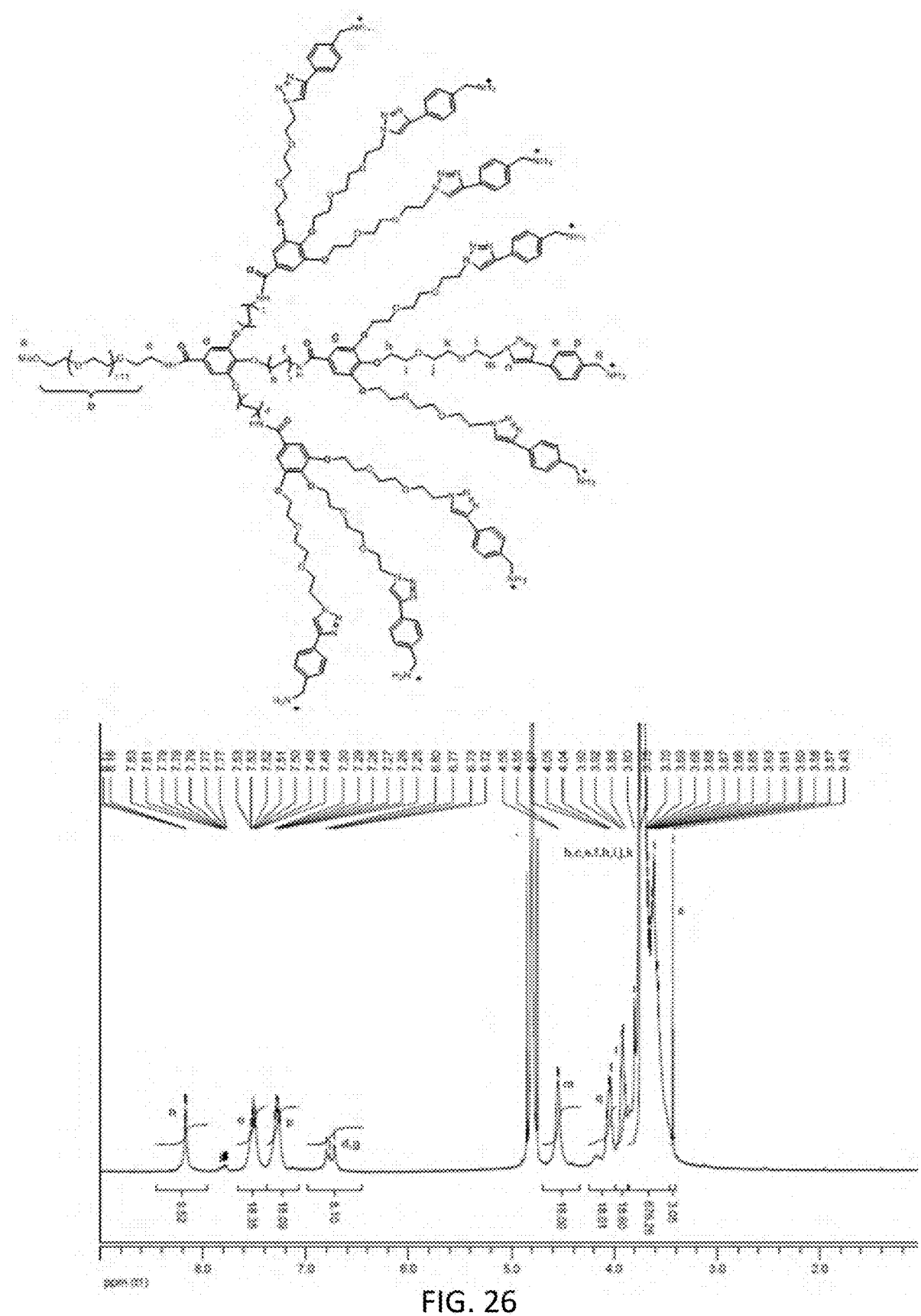
FIG. 26—¹H NMR spectrum and assignment of the signals for hsB (20).
Figure 27:
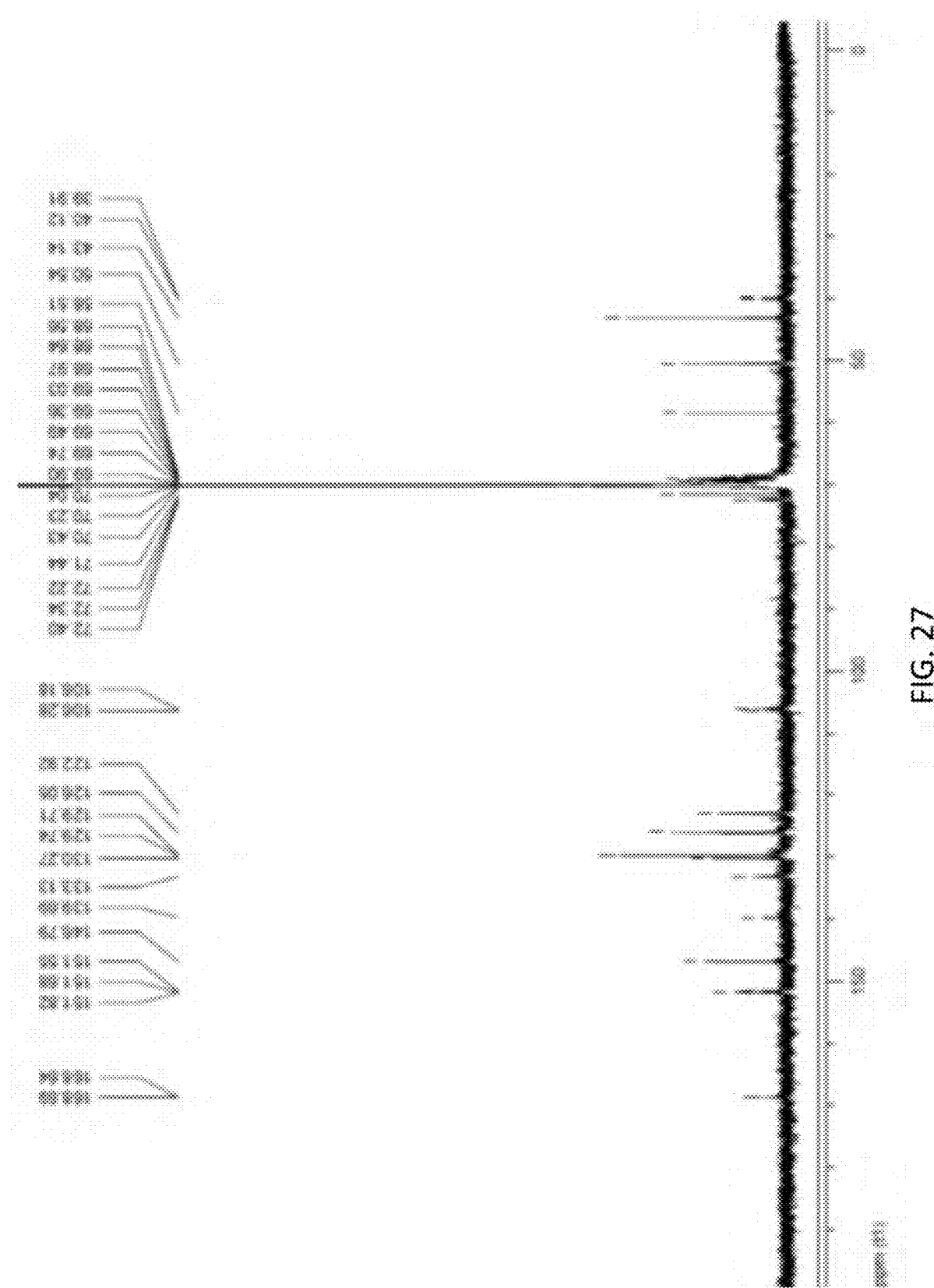
FIG. 27—¹³C NMR Spectra of hsB (20).

In an embodiment, the synthesis and characterization of fbB (18) is as follows: from PEG-fb[G3]-N3 (25 mg, 1.5 μmol), 11 (14 mg, 0.08 mmol), 0.1 M sodium ascorbate (102 μL), and 0.1 M CuSO$_4$.5H$_2$O (20 μL) in DMF (204 μL)/H$_2$O (82 μL), and following the above general procedure, bB (31 mg, 98%) was obtained as a white foaming solid. $^1$H NMR (400 MHz, D$_2$O) δ: 1.75-1.94 (m, 78H), 2.33-2.45 (m, 78H), 3.42 (s, ~3H), 3.42-3.93 (m, ~684H), 4.06-4.17 (m, ~132H), 4.50-4.56 (m, ~54H), 6.93-7.06 (m, 26H), 7.43-7.47 (m, ~54H), 7.65-7.72 (m, ~54H), 8.19-8.26 (m, 27H). An intramolecular degradation up to 2% was determined for 18 by integration of the appropriate signals in the $^1$H NMR spectrum (FIG. 23).

In an embodiment, the synthesis and characterization of hsD (19) is as follows: from PEG-[G2]-N$_3$ (45 mg, 6.09 μmol), 10 (20 mg, 0.11 mmol), 0.1 M sodium ascorbate (132 μL), and 0.1 M CuSO$_4$.5H$_2$O (27 IA) in DMF (264 μL)/H$_2$O (105 μL), and following the above general procedure, hsD (52 mg, 94%) was obtained as a white foaming solid. $^1$H NMR (400 MHz, D$_2$O) δ: 2.06-2.14 (m, 18H), 3.13 (t, J=7.7 Hz, 36H), 3.44 (s, 3H), 3.56-3.94 (m, ~536H), 3.97-4.01 (m, 18H), 4.16-4.3 (m, 24H), 4.28-4.33 (m, 18H), 4.66 (t, J=4.8 Hz, 18H), 7.14-7.17 (m, 8H), 8.16-8.23 (m, 9H). $^{13}$C NMR (100 MHz, D$_2$O) δ: 24.4, 37.1, 40.1, 42.0, 44.5, 50.5, 58.5, 68.8, 69.1, 69.1, 69.3, 69.5, 70.0, 71.4, 72.5, 106.8, 126.8, 129.9, 139.0, 140.1, 152.3, 169.5.

In an embodiment, the synthesis and characterization of hsB (20) is as follows: from PEG-[G2]-N$_3$ (G2) (52.5 mg, 7.11 μmol), 11 (21 mg, 0.13 mmol), 0.1 M sodium ascorbate (160 μL), and 0.1 M CuSO$_4$.5H$_2$O (32 μL) in DMF (320 μL)/H$_2$O (128 μL), and following the above general procedure, PEG-[G2]-8 (62 mg, 98%) was obtained as a white foaming solid. $^1$H NMR (400 MHz, D$_2$O) δ: 3.43 (s, 3H), 3.57-3.80 (m, ~560H), 3.88-3.94 (m, 18H), 4.02-4.07 (m, 18H), 4.52-4.57 (m, 18H), 6.72-6.80 (m, 8H), 7.22-7.33 (m, 18H), 7.46-7.83 (m, 18H), 8.16-8.17 (m, 9H). $^{13}$C NMR (100 MHz, D$_2$O) δ: 39.9, 40.1, 43.1, 50.5, 58.5, 68.5, 68.6, 69.0, 69.0, 69.4, 69.5, 69.7, 69.9, 70.0, 70.2, 70.4, 71.4, 72.2, 72.3, 72.4, 106.3, 106.2, 122.9, 126.0, 129.4, 129.7, 130.3, 133.1, 139.7, 146.8, 151.5, 151.7, 151.8, 168.6, 168.7.

In an embodiment, Degradability studies were conducted. Degradation of ammonium salt 6 and the dendritic copolymers bD (15) and bB (16) were studied simulating physiological pH conditions at 37° C. Samples (1 mg/mL) were incubated at 37° C. in phosphate buffered saline (PBS 3×, pD 7.4) and/or in acetate buffer saline (30 mM NaOAc+420 mM NaCl, pD 5.0). Buffers were prepared in deuterium oxide. Moreover, for the case of ammonium salt 6, buffers were supplemented with acetone-d6 (D$_2$O/acetone-d6, 85:15) with the aim of improving solubility and resolution of NMR spectra for integration purposes. Samples were analyzed by $^1$H-NMR at different time points.

In an embodiment, dendriplex preparation was made. Dendritic copolymer/siRNA complexes were prepared at N/P ratios (where N=number of primary amines in the conjugate; P=number of phosphate groups in the RNA backbone) ranging from 20 to 160 by adding siRNA (20 μM) to different volumes of dendritic copolymer solution (6 mg/mL) in Nuclease-Free (NF) water. Then dendriplex solutions were vortexed for 10 sec and allowed to incubate for 30 min at room temperature prior to experiments. For the experiments where biological activity is not assessed, a double stranded DNA of exact same sequence as anti-enhanced green fluorescence protein siRNA (anti-eGFP siRNA) was used for mimicking siRNA (siRNAmi) for its ease of synthesis and possibility to obtain in higher yields and purity. siRNA sequence: sense Seq. I.D. 1: 5'-GCUGACCCUGAAGUUCAUCUGCACC-3'.

In an embodiment, polyacrylamide gel electrophoresis shift assay. Polyacrylamide gels (with 4% stacking and 15% resolving gel) were prepared in Tris/Borate/EDTA buffer. Dendriplex solutions were prepared at different N/P ratios as previously described with the difference that siRNAmi (where the RNA nucleotides were substituted by DNA) was used instead of siRNA. The amount of dendriplex corresponding to 12 pmol of siRNAmi was mixed with 6 μL of loading buffer and subjected to gel electrophoresis at 100 V. Dendriplex/siRNAmi binding was shown by a lack of migration of the siRNAmi in the electrophoretic field (retention in the wells).

In an embodiment, SybrGold intercalation assays were conducted. Dendriplex/siRNAmi nanoparticles were prepared as previously described and then incubated in NF water (Qiagen) for 10 min at rt in a 96-well black plate with 2 μL of a 1:100 SYBRGold (Invitrogen) solution (in TAE buffer) (final volume of 200 μL). After incubation, fluorescence was measured ($\lambda_{exc}$=485 nm, $\lambda_{em}$=540 nm) using a micro-plate reader (SynergyMx). Results are given as percentage of complexation, where 100% represents complete siRNA complexation. The presented data are expressed as mean±SD of three independent sample measurements.

In an embodiment, the size, polydispersity index (PDI) and zeta potential (ZP) of dendriplexes were measured at 633 nm on a dynamic light scattering (DLS) instrument (Zetasizer Nano ZS, Malvern Instruments, UK) following the manufacturer instructions. Size and PDI were determined at RT with a detection angle of 173°. Zeta potential measurements were performed with a detection angle of 173 g. For size and PDI measurements dendriplexes were prepared in a final volume of 80 μL at different N/P ratios and analyzed either undiluted or, in the case of stability studies, further diluted 2-fold in 1×PBS with 20% (v/v) fetal bovine serum (FBS), in 1×PBS pH 7.4, and/or in 10 mM NaOAc+ 137 mM NaCl pH 5.0. For ZP measurements, dendriplexes were prepared in a final volume of 250 μL and diluted to 750 μL in Milli Q water prior to the measurements. The Smoluchowski model was applied for zeta potential determination, and cumulant analysis was used for mean particle size determination. The presented data are expressed as the mean±SD of three independent sample measurements.

For analysis of heparin-induced dissociation of dendriplexes, these were prepared at N/P 160 after which an aliquot was diluted in 1×PBS containing different heparin concentrations (previously diluted in 1×PBS also). Dendriplexes and heparin were then incubated for 2 h at 37° C. After incubation, dendriplexes (corresponding to 6 pmol siRNA) were loaded in 4-15% (w/v) polyacrylamide-TBE gels and stained subsequently with SYBRGold®.

In an embodiment, transmission electron microscopy was performed. Dendriplexes were prepared as previously described at N/P ratios of 80 and 160. Samples were mounted on a 200-mesh Ni grid with Formvar and carbon supporting film (not glow discharged) and stained with 2% (w/v) uranyl acetate (UA) solution. Excess stain was removed with filter paper, and the grid was dried prior to imaging. Samples were imaged using a Jeol JEM 1400 operated at 80 kV. Images were processed using ImageJ software (NIH, USA).

Dendriplexes degradation studies. Biodegradable dendriplexes were prepared as previously described at N/P ratio of 160 and further diluted 2-fold in acetate buffer solution (60 mM NaOAc, pH 5.0) and in Sorensen's phosphate buffer solution (60 mM $NaH_2PO_4$, pH 7.4) for 1, 24 and 48 h. After that, dendriplexes were incubated with heparin (at a final heparin concentration of 0.010 mg/mL and 0.025 mg/mL for bD and bB dendriplexes, respectively) for 2 h at 37° C. After incubation, dendriplexes (corresponding to 3 pmol siRNA) were loaded in 4-15% polyacrylamide-TBE gels and stained subsequently with SYBRGold®.

In an embodiment, nuclease protection assays were carried out. Dendriplexes with a N/P ratio of 160 were prepared as previously described and incubated with 0.1 U DNase I per 0.2 μg of siRNAmi (annealed sense and antisense DNA strands mimicking siRNA) for 5, 15, 30 and 60 min at rt. For DNase inactivation samples were treated with EDTA (0.05 M final concentration), heated up to 65° C. for 10 min and further stabilized for 30 min at room temperature. Mixtures were treated with SDS to a final concentration of 0.1% and incubated for another 30 min. Finally, 1 pmol of siRNAmi was diluted in nuclease free (NF) water (final volume 10 μL), mixed with (LB) and further loaded into a polyacrylamide gel (10%). Naked siRNAmi and untreated dendriplexes were used as controls. Free wells were loaded with equivalent concentrations of salts, SDS and EDTA to allow a uniform band migration. The optimal DNase I concentration was previously determined by gel electrophoresis using naked siRNAmi.

In an embodiment, the osteosarcoma cell line U2OS were cultured in DMEM media supplemented with 10% (v/v) FBS and 40 μg/mL gentamicin (Gibco) at 37° C., 5% $CO_2$, in a cell incubator.

In an embodiment, cytotoxicity studies were carried out. Cell viability was evaluated as a function of the dendritic copolymer/dendriplex type and concentration. Cells were seeded in 96-well plates at a density of $3.75 \times 10^4$ cells/cm$^2$. At the time of transfection, the medium was replaced with non-supplemented DMEM. After 24 h post-transfection, the medium was replaced with fresh media containing 10% (v/v) FBS and 10% rezasurin and incubated for another 3 h. Fluorescence ($\lambda_{ex}$=530 nm, $\lambda_{em}$=590 nm) was measured in a micro-plate reader (SynergyMx, Biotek). The viability of cells exposed to dendritic copolymer was expressed as a percentage of the viability of non-treated cells.

In an embodiment, cellular membrane association using flow-cytometry was performed. Cells were seeded in 24-well plates at a density of $2.6 \times 10^4$ cells/cm$^2$ and incubated for 24 h in supplemented DM EM medium at 37° C., 5% $CO_2$, and grown to reach 70-80% confluence prior to transfection. At the time of transfection, the medium was replaced with non-supplemented DMEM. Dendriplexes were prepared with Cy-5 labeled siRNA as previously described. Cells were then transfected using 50 μL dendriplexes in a final volume of 300 μL, in particular siRNA concentration of 0.1 pmol/μL. After 24 h incubation, cells were rinsed twice with 1×PBS, trypsinized, centrifuged, resuspended in 1×PBS 2% FBS and analyzed by FACS (FACSCalibur, BD Biosciences). Non-treated cells and cells transfected with Lipofecta mine 2000 (Life Technologies) were used as negative and positive controls, respectively. Data was analyzed using Flowio software (version 8.3.7).

In an embodiment, cellular uptake using imaging flow cytometry was performed. U2OS cells were seeded in 24-well plates at a density of $2.6 \times 10^4$ cells/cm$^2$, incubated for 24 h in supplemented DMEM medium at 37° C., 5% $CO_2$, and grown to a confluence of 70-80% prior to transfection. At the time of transfection, the medium was replaced by non-supplemented DMEM. siRNAmi dendriplexes at N/P 160 were prepared using Cy-5 labeled siRNAmi. Cells were then transfected with a final volume of 350 μL (final siRNAmi concentration 0.1 pmol/μL). 24 h after incubation, cells were rinsed once with PBS 1× and trypsinized. Cells were then transferred to Eppendorfs and centrifuged for 5 min at 1200 rpm at 4° C. After washing with PBS 1×, cells were centrifuged (5 min at 1200 rpm at 4° C.), and subsequently fixed with 4% paraformaldehyde (PFA) for 15 minutes. After fixation, cells were washed twice with PBS 1×.

In an embodiment, cell images were acquired using an imaging flow cytometer (ImageStream®, Amnis, EDM Millipore, Darmstadt, Germany) at a magnification of 40×. A 488 nm wavelength laser was used to excite Cy-5 labeled siRNAmi. The fluorescence images were collected using the 660-745 nm spectral detection channel. Images were also acquired using the Extended Depth of Field (EDF) filter. Data was subsequently analyzed using IDEAS v6.1 image-analysis software (Amnis Corporation, EDM Millipore).

In an embodiment, each cell was divided into 2 regions—external (membrane) and internal (cytoplasm). A first mask was applied that covered the entire cell. The external region was determined by dilating the mask by the membrane thickness. The internal region was defined by the mask of the whole cell minus the cell membrane mask. A mask was then attributed to the intensity of the Cy5 channel. The intensity mask was merged with the cytoplasm (internal) mask, which allowed filtering cells for positive internalization. To determine the number of vesicle-loaded dendriplexes, masks were created which identify the fluorescent spots. The number of individual vesicles in a cell was enumerated using the Spot Count feature from the IDEAS v6.1 software, and plotted in frequency histograms (FIG. 23). Three regions (low, medium and high spot count) were defined based on the worst performing copolymer (hsD). The region for medium spot count was defined as mean spot count for hsD (3.5)±its corresponding standard deviation (2). The low spot count region is below 3.5−2 and the high spot region is above 3.5+2.

In an embodiment, confocal microscopy was performed as follows: cells were seeded μ-Slide 8-well ibiTreat (Ibidi) at a cell density of $2 \times 10^4$ cells/cm$^2$ and incubated for 24 h in supplemented DMEM medium at 37° C., 5% $CO_2$, and grown to reach 50-60% confluence prior to transfection. At the time of transfection, the medium was replaced with non-supplemented DMEM. PEG-bGATG-Ar/siRNAmi and PEG-bGATG-D/siRNAmi dendriplexes with N/P ratios of 160 were prepared using Cy5 labeled siRNAmi. Cells were then transfected using 50 μL dendriplexes in a final volume of 300 μL (siRNA at 0.1 pmol/μL). After 24 h, transfected cells were washed three times with PBS and incubated 10 min. (RT) with a 1:20000 diluted solution of Hoechst 33342 (10 mg/mL, Life technologies) for nuclear staining. Cells were then washed with PBS and Opti-MEM (no phenol-Red) was added to cells prior to microscopy. Cells were imaged with a Leica TCS SP2 AOBS confocal microscope. Three-dimensional z-stacks were captured and processed using ImageJ software.

In an embodiment, silencing studies were carried out as follows: cells were seeded in 24-well plates at a density of $2.6 \times 10^4$ cells/cm$^2$ and incubated for 24 h in supplemented DMEM medium at 37° C., 5% $CO_2$, and grown to reach 70-80% confluence prior to transfection. At the time of transfection, the medium was replaced with non-supplemented DMEM. Dendriplexes with N/P ratios of 160 were prepared as previously described. Cells were then transfected using 50 µL dendriplexes in a final volume of 300 µL (siRNA at 0.1 pmol/µL). After 24 h incubation, cells were treated with chloroquine (100 nM) and further incubated for 4 h. Medium was then replaced with fresh supplemented DMEM and incubated another 44 h. Cells were rinsed twice with PBS and then incubated on ice with 0.15% Triton X-100 HKR buffer for 5 min. Cell lysates were centrifuged at 400×g for 5 min and supernatants were further analyzed for luciferase activity with Promega's luciferase assay reagent. Luminescence was measured using a micro-plate reader. Protein concentration in cell lysates was measured using the BSA Protein Assay Kit (Pierce). Luciferase activity of treated cells was expressed as the percentage of luciferase activity relative to non-treated cells. The same protocol was used for the experiments with bD/siRNA dendriplexes at different N/P ratios.

In an embodiment, the synthesis of bBz (21) is as follows: PEG-b[G2]-$N_3$ (47 mg, 5.8 ma) was dissolved in DMF (262 µL). Then, 4-ethynylbenzoic acid (200 mol % per azide, 15 mg, 0.10 mmol) and freshly prepared aqueous solutions of 0.1 M $CuSO_4 \cdot 5H_2O$ (5 mol % per azide, 52 µL) and 0.1 M sodium ascorbate (25 mol % per azide, 262 µL) were added. The resulting solution, with a 0.1 M final concentration of terminal azides in DMF-$H_2O$ (1:1), was stirred at RT for 48 h, and the product was isolated by ultrafiltration (Ultracel® 1,000 MWCO) of the concentrated reaction mixture washing with 0.1 M EDTA (pH 6), sat $NaHCO_3$ and $H_2O$. The final aqueous solution was freeze-dried, and bBz (21) was obtained as a pale yellow foam (54 mg, 98%) and characterized.

In an embodiment, the synthesis of bCh (22) is as follows: PEG-b[G2]-$N_3$ (55 mg, 6.8 ma) was dissolved in DMF (461 µL)/$H_2O$ (31 µL)/$CH_2Cl_2$ (10 µL). Then, O-propargyl cholesterol (200 mol % per azide, 52 mg, 0.12 mmol) and freshly prepared aqueous solutions of 0.1 M $CuSO_4 \cdot 5H_2O$ (5 mol % per azide, 61 µl) and 0.5 M sodium ascorbate (25 mol % per azide, 61µL) were added. The resulting solution was stirred at RT for 48 h, and the product was isolated after precipitation from $CH_2Cl_2$/diethyl ether and ultrafiltration (Ultracel® 1,000 MWCO) of the concentrated reaction mixture washing with MeOH—$H_2O$ (3:2), 0.1 M EDTA (pH 6) and $H_2O$. The final aqueous solution was freeze-dried, and bCh (22) was obtained as a white foam (74 mg, 91%) and characterized.

In an embodiment, the synthesis of bDO3A-Gd (23) is as follows: PEG-b[G2]-$N_3$ (50 mg, 6.2 ma) was dissolved in DMF (279 µL). Then, Alk-DO3A-Gd (150 mol % per azide, 50 mg, 0.08 mmol) and freshly prepared aqueous solutions of 0.1 M $CuSO_4 \cdot 5H_2O$ (10 mol % per azide, 55.8 µL) and 0.1 M sodium ascorbate (50 mol % per azide, 279 µL) were added. The resulting solution, with a 0.1 M final concentration of terminal azides in DMF-$H_2O$ (1:1), was stirred at RT for 48 h, and the product was isolated by ultrafiltration (Ultracel® 1,000 MWCO) of the concentrated reaction mixture washing with 0.1 M EDTA (pH 6) and $H_2O$. The final aqueous solution was freeze-dried to give of bDO3A-Gd) (23) as a white solid (72 mg, 87%). The content of Gd(III) was determined by ICPOES and TGA, which accounted for 80% of the theoretical values in agreement with previous literature results.[31] (Gd %) calcd 10.7, found 8.6+−0.2.

In an embodiment, the synthesis and characterization of PEG(10000)-[G1]-$N_3$ (24) is as follows: EDC.HCl (4 mg, 0.02 mmol) and HOBt were added to a solution of PEG (10000)-$NH_3Cl$ (100 mg, 9.92 ma) and hydrolytically stable GATG unit 7 (13 mg, 0.02 mmol) in dry $CH_2Cl_2$ (300 µL). The resulting solution was stirred at room temperature for 12 h under Ar, and then it was concentrated and precipitated from $CH_2Cl_2$/iPrOH to give pure PEG(10000)-[G1]-$N_3$ as a white powder (99 mg, 94%).

In an embodiment, the synthesis and characterization of PEG(10000)-b[G2]-$N_3$ (25) was made as follows: Pd/C (20 mg, 10% w/w) was added to a solution of PEG(10000)-[G1]-$N_3$ (99 mg, 9.37 ma) in MeOH (3 mL). The resulting mixture was vigorously stirred under $H_2$ (1 atm) for 3 h. Then, the catalyst was removed by filtration and the filtrate was concentrated and dried. HOBt (6 mg, 0.04 mmol) and EDC.HCl (8 mg, 0.04 mmol) were added to a solution of the above residue and 5 (38 mg, 0.04 mmol) in dry $CH_2Cl_2$ (281 µL). The resulting solution was stirred for 48 h at RT under inert atmosphere (Ar), and then it was concentrated and precipitated from $CH_2Cl_2$/iPrOH to give PEG(10000)-b[G2]-$N_3$ as a white powder (108 mg, 88%). FTIR (KBr): 3428, 2883, 2109, 1734, 1115 $cm^{-1}$. $^1$H NMR (400 MHz, $CD_2Cl_2$) δ: 1.90-2.11 (m, 18H), 2.45-2.58 (m, 18H), 3.30-3.35 (m, 21H), 3.39-3.78 (m, ~974H), 3.94-4.05 (m, 18H), 4.09-4.19 (m, 24H), 7.05-7.08 (m, 8H).

In an embodiment, the solvent peaks labeled as * in spectra in the $^1$H and $^{13}$C NMR spectra.

In an embodiment, the MALDI-TOF spectrum of PEG-b[G2]-$N_3$ (9) was acquired. Mn=8068.49; Mw=8085.27; PDI=1.002

In an embodiment, the FTIR transmittance spectrum of PEG-b[G2]-$N_3$ (9), bD (15), bB (16), hsD (19) and hsB (20) (ATR) were obtained.

In an embodiment, biodegradable PEG-GATGE dendritic block copolymers were synthesized from GATGE building units and their biofunctionality assessed as non-viral vectors of nucleic acids in gene therapy applications. Their functionalization with different amine moieties was tested. This amine-functionalization allowed to complex siRNA and, therefore, to explore their functionality assessment as vectors of this nucleic acid. But, in the same way/using the same protocol, the biodegradable dendritic repeating unit can be easily functionalized with different functional groups. Therefore, dendritic structures derived from this bRU will be able to act as suitable vectors not only for nucleic acid delivery, but also for application in broader drug delivery, magnetic resonance imaging (MRI), vaccines, tissue engineering, among others, finally leading to new strategies for nanomedicine.

These nanomaterials can serve as carriers of great variety of important biomolecules, such as nucleic acids, drugs, growth factors, MRI agents, among other.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable. The following claims further set out particular embodiments of the disclosure.

REFERENCES (1) a) Skrifvars, M., Tulisalo, J., Rissanen, K., and Nummelin, S. Maleimide Modified Polypropylene Imine Dendrimers and a Process for their Preparation. WO 01/38423 AI, 2001; b) Baker, J. R., and Zhang, Y. Hydroxyl-Terminated Dendrimers. WO 2011/053618 A2, 2011; c) Tomalia, D. A., and Majoros, I. J. Biocompatible Dendrimers. US 2004/0151689 A1, 2004; d) Svenson, S., and Tomalia, D. (2005) Dendrimers in biomedical applications—reflections on the field. *Adv Drug Deliver Rev* 57, 2106-2129; e) Rolland, O., Turrin, C. O., Caminade, A. M., and Majoral, J. P. (2009) Dendrimers and nanomedicine: multivalency in action. *New J. Chem.* 33, 1809-1824; f) Medina, S. H., and EI-Sayed, M. E. (2009) Dendrimers as carriers for delivery of chemotherapeutic agents. *Chem. Rev.* 109, 3141-57; g) Tekade, R. K., Kumar, P. V., and Jain, N. K. (2009) Dendrimers in oncology: an expanding horizon. *Chem. Rev.* 109, 49-87; h) Mintzer, M. A., and Grinstaff, M. W. (2011) Biomedical applications of dendrimers: a tutorial. *Chem. Soc. Rev.* 40, 173-90; i) Leiro, V., Santos, S. D., Lopes, C. D. F., and Pêgo, A. P. (2017. DOI: 10.1002/adfm.201700313) Dendrimers as Powerful Building Blocks in Central Nervous System Disease: Headed for Successful Nanomedicine. *Advanced Functional Materials*.

(2) a) Barth, R. F., Adams, D. M., Soloway, A. H., Alam, F., and Darby, M. W. (1994) Boronated starburst dendrimer-monoclonal antibody immunoconjugates: evaluation as a potential delivery system for neutron capture therapy. *Bioconjugate Chemistry* 5, 58-66; b) Malik, N., Evagorou, E., and Duncan, R. (1999) Dendrimer-platinate: a novel approach to cancer chemotherapy. *Anticancer Drugs* 10, 767-776; c) Malik, N., Wiwattanapatapee, R., Klopsch, R., Lorenz, K., Frey, H., Weener, J. W., Meijer, E. W., Paulus, W., and Duncan, R. (2000) Dendrimers: relationship between structure and biocompatibility in vitro, and preliminary studies on the biodistribution of $^{125}$I-labelled polyamidoamine dendrimers in vivo. *Journal of Controlled Release* 65, 133-148; d) Jain, K., Kesharwani, P., Gupta, U., and Jain, N. K. (2010) Dendrimer toxicity: let's meet the challenge. *International Journal of Pharmaceutics* 394, 122-142.

(3) Leiro, V., Garcia, J. P., Tomas, H., and Pego, A. P. (2015) The Present and the Future of Degradable Dendrimers and Derivatives in Theranostics. *Bioconjugate Chemistry* 26, 1182-1197.

(4) a) Labieniec, M., Ulicna, O., Vancova, O., Glowacki, R., Sebekova, K., Bald, E., Gabryelak, T., and Watala, C. (2008) PAMAM G4 dendrimers lower high glucose but do not improve reduced survival in diabetic rats. *International Journal of Pharmaceutics* 364, 142-149; b) Li, C., Liu, H., Sun, Y., Wang, H., Guo, F., Rao, S., Deng, J., Zhang, Y., Miao, Y., Guo, C., Meng, J., Chen, X., Li, L., Li, D., Xu, H., Wang, H., Li, B., and Jiang, C. (2009) PAMAM nanoparticles promote acute lung injury by inducing autophagic cell death through the Akt-TSC2-mTOR signaling pathway. *Journal of Molecular Cell Biology* 1, 37-45; c) Jones, C. F., Campbell, R. A., Brooks, A. E., Assemi, S., Tadjiki, S., Thiagarajan, G., Mulcock, C., Weyrich, A. S., Brooks, B. D., Ghandehari, H., and Grainger, D. W. (2012) Cationic PAMAM dendrimers aggressively initiate blood clot formation. *ACS Nano* 6, 9900-9910.

(5) a) Jianbin, A., Youqing, S., Tingting, L., and Meihua, S. Degradable dendritic macromolecule magnetic resonance contrast agent and preparation method thereof. CN103055328A, 2013; b) Ye, M., Qian, Y., Shen, Y., Hu, H., Sui, M., and Tang, J. (2012) Facile synthesis and in vivo evaluation of biodegradable dendritic MRI contrast agents. *J Mater Chem* 22, 14369-14377.

(6) a) Guillaudeu, S. J., Fox, M. E., Haidar, Y. M., Dy, E. E., Szoka, F. C., and Fréchet, J. M. J. (2008) PEGylated dendrimers with core functionality for biological applications. *Bioconjugate chemistry* 19, 461-469; b) van der Poll, D. G., Kieler-Ferguson, H. M., Floyd, W. C., Guillaudeu, S. J., Jerger, K., Szoka, F. C., and Fréchet, J. M. (2010) Design, synthesis, and biological evaluation of a robust, biodegradable dendrimer. *Bioconjugate Chemistry* 21, 764-773.

(7) Leinweber, D., Feustel, M., Wasmund, E., and Rausch, H. Alkoxyltated Dendrimers and use thereof as Biodegradable Demulsifiers. WO2005003260 A1 2005.

(8) Tyler, P. C., and Zubkova, O. V. Dendritic Core Compounds. US 2015/0291522 A1, 2015.

(9) Castanotto, D., and Rossi, J. J. (2009) The promises and pitfalls of RNA-interference-based therapeutics. *Nature* 457, 426-433.

(10) a) Yiyun, C., and Mingming, W. Dendrimer Gene Carrier Modified by Fluorine-containing Aromatic Ring Compound as well as Preparation Method and Application thereof CN103881108A, 2014; b) Kang, C., Pu, P., Yuan, X., Li, F., and Zhong, Y. Functional Dendritic Polymer Gene Vector System of Targeted Malignant Cerebroma. CN101337076A, 2009; c) Santoyo, F., Morales, J., Megia, A., Hernandez, F., Giron, M. D., and Salto, R. Dendrimers Based on PAMAM Derizatized with Alkyl Sulfonyl Groups. WO2012/049338A1, 2012; d) Dufes, C., Uchegbu, I., and Schatzlein, A. (2005) Dendrimers in gene delivery. *Adv Drug Deliver Rev* 57, 2177-2202; e) Mintzer, M. A., and Simanek, E. E. (2009) Nonviral vectors for gene delivery. *Chemical Reviews* 109, 259-302; f) Biswas, S., and Torchilin, V. P. (2013) Dendrimers for siRNA delivery. *Pharmaceuticals* 6, 161-183; g) Santos, J. L., Oliveira, H., Pandita, D., Rodrigues, J., Pêgo, A. P., Granja, P. L., and Tomas, H. (2010) Functionalization of poly(amidoamine) dendrimers with hydrophobic chains for improved gene delivery in mesenchymal stem cells. *Journal of Controlled Release* 144, 55-64; h) Leiro, V., Santos, S. D., and Pêgo, A. P. (2017.) Delivering siRNA with Dendrimers: In Vivo Applications *Current Gene Therapy*. DOI: 10.2174/1566523217666170510160527.

(11) Thakur, S., Kesharwani, P., Tekade, R. K., and Jain, N. K. (2015) Impact of pegylation on biopharmaceutical properties of dendrimers. *Polymer* 59, 67-92.

(12) Sousa-Herves, A., Riguera, R., and Fernandez-Megia, E. (2012) PEG-dendritic block copolymers for biomedical applications. *New J. Chem.* 36, 205-210.

(13) Reyes-Reveles, J., Sedaghat-Herati, R., Gilley, D. R., Schaeffer, A. M., Ghosh, K. C., Greene, T. D., Gann, H. E., Dowler, W. A., Kramer, S., Dean, J. M., and Delong, R. K. (2013) mPEG-PAMAM-G4 Nucleic Acid Nanocomplexes: Enhanced Stability, RNase Protection, and Activity of Splice Switching Oligomer and Poly I:C RNA. *Biomacromolecules* 14, 4108-4115.

(14) Barnard, A., Posocco, P., Pricl, S., Calderon, M., Haag, R., Hwang, M. E., Shum, V. W., Pack, D. W., and Smith, D. K. (2011) Degradable self-assembling dendrons for gene delivery: experimental and theoretical insights into the barriers to cellular uptake. *J Am Chem Soc* 133, 20288-20300.
(15) a) Welsh, D. J., Jones, S. P., and Smith, D. K. (2009) "On-off" multivalent recognition: degradable dendrons for temporary high-affinity DNA binding. *Angewandte Chemie, International Edition* 48, 4047-4051; b) Barnard, A., Calderon, M., Tschiche, A., Haag, R., and Smith, D. K. (2012) Effects of a PEG additive on the biomolecular interactions of self-assembled dendron nanostructures. *Organic & biomolecular chemistry* 10, 8403-8409; c) Barnard, A., Posocco, P., Fermeglia, M., Tschiche, A., Calderon, M., Pricl, S., and Smith, D. K. (2014) Double-degradable responsive self-assembled multivalent arrays—temporary nanoscale recognition between dendrons and DNA. *Organic & biomolecular chemistry* 12, 446-455; d) Movellan, J., Gonzalez-Pastor, R., Martin-Duque, P., Sierra, T., de la Fuente, J. M., and Serrano, J. L. (2015) New Ionic bis-MPA and PAMAM Dendrimers: A Study of Their Biocompatibility and DNA-Complexation. *Macromol. Biosci.* 15, 657-67.
(16) Amaral, S. P., Fernandez-Villamarin, M., Correa, J., Riguera, R., and Fernandez-Megia, E. (2011) Efficient Multigram Synthesis of the Repeating Unit of Gallic Acid-Triethylene Glycol Dendrimers. *Org Lett* 13, 4522-4525.
(17) Hurrell, S., Milroy, G. E., and Cameron, R. E. (2003) The degradation of polyglycolide in water and deuterium oxide. *Part* 1: The effect of reaction rate. *Polymer* 44, 1421-1424.
(18) Fernandez-Megia, E., Correa, J., and Riguera, R. (2006) "Clickable" PEG-dendritic block copolymers. *Biomacromolecules* 7, 3104-3111.
(19) Gary, D. J., Puri, N., and Won, Y. Y. (2007) Polymer-based siRNA delivery: Perspectives on the fundamental and phenomenological distinctions from polymer-based DNA delivery. *Journal of Controlled Release* 121, 64-73.
(20) a) Mintzer, M. A., Merkel, O. M., Kissel, T., and Simanek, E. E. (2009) Polycationic triazine-based dendrimers: effect of peripheral groups on transfection efficiency. *New J Chem* 33, 1918-1925; b) Merkel, O. M., Mintzer, M. A., Sitterberg, J., Bakowsky, U., Simanek, E. E., and Kissel, T. (2009) Triazine dendrimers as nonviral gene delivery systems: effects of molecular structure on biological activity. *Bioconjug Chem* 20, 1799-806; c) Merkel, O. M., Mintzer, M. A., Librizzi, D., Samsonova, O., Dicke, T., Sproat, B., Garn, H., Barth, P. J., Simanek, E. E., and Kissel, T. (2010) Triazine dendrimers as nonviral vectors for in vitro and in vivo RNAi: the effects of peripheral groups and core structure on biological activity. *Mol Pharm* 7, 969-83.
(21) Fernandez-Villamarin, M., Sousa-Herves, A., Porto, S., Guldris, N., Martinez-Costas, J., Riguera, R., and Fernandez-Megia, E. Unpublished results.
(22) Akin, A., and Giuseppe, B. (2013) Exploiting endocytosis for nanomedicines. *Cold Spring Harbor perspectives in biology* 5.
(23) Merkel, O. M., Zheng, M., Mintzer, M. A., Pavan, G. M., Librizzi, D., Maly, M., Hoffken, H., Danani, A., Simanek, E. E., and Kissel, T. (2011) Molecular modeling and in vivo imaging can identify successful flexible triazine dendrimer-based siRNA delivery systems. *Journal of controlled release: official journal of the Controlled Release Society* 153, 23-33.
(24) de la Fuente, M., Ravina, M., Sousa-Herves, A., Correa, J., Riguera, R., Fernandez-Megia, E., Sanchez, A., and Alonso, M. J. (2012) Exploring the efficiency of gallic acid-based dendrimers and their block copolymers with PEG as gene carriers. *Nanomedicine* 7, 1667-1681.
(25) a) Merkel, O. M., Beyerle, A., Beckmann, B. M., Zheng, M., Hartmann, R. K., Stoger, T., and Kissel, T. H. (2011) Polymer-related off-target effects in non-viral siRNA delivery. *Biomaterials* 32, 2388-98; b) Beyerle, A., Irmler, M., Beckers, J., Kissel, T., and Stoeger, T. (2010) Toxicity pathway focused gene expression profiling of PEI-based polymers for pulmonary applications. *Mol Pharm* 7, 727-37.
(26) Mahesh, L. P., Min, Z., Oleh, T., Olga, B. G., Huixin, H., and Tamara, M. (2009) Internally cationic polyamidoamine PAMAM-OH dendrimers for siRNA delivery: effect of the degree of quaternization and cancer targeting. *Biomacromolecules* 10, 258-266.
(27) a) Erbacher, P., Roche, A. C., Monsigny, M., and Midoux, P. (1996) Putative role of chloroquine in gene transfer into a human hepatoma cell line by DNA lactosylated polylysine complexes. *Exp Cell Res* 225, 186-194; b) Ciftci, K., and Levy, R. J. (2001) Enhanced plasmid DNA transfection with lysosomotropic agents in cultured fibroblasts. *Intl Pharm* 218, 81-92.
(28) Moreira, C., Oliveira, H., Pires, L. R., Simoes, S., Barbosa, M. A., and Pego, A. P. (2009) Improving chitosan-mediated gene transfer by the introduction of intracellular buffering moieties into the chitosan backbone. *Acta biomaterialia* 5, 2995-3006.
(29) Fernandez-Trillo, F., Pacheco-Torres, J., Correa, J., Ballesteros, P., Lopez-Larrubia, P., Cerdan, S., Riguera, R., and Fernandez-Megia, E. (2011) Dendritic MRI contrast agents: an efficient prelabeling approach based on CuAAC. *Biomacromolecules* 12, 2902-7.
(30) Yashima, E., Matsushima, T., and Okamoto, Y. (1997) Chirality assignment of amines and amino alcohols based on circular dichroism induced by helix formation of a stereoregular poly((4-carboxyphenyl)acetylene) through acid-base complexation. *J Am Chem Soc* 119, 6345-6359.
(31) Langereis, S., Lussanet, Q. G. d., van Genderen, M. H. P., Backes, W. H., and Meijer, E. W. (2004) Multivalent contrast agents based on gadolinium-diethylenetriaminepentaacetic acid-terminated poly(propylene imine) dendrimers for magnetic resonance imaging. *Macromolecules* 37, 3084-3091.

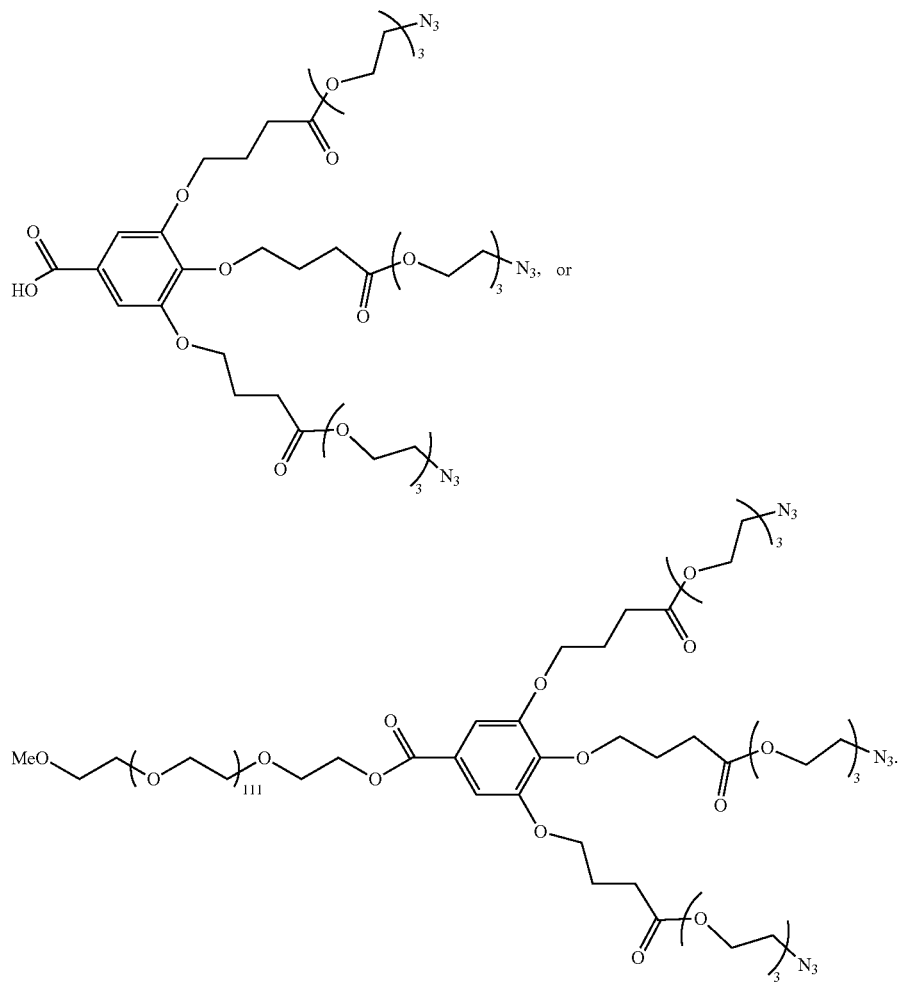

The invention claimed is:

1. A biodegradable dendritic structure of formula I:

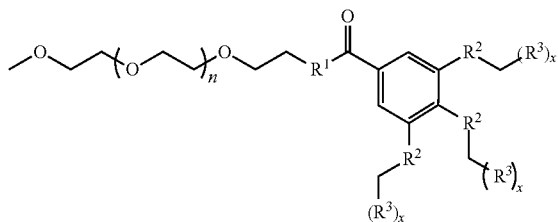

wherein,
n is between 40-350;
x is between 0-4;
$R^1$ is selected from NH, O, or S;
$R^2$ is

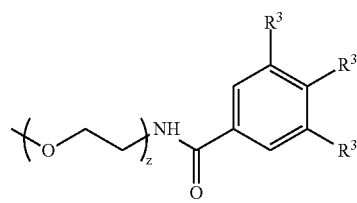

or

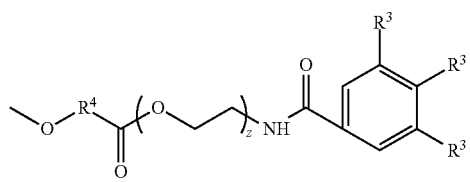

z is between 1-9;
$R^3$ is $R^2$ with the exception that, at a dendritic structure end, $R^3$ is

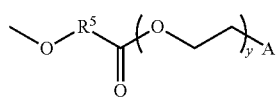

wherein A is selected from the group consisting of: an amine group, an amide group, an azide group, a hydroxyl group, a thiol group, a carboxyl group, an isocyanate, an alkene, and an alkyne group;
y is between 1-9;
$R^4$ or $R^5$ is a $C_1$-$C_6$ alkyl chain; and
A, $R^1$, $R^2$, $R^3$, $R^4$, $R^5$, n, x, y and z are independently selected from each other.

2. The biodegradable dendritic structure of claim 1, wherein n is 90-120.

3. The biodegradable dendritic structure of claim 1, wherein x is 1-2.

4. The biodegradable dendritic structure of claim 1, wherein y is 3-4.

5. The biodegradable dendritic structure of claim 1, wherein z is 3-4.

6. The biodegradable dendritic structure of claim 1, wherein $R^4$ or $R^5$ is $C_3$-$C_4$ alkyl chain.

7. The biodegradable dendritic structure of claim 1, wherein the amine group is an propylenediamine group, benzylamine group, or other alkylene polyamines, an aromatic amine, a guanidinium group, a tertiary amine, an imidazole, a histidine or mixtures thereof.

8. The biodegradable dendritic structure of claim 1, further comprising: an amine group, a hydroxyl group, a thiol group, a carboxylic acid, an isocyanate, an azide, an alkyne, a cyclooctin, an alkene, or an acrylate, replacing the $OCH_3$ group.

9. The biodegradable dendritic structure of claim 1, wherein the biodegradable dendrite structure has a molecular weight between 2500-75000 g/mol.

10. The biodegradable dendritic structure of claim 1, further comprising a ligand.

11. The biodegradable dendritic structure of claim 10, wherein the ligand is a hydrophobic group, an aliphatic chain, an aromatic group, a fluorescent tag, a chemical drug, a contrast agent, an escaping cell endosomal molecule or biomolecule, a nucleus localization agent, and biomolecule release, a stabilization agent, or a biomolecule.

12. The biodegradable dendritic structure of claim 1, wherein the ligand is selected from the group consisting of: 1,3-propylene diamine, benzylamine, benzoic acid, cholesterol, 2,2',2''-(10-(2-(methylamino)-2-oxoethyl)-1,4,7,10-tetraazacyclododecane-1,4,7-triyl)-triacetate gadolinium (III) complex, and mixtures thereof.

13. The biodegradable dendritic structure of claim 1, wherein the biomolecule is a protein, a growth factor, or a nucleic acid.

14. The biodegradable dendritic structure of claim 1, further comprising a targeting ligand.

15. The biodegradable dendritic structure of claim 14, wherein the targeting ligand is a peptide, a protein, a monosaccharide, a polysaccharide, an antibody, an aptamer, a glycosaminoglycan, an agent that facilitates receptor recognition, an internalization agent, or mixtures thereof.

16. The biodegradable dendritic structure of claim 14, wherein the targeting ligand is bound to the biodegradable dendritic structure.

17. The biodegradable dendritic structure of claim 1, wherein said structure is compound n.5, n.9, n.10, n. 11, n. 12, n. 15, n. 16, n. 17, n.18, n. 21, n. 22, n. 23, or n.25.

18. The biodegradable dendritic structure of claim 1, wherein the structure is suitable for the treatment or prevention of cancer.

19. The biodegradable dendritic structure of claim 1, wherein the structure is suitable for inclusion in nucleic acid delivery therapy, in drug delivery therapy, or regenerative medicine or gene therapy.

20. The biodegradable dendritic structure of claim 1, wherein the structure is suitable as an imaging agent.

21. The biodegradable dendritic structure of claim 1, wherein the structure is a carrier for administering a diagnostic agent.

22. A biodegradable dendritic structure of one of the following formulas: